US010463753B2

(12) United States Patent
Grice et al.

(10) Patent No.: US 10,463,753 B2
(45) Date of Patent: Nov. 5, 2019

(54) RADIOLABELED MONOACYLGLYCEROL LIPASE OCCUPANCY PROBE

(71) Applicant: LUNDBECK LA JOLLA RESEARCH CENTER, INC., San Diego, CA (US)

(72) Inventors: Cheryl A. Grice, Encinitas, CA (US); Todd K. Jones, Solana Beach, CA (US); Justin S. Cisar, San Diego, CA (US); Iain Peter Fraser, Scotch Plains, NJ (US)

(73) Assignee: LUNDBECK LA JOLLA RESEARCH CENTER, INC., San Diego, CA (US)

( * ) Notice: Subject to any disclaimer, the term of this patent is extended or adjusted under 35 U.S.C. 154(b) by 0 days.

(21) Appl. No.: 15/999,117

(22) PCT Filed: Feb. 17, 2017

(86) PCT No.: PCT/US2017/018502
§ 371 (c)(1),
(2) Date: Aug. 16, 2018

(87) PCT Pub. No.: WO2017/143283
PCT Pub. Date: Aug. 24, 2017

(65) Prior Publication Data
US 2019/0046668 A1    Feb. 14, 2019

Related U.S. Application Data

(60) Provisional application No. 62/297,690, filed on Feb. 19, 2016.

(51) Int. Cl.
*A61K 51/00* (2006.01)
*A61M 36/14* (2006.01)
*A61K 51/04* (2006.01)
*C12N 9/20* (2006.01)
*A61B 6/03* (2006.01)
*C07B 59/00* (2006.01)
*C07D 295/205* (2006.01)

(52) U.S. Cl.
CPC .......... *A61K 51/0459* (2013.01); *A61B 6/037* (2013.01); *C07B 59/002* (2013.01); *C07D 295/205* (2013.01); *C12N 9/20* (2013.01); *C12Y 301/01023* (2013.01); *C07B 2200/05* (2013.01)

(58) Field of Classification Search
CPC ........ A61K 51/0459; C12Y 301/01023; A61B 6/037; C12N 9/20; C07B 2200/05
USPC ....................................................... 424/1.89
See application file for complete search history.

(56) References Cited

U.S. PATENT DOCUMENTS

| 9,133,148 | B2 | 9/2015 | Cisar et al. |
|---|---|---|---|
| 9,487,495 | B2 | 11/2016 | Cisar et al. |
| 9,771,341 | B2 | 9/2017 | Cisar et al. |
| 9,957,242 | B2 | 5/2018 | Cisar et al. |
| 9,994,537 | B2 | 6/2018 | Cisar et al. |
| 2009/0269785 | A1 | 10/2009 | Schubert et al. |
| 2015/0148330 | A1 | 5/2015 | Cisar et al. |
| 2016/0137649 | A1 | 5/2016 | Jones et al. |
| 2018/0208568 | A1 | 7/2018 | Cisar et al. |

FOREIGN PATENT DOCUMENTS

| DE | 1802739 A1 | 6/1969 |
|---|---|---|
| JP | S6183073 A | 4/1986 |
| JP | 2000500448 A | 1/2000 |
| JP | 2008500270 A | 1/2008 |
| JP | 2008521768 A | 6/2008 |
| JP | 2009523729 A | 6/2009 |
| JP | 2010513447 A | 4/2010 |
| RU | 2167150 C2 | 5/2001 |
| WO | WO-8911794 A1 | 12/1989 |
| WO | WO-9311097 A1 | 6/1993 |
| WO | WO-9517439 A2 | 6/1995 |
| WO | WO-9800408 A1 | 1/1998 |
| WO | WO-0125188 A1 | 4/2001 |
| WO | WO-0234382 A1 | 5/2002 |
| WO | WO-2005063698 A1 | 7/2005 |
| WO | WO-2005070910 A2 | 8/2005 |
| WO | WO-2005080363 A1 | 9/2005 |
| WO | WO-2006074025 A1 | 7/2006 |
| WO | WO-2008106047 A2 | 9/2008 |
| WO | WO-2009141238 A1 | 11/2009 |
| WO | WO-2010009207 A1 | 1/2010 |
| WO | WO-2010056309 | 5/2010 |
| WO | WO-2010063802 A1 | 6/2010 |
| WO | WO-2010111050 A1 | 9/2010 |
| WO | WO-2010124116 A1 | 10/2010 |
| WO | WO-2010124119 A1 | 10/2010 |

(Continued)

OTHER PUBLICATIONS

Miller et al. Angew. Chem. Int. Ed. 2008, 47, 8998-9033.*

(Continued)

*Primary Examiner* — Michael G. Hartley
*Assistant Examiner* — Sean R Donohue
(74) *Attorney, Agent, or Firm* — Wilson Sonsini Goodrich & Rosati

(57) ABSTRACT

Provided herein are monoacylglycerol lipase (MGLL) occupancy probes comprising a MGLL inhibitor containing a positron emission tomography (PET) tracer radionuclide. Also provided are methods of assessing MGLL enzyme occupancy of a MGLL inhibitor using the radiolabeled occupancy probes described herein.

10 Claims, 9 Drawing Sheets

(56) References Cited

FOREIGN PATENT DOCUMENTS

| WO | WO-2010124121 A1 | 10/2010 | | |
|----|------------------|---------|---|---|
| WO | WO-2010124122 A1 | 10/2010 | | |
| WO | WO-2010129497 A1 | 11/2010 | | |
| WO | WO-2011054795 A1 | 5/2011 | | |
| WO | WO-2011151808 A1 | 12/2011 | | |
| WO | WO-2012030907 A1 | 3/2012 | | |
| WO | WO-2012054716 A1 | 4/2012 | | |
| WO | WO-2012054721 A1 | 4/2012 | | |
| WO | WO-2013049332 A1 | 4/2013 | | |
| WO | WO-2013102431 A1 | 7/2013 | | |
| WO | WO-2013103973 A1 * | 7/2013 | ........... | C07D 405/14 |
| WO | WO-2013142307 A1 | 9/2013 | | |
| WO | WO-2013159095 A1 | 10/2013 | | |
| WO | WO-2015003002 A1 | 1/2015 | | |
| WO | WO-2015179559 A2 | 11/2015 | | |
| WO | WO-2016014975 A2 | 1/2016 | | |
| WO | WO-2016149401 A2 | 9/2016 | | |
| WO | WO-2016183097 A1 | 11/2016 | | |
| WO | WO-2017143283 A1 | 8/2017 | | |
| WO | WO-2018053447 A1 | 3/2018 | | |

OTHER PUBLICATIONS

Wang et al. ACS Chem Neurosci. 2016, 484-489.*
Chi et al. J. Org. Chem. 1987, 52, 658-664.*
Blankman et al. A comprehensive profile of brain enzymes that hydrolyze the endocannabinoid 2-arachidonoylglycerol. Chem. Biol. 14:1347-1356 (2007).
Chang et al. Highly Selective Inhibitors of Monoacylglycerol Lipase Bearing a Reactive Group that is Bioisosteric with Endocannabinoid Substrates. ChemBiol 19(5):579-588 (2012).
Chang et al. Proteome-wide reactivity profiling identifies diverse carbamate chemotypes tuned for serine hydrolase inhibition. ACS Chem Biol 8:1590-1599 (2013).
Fowler. Monoacylglycerol lipase—a target for drug development? Br Pharmacol. 166:1568-1585 (2012).
Hicks. Discovery and Preclinical Evaluation of Novel Enzyme Targeting Radiotracers for Positron Emission Tomography. Thesis. Institute of Medical Science, University of Toronto. http://gradworks.umi.com/37/16/3716105.html (245 pgs) (2015).
Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).
Machac. Radiopharmaceuticals for Clinical Cardiac PET Imaging. Cardiac PET and PET/CT Imaging (pp. 73-82) (2007).
Meanwell et al. Synopsis of some recent tactical application of bioisosteres in drug design. J Med Chem 54(8):2529-2591 (2011).
Patani et al. Bioisosterism: A Rational Approach in Drug Design. Chem. Rev. 96:3147-3176 (1996).
PCT/US2013/020551 International Preliminary Report on Patentability dated Jul. 17, 2014.
PCT/US2013/020551 International Search Report dated May 21, 2013.
PCT/US2016/022690 International Search Report and Written Opinion dated Aug. 30, 2016.
PCT/US2017/018502 International Search Report and Written Opinion dated May 16, 2017.
PCT/US2017/052106 International Search Report and Written Opinion dated Jan. 17, 2018.
PCT/US2017/052106 Invitation to Pay Additional Fees dated Nov. 14, 2017.
PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).
PubChem CID 3469875. http://pubchem.ncbi.nlm.nih.gov/summary/summary.cgi?cid=3469875Retrieved Mar. 4, 2013 Create Date: Sep. 8, 2005 (11 pgs.).
PubChem CID 669902 http://pubchem.ncbi.nlm.nih.gov/summary/summary.cgi?cid=669902 Retrieved May 1, 2013 Create Date: Jul. 8, 2005 (4 pgs.).
PubMed Compund Summary for CID 71656983, 'SCHEMBL15100862'. Available at https://pubchem.ncbi.nlm.nih.gov/compound/71656983. U.S. National Library of Medicine (11 pgs.) (Aug. 19, 2013).
Rautio et al. Prodrugs: design and clinical applications. Nat Rev Drug Discov 7(3):255-270 (2008).
Silverman. The Organic Chemistry of Drug Design and Drug Action. Academic Press (pp. 15-22) (1992).
Skaddan et al. The synthesis and in vivo evaluation of [18913F-9811: a novel PET ligand for imaging brain fatty acid amide hydrolase (FAAH). Nucl Med Biol 39:1058-1067 (2012).
Thornber. Isosterism and molecular modification in drug design. Chem Soc Rev 8:563-580 (1979).
U.S. Appl. No. 14/369,982 Office Action dated Mar. 8, 2016.
U.S. Appl. No. 14/369,982 Office Action dated Oct. 22, 2015.
U.S. Appl. No. 14/599,105 Office Action dated Apr. 8, 2015.
U.S. Appl. No. 15/072,229 First Action Interview dated Sep. 19, 2016.
U.S. Appl. No. 15/072,229 Office Action dated Jan. 10, 2017.
U.S. Appl. No. 15/272,313 Office Action dated Apr. 10, 2017.
U.S. Appl. No. 15/272,313 Office Action dated Aug. 25, 2017.

* cited by examiner

RADIOLABELED MONOACYLGLYCEROL LIPASE OCCUPANCY PROBE

CROSS-REFERENCE

This application is filed pursuant to 35 U.S.C. § 371 as a United States National Phase Application of International Application No. PCT/US2017/018502, filed on Feb. 17, 2017, which claims the benefit of U.S. Provisional Application No. 62/297,690, filed Feb. 19, 2016, each of which are herein incorporated by reference in their entirety.

BACKGROUND

Monoacylglycerol lipase (MGLL) inhibitors are a potential therapeutic drug target for the treatment of central nervous system (CNS) disorders. Clinical evaluation of MGLL expression, distribution, and enzyme occupancy by candidate therapeutic inhibitors in the CNS requires the development of non-invasive quantitative techniques, such as specific radiolabeled ligands. Access to an imaging ligand for MGLL would provide a valuable resource for occupancy studies, which play a key role in the development of therapeutics targeting the CNS.

SUMMARY OF THE INVENTION

Described herein are radiolabeled MGLL occupancy probes. In one aspect is a radiolabeled monoacylglycerol lipase (MGLL) occupancy probe comprising a MGLL inhibitor containing a positron emission tomography (PET) tracer radionuclide; wherein the PET tracer radionuclide is $^{18}$F, $^{15}$O, or $^{13}$N. In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{18}$F. In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{15}$O. In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{13}$N, In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{18}$F, $^{15}$O, or $^{13}$N; and the radiolabeled MGLL occupancy probe forms a covalent adduct with the active-site serine in MGLL.

In another aspect described herein is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (I):

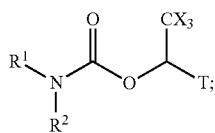

Formula (I)

wherein
T is $CX_3$ or

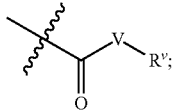

X is selected independently, for each occurrence, from H, F, Cl or Br; wherein at least three occurrences of X are F;
V is O or $NR^a$;
$R^V$ is selected from the group consisting of hydrogen, $C_1$-$C_6$alkyl, $C_2$-$C_6$alkenyl, $C_{3-6}$ cycloalkyl, phenyl, heteroaryl, and heterocyclyl, or when $R^a$ and $R^V$ occur together with the nitrogen to which they are attached, form a 4-6 membered heterocyclic ring which may have an additional heteroatom selected from O, S, and N; wherein $C_1$-$C_6$alkyl, $C_2$-$C_6$alkenyl, phenyl, heterocyclic ring and heterocyclyl are optionally substituted by one, two, or three moieties independently selected from the group consisting of halogen, hydroxyl, $C_1$-$C_6$alkyl, cyano, and phenyl; and
wherein
a)
$R_1$ and $R_2$ taken together with the nitrogen to which they are attached form a moiety selected from:
a 4-7 membered heterocyclic ring B having an additional nitrogen; or
a 4-7 membered heterocyclic ring A;
wherein one carbon of ring A has a substituent represented by:

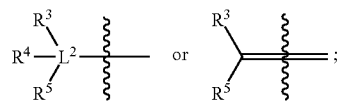

$L^2$ is $C_1$-$C_6$alkylene or $C_1$-$C_6$alkylene-$NR^a$—;
$R^3$ and $R^5$ are each independently selected from phenyl, naphthyl, a mono or bicyclic heteroaryl and a mono or bicyclic heterocycle, wherein the heterocycle or heteroaryl has 1, 2 or 3 heteroatoms independently selected from O, S, and N; and wherein $R^3$ and $R^5$ may be independently and optionally substituted by one, two, three, or four moieties each independently selected from $R^g$;
$R^4$ is selected from the group consisting of H, halogen, hydroxyl, cyano, and $C_1$-$C_5$alkoxy;
A is optionally substituted on another carbon by one, two, three, or four substituents each independently selected from $R^d$;
the additional nitrogen of ring B has a substituent represented by:

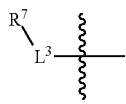

$L^3$ is selected from the group consisting of: a bond, $C_1$-$C_6$alkylene, —C(O)—, $C_1$-$C_6$alkylene-C(O)—, C(O)—$C_1$-$C_6$alkylene-, $NR^a$—C(O)—$C_1$-$C_6$alkylene-, $C_1$-$C_6$alkylene-O—C(O)—, —S(O)$_w$—, and $C_1$-$C_6$alkylene-S(O)$_w$—, wherein w is 0, 1, or 2, and wherein $C_1$-$C_6$alkylene is optionally substituted by one or two substituents selected from the group consisting of: halogen, hydroxyl, cyano, and an additional $R^7$, wherein when $L^3$ is $-S(O)_w-$, then $R^7$ is not H;

$R^7$ is selected from the group consisting of: H, phenyl, naphthyl, mono or bicyclic heteroaryl, and mono or bicyclic heterocyclyl, wherein the heteroaryl or the heterocyclyl has 1, 2 or 3 heteroatoms independently selected from O, S, and N; wherein $R^7$ is optionally substituted by one, two, three, or four moieties independently selected from $R^h$;

B is optionally substituted on one or more carbons by one, two, three, or four moieties each independently selected from $R^d$;

or b)

$R^1$ is-$L^1$-$R^6$;

$R^2$ is H or $C_1$-$C_6$alkyl;

$L^1$ is $C_1$-$C_6$alkylene or a bond;

$R^6$ is selected from the group consisting of phenyl, naphthyl, a mono or bicyclic heteroaryl, and a mono or bicyclic heterocycle, wherein the heteroaryl or heterocycle has 1, 2 or 3 heteroatoms independently selected from O, S, and N; and $R^6$ is optionally substituted by one, two, three, or four moieties independently selected from the group consisting of: halogen, phenyl (optionally substituted by one, two, or three moieties independently selected from $R^c$), phenyloxy (optionally substituted by one, two, or three moieties independently selected from $R^c$), anilinyl (optionally substituted on a carbon by one, two or three moieties independently selected from $R^c$), hydroxyl, cyano, $C_{1-6}$alkyl (optionally substituted by cyano, hydroxyl, or one, two, or three halogens), $C_{1-6}$alkoxy (optionally substituted by cyano, hydroxyl, or one, two, or three halogens), $R^aR^bN-$, $R^aR^bN-SO_2-$, $R^aR^bN-C(O)-$, $C_{1-6}$alkyl-C(O)$NR^a-$, $R^a-S(O)_w-$, $R^a-S(O)_w-NR^b-$ (wherein w is 0, 1, or 2), heteroaryl (optionally substituted by one, two, or three moieties independently selected from $R^c$), and heteroaryloxy;

$R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl;

or $R^a$ and $R^b$, when they occur together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle may optionally be substituted by one or more substituents selected from the group consisting of halogen, cyano, oxo, $C_{1-6}$alkyl, $C_{1-6}$haloalkyl, $-S(O)_w-C_{1-6}$alkyl (where w is 0, 1, or 2), hydroxyl, $-C(O)-C_{1-6}$alkyl, $-NH_2$, and $-NH-C(O)-C_{1-6}$alkyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{2-6}$alkynyl (optionally substituted by one, two, or three halogens), $C_{3-6}$cycloalkyl, $C_{1-6}$alkoxy (optionally substituted by one, two or three halogens), $R^aR^bN-$, $R^aR^bN-SO_2-$, $R^aR^bN-C(O)-$, $R^a-C(O)-NR^a-$, $R^a-C(O)-$, $R^a-S(O)_w-NR^b-$ (wherein w is 0, 1, or 2), and $R^a-S(O)_w-$ (wherein w is 0, 1, or 2);

$R^d$ is selected from the group consisting of: H, $C_{1-6}$alkyl (optionally substituted by one, two, or three halogens, or hydroxyl) and $R^aR^bN-C(O)-$;

$R^g$ is selected from the group consisting of: halogen, phenyl, phenyloxy, anilinyl, hydroxyl, cyano, $C_{1-6}$alkyl (optionally substituted by cyano, hydroxyl, or one, two, or three halogens), $C_{3-6}$cycloalkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$alkoxy (optionally substituted by cyano, hydroxyl, or one, two, or three halogens), $R^a-C(O)NR^a-$, $R^aR^bN-$, $R^aR^bN-SO_2-$, $R^a-S(O)_w-$ (wherein w is 0, 1, or 2), $R^a-SO_2-NR^b-$, $R^aR^bN-C(O)-$, heterocycle (optionally substituted by one, two, or three moieties each independently selected from $R^c$, and connected to $R^3$ or $R^5$ through a carbon or heteroatom), and heteroaryl (optionally substituted by one, two, or three moieties each independently selected from $R^c$, and connected to $R^3$ or $R^5$ through a carbon or heteroatom), or two adjacent $R^g$ groups, along with the carbons to which they are attached, can be taken together to form a 5- or 6-member heterocyclic or heteroaryl ring optionally substituted with 0, 1 or 2 halogens selected from F or Cl and which may have one or two additional heteroatoms selected from O, S, and N;

$R^h$ is selected from the group consisting of: halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$alkoxy (optionally substituted by cyano, hydroxyl, or one, two, or three halogens), $R^aR^bN-$, $R^a-C(O)NR^a-$, $R^aR^bN-SO_2-$, $R^aR^bN-C(O)-$, $R^a-S(O)_w-$ (wherein w is 0, 1, or 2), $R^a-SO_2-NR^b-$, heteroaryl (optionally substituted by one, two, or three moieties each independently selected from $R^c$, and connected to $R^7$ through a carbon or heteroatom), heterocycle (optionally substituted by one, two, or three moieties each independently selected from $R^c$, and connected to $R^7$ through a carbon or heteroatom), and heteroaryloxy (optionally substituted by one, two, or three moieties each independently selected from $R^c$), or two adjacent $R^h$ groups, along with the carbons to which they are attached, can be taken together to form a 5- or 6-member heterocyclic or heteroaryl ring optionally substituted with 0, 1 or 2 halogens selected from F or Cl and which may have one or two additional heteroatoms selected from O, S, and N;

or a pharmaceutically acceptable salt, solvate, hydrate, tautomer, or stereoisomer thereof.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (Ia):

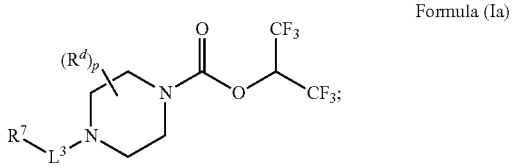

Formula (Ia)

wherein p is 0, 1, or 2;

$R^d$ is selected from the group consisting of: H and $C_{1-6}$alkyl;

$L^3$ is a bond, —$CH_2$—, —$S(O)_2$—, or —C(O)—;

$R^7$ is selected from the group consisting of: H, phenyl, naphthyl, mono or bicyclic heteroaryl, and mono or bicyclic heterocyclyl, wherein the heteroaryl or the heterocyclyl has 1, 2 or 3 heteroatoms independently selected from O, S, and N; wherein $R^7$ is optionally substituted by one, two, three, or four moieties independently selected from $R^h$;

$R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl; or $R^a$ and $R^b$, when they occur together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle may optionally be substituted by one or more substituents selected from the group consisting of halogen, cyano, oxo, $C_{1-6}$alkyl, $C_{1-6}$haloalkyl, —$S(O)_w$—$C_{1-6}$alkyl (where w is 0, 1, or 2), hydroxyl, —C(O)—$C_{1-6}$alkyl, —$NH_2$, and —NH—C(O)—$C_{1-6}$alkyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{2-6}$alkynyl (optionally substituted by one, two, or three halogens), $C_{3-6}$cycloalkyl, $C_{1-6}$alkoxy (optionally substituted by one, two, or three halogens), $R^aR^bN$—, $R^aR^bN$—$SO_2$—, $R^aR^bN$—C(O)—, $R^a$—C(O)—$NR^a$—, $R^a$—C(O)—, $R^a$—$S(O)_w$—$NR^b$— (wherein w is 0, 1, or 2), and $R^a$—$S(O)_w$— (wherein w is 0, 1, or 2); and $R^h$ is selected from the group consisting of: halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$ alkoxy (optionally substituted by cyano, hydroxyl, or one, two, or three halogens), $R^aR^bN$—, $R^a$—C(O)$NR^a$—, $R^aR^bN$—$SO_2$—, $R^aR^bN$—C(O)—, $R^a$—$S(O)_w$— (wherein w is 0, 1, or 2), $R^a$—$SO_2$—$NR^b$, heteroaryl (optionally substituted by one, two, or three moieties each independently selected from $R^c$, and connected to $R^7$ through a carbon or heteroatom), heterocycle (optionally substituted by one, two or three moieties each independently selected from $R^c$, and connected to $R^7$ through a carbon or heteroatom), and heteroaryloxy (optionally substituted by one, two, or three moieties each independently selected from $R^c$), or two adjacent $R^h$ groups, along with the carbons to which they are attached, can be taken together to form a 5- or 6-member heterocyclic or heteroaryl ring optionally substituted with 0, 1 or 2 halogens selected from F or Cl and which may have one or two additional heteroatoms selected from O, S, and N;

or a pharmaceutically acceptable salt, solvate, hydrate, tautomer, or stereoisomer thereof.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (Ib):

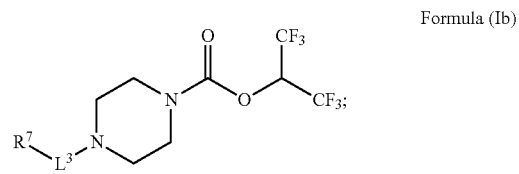

Formula (Ib)

wherein $L^3$ is a bond, —$CH_2$—, —$S(O)_2$—, or —C(O)—;

$R^7$ is phenyl; wherein $R^7$ is optionally substituted by one, two, or three moieties independently selected from $R^h$;

$R^a$ and $R^b$ are independently selected, for each occurrence, from the group consisting of hydrogen and $C_{1-3}$alkyl; wherein $C_{1-3}$alkyl is optionally substituted by one or more substituents selected from halogen, cyano, oxo, hydroxyl, heterocycle, and phenyl;

or $R^a$ and $R^b$, when they occur together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, $C_{1-6}$alkyl, $C_{1-6}$haloalkyl, —$S(O)_w$—$C_{1-6}$alkyl (where w is 0, 1, or 2), hydroxyl, —C(O)—$C_{1-6}$alkyl, —$NH_2$, and —NH—C(O)—$C_{1-6}$alkyl;

$R^c$ is selected from the group consisting of halogen, hydroxyl, $C_{1-6}$alkyl (optionally substituted by one, two, or three halogens), and $C_{1-6}$alkoxy (optionally substituted by one, two, or three halogens); and $R^h$ is selected from the group consisting of: halogen, phenyl (optionally substituted by one, two, or three moieties each independently selected from $R^c$), hydroxyl, cyano, $C_{1-6}$alkyl (optionally substituted by one, two, or three halogens), $C_{1-6}$alkoxy (optionally substituted by one, two, or three halogens), $R^aR^bN$—, $R^a$—C(O)$NR^a$—, $R^aR^bN$—$SO_2$—, $R^aR^bN$—C(O)—, $R^a$—$S(O)_w$— (wherein w is 0, 1, or 2), $R^a$—$SO_2$—$NR^b$—, and heteroaryl (optionally substituted by one, two, or three moieties each independently selected from $R^c$);

or a pharmaceutically acceptable salt, solvate, hydrate, tautomer, or stereoisomer thereof.

In some embodiments is a radiolabeled MGLL occupancy probe of Formula (I), (Ia), or (Ib), wherein $L^3$ is —$CH_2$—.

In some embodiments is a radiolabeled MGLL occupancy probe of Formula (I), (Ia), or (Ib), wherein $R^7$ is phenyl substituted by one, two, or three moieties independently selected from $R^h$. In some embodiments is a radiolabeled MGLL occupancy probe of Formula (I), (Ia), or (Ib), wherein $R^h$ is selected from the group consisting of halogen, phenyl (optionally substituted by one, two, or three moieties each independently selected from $R^c$), hydroxyl, cyano, $C_{1-6}$alkyl (optionally substituted by one, two, or three halogens), $C_{1-6}$alkoxy (optionally substituted by one, two, or three halogens), and $R^aR^bN$—. In some embodiments is a radiolabeled MGLL occupancy probe of Formula (I), (Ia), or (Ib), wherein $R^7$ is phenyl substituted by two moieties independently selected from $R^h$. In some embodiments is a radiolabeled MGLL occupancy probe of Formula (I), (Ia), or (Ib), wherein $R^h$ is halogen, $C_{1-6}$alkyl (optionally substituted by one, two, or three halogens), or $R^aR^bN$—. In some embodiments is a radiolabeled MGLL occupancy probe of Formula (I), (Ia), or (Ib), wherein $R^a$ and $R^b$, together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, $C_{1-6}$alkyl, $C_{1-6}$haloalkyl, —S(O), —$C_{1-6}$alkyl (where w is 0, 1, or 2), hydroxyl, —C(O)—$C_{1-6}$alkyl, —NH$_2$, and —NH—C(O)—$C_{1-6}$alkyl. In some embodiments is a radiolabeled MGLL occupancy probe of Formula (I), (Ia), or (Ib), wherein $R^a$ and $R^b$, together with the nitrogen to which they are attached, form a 4-6 membered saturated heterocyclic ring, which may have an additional heteroatom selected from O, S, and N, wherein the 4-6 membered saturated heterocyclic ring is optionally substituted by one or more substituents selected from the group consisting of halogen, cyano, oxo, $C_{1-6}$alkyl, $C_{1-6}$haloalkyl, —S(O)$_w$—$C_{1-6}$ alkyl (where w is 0, 1, or 2), hydroxyl, —C(O)—$C_{1-6}$alkyl, —NH$_2$, and —NH—C(O)—$C_{1-6}$alkyl. In some embodiments is a radiolabeled MGLL occupancy probe of Formula (I), (Ia), or (Ib), wherein $R^a$ and $R^b$, together with the nitrogen to which they are attached, form a 4-6 membered saturated heterocyclic ring, which may have an additional heteroatom selected from O, S, and N, wherein the 4-6 membered saturated heterocyclic ring is substituted by $C_{1-6}$haloalkyl. In some embodiments is a radiolabeled MGLL occupancy probe of Formula (I), (Ia), or (Ib), wherein the PET tracer radionuclide is $^{18}$F. In some embodiments is a radiolabeled MGLL occupancy probe of Formula (I), (Ia), or (Ib), wherein the PET tracer radionuclide is $^{15}$O. In some embodiments is a radiolabeled MGLL occupancy probe of Formula (I), (Ia), or (Ib), wherein the PET tracer radionuclide is $^{11}$C. In some embodiments is a radiolabeled MGLL occupancy probe of Formula (I), (Ia), or (Ib), wherein the radiolabeled MGLL occupancy probe forms a covalent adduct with the active-site serine in MGLL. In some embodiments the radiolabeled MGLL occupancy probe has the structure

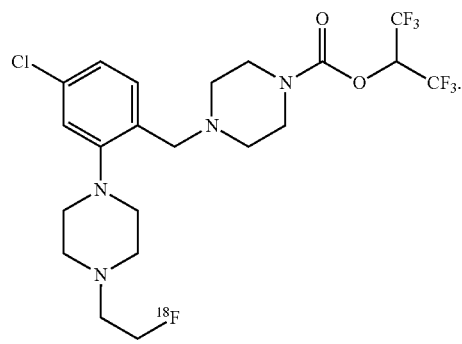

In another aspect is a method for assessing MGLL enzyme occupancy of a MGLL inhibitor in a mammal, comprising administering the MGLL inhibitor to the mammal, administering a radiolabeled MGLL occupancy probe described herein to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe described herein to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe in the brain of the mammal is measured.

In another aspect is a method for assessing tissue distribution of a MGLL inhibitor in a mammal, comprising administering a radiolabeled MGLL occupancy probe described herein to the mammal, and measuring the whole body biodistribution of the MGLL inhibitor by whole body PET imaging.

In another aspect is a method for labeling a MGLL enzyme comprising contacting tissues expressing the MGLL enzyme with a radiolabeled MGLL occupancy probe described herein.

In another aspect is a method for detecting a radiolabeled MGLL enzyme comprising contacting tissues expressing the MGLL enzyme with a radiolabeled MGLL occupancy probe described herein and detecting MGLL occupancy by PET imaging.

In another aspect is an inhibited, radiolabeled monoacylglycerol lipase comprising a radiolabeled MGLL occupancy probe described herein irreversibly and covalently bound to the active-site serine in MGLL.

In another aspect is a compound having the structure of Formula (V):

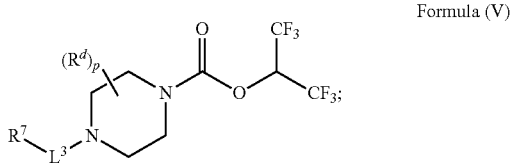

Formula (V)

wherein
p is 0, 1, or 2;
$R^d$ is H or $C_{1-6}$alkyl;
$L^3$ is a bond, —$CH_2$—, —$S(O)_2$—, or —$C(O)$—;
$R^7$ is phenyl substituted by $R^aR^bN$— and a moiety selected from the group consisting of: halogen and $C_{1-6}$alkyl (optionally substituted by one, two, or three halogens);
$R^a$ and $R^b$, together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle is substituted by $C_{1-6}$haloalkyl;
or a solvate, hydrate, tautomer, stereoisomer, or pharmaceutically acceptable salt thereof.

In some embodiments is a compound of Formula (V), wherein p is 0. In some embodiments is a compound of Formula (V), wherein $L^3$ is —$CH_2$—. In some embodiments is a compound of Formula (V), wherein $R^a$ and $R^b$, together with the nitrogen to which they are attached, form a 4-6 membered heterocyclic ring, which may have an additional heteroatom selected from O, S, and N; wherein the 4-6 membered heterocyclic ring is substituted by $C_{1-6}$haloalkyl. In some embodiments is a compound of Formula (V), wherein the 4-6 membered heterocyclic ring is piperazine. In some embodiments is a compound having the structure

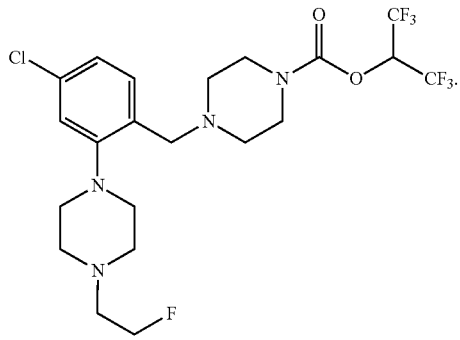 [SMILES: O=C(OC(C(F)(F)F)C(F)(F)F)N1CCN(Cc2ccc(Cl)cc2N2CCN(CCF)CC2)CC1]

DETAILED DESCRIPTION OF THE INVENTION

Figure 1:
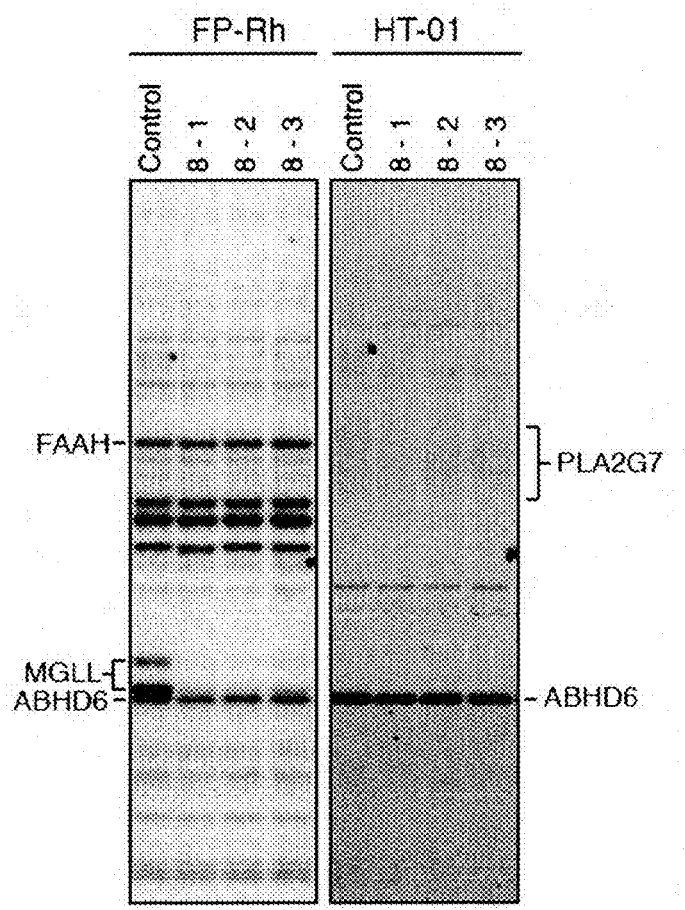
FIG. 1 shows MGLL target engagement and selectivity of a single oral dose of Compound 8 in the mouse brain by activity-based protein profiling (ABPP).

MGLL is an enzyme that catalyzes the hydrolysis of the endocannabinoid 2-AG, an endogenous ligand of the cannabinoid receptors $CB_1$ and $CB_2$, which are the molecular targets of the psychoactive component of Cannabis sativa, $\Delta^9$-tetrahydrocannabinol (THC). In rodents, MGLL is the major 2-AG hydrolase in the CNS as well as in most peripheral tissues and is the primary enzyme controlling the levels of 2-AG available to signal through $CB_1$ and $CB_2$.

$CB_1$ is the primary cannabinoid receptor in the nervous system and is widely distributed throughout the brain and at lower levels in peripheral tissue. Activation of $CB_1$ accounts for most of the neurobehavioral effects of THC and other exogenous cannabinoids (exocannabinoids) in rodents and human. $CB_2$ is expressed primarily on immune cells and mediates the immunosuppressive effects of exocannabinoids. Direct activation of cannabinoid receptors by Cannabis preparations (e.g., Sativex®), THC (e.g., Marinol®), and cannabinoid agonists (e.g., Cesamet®) elicits therapeutically beneficial effects on pain, spasticity, sleep, appetite, and nausea. However, these exocannabinoids cause motor and cognitive defects and carry abuse potential, limiting broad use. Amplifying the actions of endocannabinoids by inhibiting their enzymatic degradation has emerged as a therapeutic strategy with the potential to avoid the deleterious effects associated with exocannabinoids.

The efficacy of MGLL inhibitors has been established in preclinical models of pain and (neuro)inflammation. MGLL inhibitors produce anti-nociceptive and anti-inflammatory effects by reducing the hydrolysis of the endocannabinoid 2-AG, an endogenous ligand of the cannabinoid (CB) receptors, into arachidonic acid (AA) and glycerol. Increased 2-AG concentrations results in enhanced CB receptor signaling, while reduced AA levels results in suppression of pro-inflammatory prostanoid signaling. MGLL inhibitors have the potential to provide novel therapeutics for a number of clinical indications including neuropathic pain, neuroinflammation, and neurodegeneration. In order to evaluate the efficacy of novel inhibitors of MGLL, it is necessary to correlate doses and exposures of these novel inhibitors with the extent of MGLL target engagement. For therapeutic effects anticipated to be modulated primarily in the CNS, clinical evaluation of target occupancy requires the development of non-invasive quantitative techniques. The development of radiolabeled MGLL occupancy probes offers the potential for evaluating MGLL in conditions with neurobehavioral or neuroinflammatory changes, thus providing a means to better identify the role of MGLL in the pathology of these conditions in support of therapeutic drug development.

Definitions

As used in the specification and appended claims, unless specified to the contrary, the following terms have the meaning indicated below.

The singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term. "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "aryl" as used herein refers to a mono- or bicyclic carbocyclic ring system with 3-14 carbon atoms having one or two aromatic rings including, but not limited to, phenyl, naphthyl, tetrahydronaphthyl, indanyl, indenyl, and the like.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-7 carbon atoms, referred to herein as $C_{3-7}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-7, 3-6, or 4-6 carbons, referred to herein for example as $C_{3-7}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, oxadiazole, isothiazole, isoxazole, imidazole, indazole, pyrazole, quinoline, triazole, pyridine or pyrimidine etc.

The terms "heterocycle", "heterocyclyl", or "heterocyclic group" as used herein refers to saturated or partially unsaturated 4-7 membered ring structures or 8-10 membered bicyclic or spirocyclic ring structures, whose ring structures include one to three heteroatoms, such as nitrogen, oxygen, and sulfur. Where possible, heterocyclyl rings may be linked to the adjacent radical through carbon or nitrogen. A heterocycle may be fused to one or more aryl, or partially unsaturated, or saturated rings. Examples of heterocyclyl groups include, but are not limited to azetidine, benzodioxole, 2,8-diazaspiro[4.5]decan-1-one, 3,4-dihydro-2H-benzo[b][1,4]oxazinedihydrobenzofuran, dihydrofuran, dihydroisobenzofuran, 6,7-dihydro-5H-pyrrolo[3,4-b]pyridine, indoline, morpholine, octahydropyrrolo[1,2-a]pyrazine, 8-oxa-2-azaspiro[4.5]decane, oxetane, 2,3-dihydrobenzofuran, piperazine, piperidine, pyrrolidine, tetrahydrofuran, tetrahydropyran, thiomorpholine, etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Optional" or "optionally" means that a subsequently described event or circumstance may or may not occur and that the description includes instances when the event or circumstance occurs and instances in which it does not. For example, "optionally substituted aryl" means that the aryl radical is or is not be substituted and that the description includes both substituted aryl radicals and aryl radicals having no substitution.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

In some embodiments, "individual", "subject", and "patient" are used interchangeably and include any animal, including mammals, preferably mice, rats, other rodents, rabbits, dogs, cats, swine, cattle, sheep, horses, or primates, and most preferably humans. In some embodiments, "subject" refers to a healthy individual. In other embodiments, "subject" refers to a patient in need of treatment. In some embodiments, "subject" refers to a human or other mammal. In some embodiments, "subject" refers to a human. In some embodiments, "subject" refers to a non-human mammal.

A "subject group" has a sufficient number of subjects to provide a statistically significant average measurement of a relevant pharmacokinetic parameter.

In the present specification, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds decribed herein are administered in therapeutically effective amounts to treat a disease. Alternatively, a therapeutically effective amount of a compound is the quantity required to achieve a desired therapeutic and/or prophylactic effect.

The term "an MGLL inhibitor containing a positron emission tomography (PET) tracer radionuclide" means that one or more atoms of the MGLL inhibitor are replaced with a positron emission tomography (PET) tracer radionuclide. In some embodiments, a fluorine atom of the MGLL inhibitor is replaced by $^{18}F$. In some embodiments, a carbon atom of the MGLL inhibitor is replaced by $^{11}C$. In some embodiments, an oxygen atom of the MGLL inhibitor is replaced by $^{15}O$. In some embodiments a nitrogen atom of the MGLL inhibitor is replaced by $^{13}N$.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond or arrangement of substituents around a cycloalkyl or heterocyclic ring. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention embraces isotopically labeled compounds as disclosed herein. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the invention may have one or more H atoms replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound of this disclosure contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, α-amino($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O ($C_{1-6}$)alkyl)$_2$ or glycosyl (the radical resulting from the removal of a hydroxyl group of the hemiacetal form of a carbohydrate)

1,1,1,3,3,3-Hexafluoropropan-2-yl 4-(2-(pyrrolidin-1-yl)-4-(trifluoromethyl)benzyl)piperazine-1-carboxylate (Compound 9) is an irreversible inhibitor of MGLL. Alternate names include, but are not limited to, the following: 1-piperazinecarboxylic acid, 4-[[2-(1-pyrrolidinyl)-4-(trifluoromethyl)phenyl]methyl]-,2,2,2-trifluoro-1-(trifluoromethyl)ethyl ester; 1,1,1,3,3,3-hexafluoropropan-2-yl 4-{[2-(pyrrolidin-1-yl)-4-(trifluoromethyl) phenyl] methyl}piperazine-1-carboxylate; and 2,2,2-trifluoro-1-(trifluoromethyl)ethyl 4-{[2-(1-pyrrolidinyl)-4-(trifluoromethyl)phenyl]methyl}-1-piperazinecarboxylate. Compound 9 has the structure represented by:

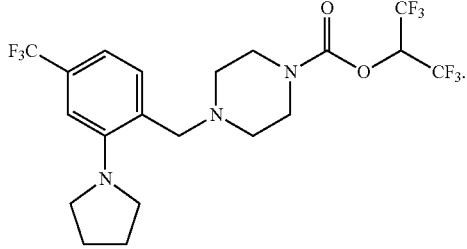

The preparation of Compound 9 is disclosed in US 2015/0148330, the content of which is incorporated by reference in its entirety.

In some embodiments, a pharmaceutically acceptable salt of Compound 9 is a hydrochloride salt. In further embodiments, the pharmaceutically acceptable salt of Compound 9 is a mono-hydrochloride salt.

In some embodiments, a fragment of Compound 9 is covalently attached to MGLL. In some embodiments, the fragment is:

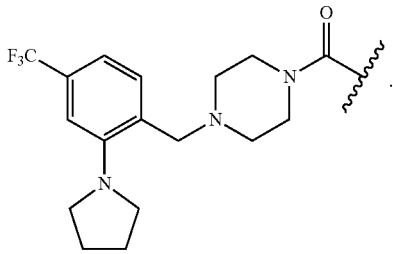 [SMILES: *C(=O)N1CCN(Cc2ccc(C(F)(F)F)cc2N2CCCC2)CC1]

Radiolabeled MGLL Occupancy Probes

In some embodiments described herein is a radiolabeled monoacylglycerol lipase (MGLL) occupancy probe comprising a MGLL inhibitor containing a positron emission tomography (PET) tracer radionuclide; wherein the PET tracer radionuclide is $^{18}F$, $^{15}O$, or $^{13}N$. In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{18}F$. In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{15}O$. In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{13}N$, In some embodiments is a radiolabeled monoacylglycerol lipase (MGLL) occupancy probe comprising a MGLL inhibitor containing a positron emission tomography (PET) tracer radionuclide; wherein the PET tracer radionuclide is $^{18}F$, $^{15}O$, or $^{13}N$; and the radiolabeled MGLL occupancy probe forms a covalent adduct with the active-site serine in MGLL.

In some embodiments described herein is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (I):

Formula (I)

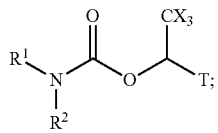

wherein
T is $CX_3$ or

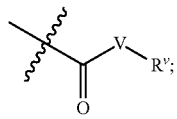

X is selected independently, for each occurrence, from H, F, Cl or Br; wherein at least three occurrences of X are F;
V is O or $NR^a$;
$R^V$ is selected from the group consisting of hydrogen, $C_1$-$C_6$alkyl, $C_2$-$C_6$alkenyl, $C_{3-6}$cycloalkyl, phenyl, heteroaryl, and heterocyclyl, or when $R^a$ and $R^v$ occur together with the nitrogen to which they are attached, form a 4-6 membered heterocyclic ring which may have an additional heteroatom selected from O, S, and N; wherein $C_1$-$C_6$alkyl, $C_2$-$C_6$alkenyl, phenyl, heterocyclic ring and heterocyclyl are optionally substituted by one, two, or three moieties independently selected from the group consisting of halogen, hydroxyl, $C_1$-$C_6$alkyl, cyano, and phenyl; and
wherein
a)
$R_1$ and $R_2$ taken together with the nitrogen to which they are attached form a moiety selected from:
a 4-7 membered heterocyclic ring B having an additional nitrogen; or
a 4-7 membered heterocyclic ring A;
wherein one carbon of ring A has a substituent represented by:

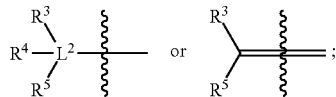

$L^2$ is $C_1$-$C_6$alkylene or $C_1$-$C_6$alkylene-$NR^a$—;
$R^3$ and $R^5$ are each independently selected from phenyl, naphthyl, a mono or bicyclic heteroaryl and a mono or bicyclic heterocycle, wherein the heterocycle or heteroaryl has 1, 2 or 3 heteroatoms independently selected from O, S, and N; and wherein $R^3$ and $R^5$ may be independently and optionally substituted by one, two, three, or four moieties each independently selected from $R^g$;

$R^4$ is selected from the group consisting of H, halogen, hydroxyl, cyano, and $C_1$-$C_5$alkoxy;

A is optionally substituted on another carbon by one, two, three, or four substituents each independently selected from $R^d$;

the additional nitrogen of ring B has a substituent represented by:

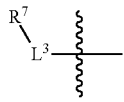

$L^3$ is selected from the group consisting of: a bond, $C_1$-$C_6$alkylene, —C(O)—, $C_1$-$C_6$alkylene-C(O)—, C(O)—$C_1$-$C_6$alkylene-, $NR^a$—C(O)—$C_1$-$C_6$alkylene-, $C_1$-$C_6$alkylene-O—C(O)—, —S(O)$_w$—, and $C_1$-$C_6$alkylene-S(O)$_w$—, wherein w is 0, 1, or 2, and wherein $C_1$-$C_6$alkylene is optionally substituted by one or two substituents selected from the group consisting of: halogen, hydroxyl, cyano, and an additional $R^7$, wherein when $L^3$ is —S(O)$_w$—, then $R^7$ is not H;

$R^7$ is selected from the group consisting of: H, phenyl, naphthyl, mono or bicyclic heteroaryl, and mono or bicyclic heterocyclyl, wherein the heteroaryl or the heterocyclyl has 1, 2 or 3 heteroatoms independently selected from O, S, and N; wherein $R^7$ is optionally substituted by one, two, three, or four moieties independently selected from $R^h$;

B is optionally substituted on one or more carbons by one, two, three, or four moieties each independently selected from $R^d$;

or b)

$R^1$ is -$L^1$-$R^6$;

$R^2$ is H or $C_1$-$C_6$alkyl;

$L^1$ is $C_1$-$C_6$alkylene or a bond;

$R^6$ is selected from the group consisting of phenyl, naphthyl, a mono or bicyclic heteroaryl, and a mono or bicyclic heterocycle, wherein the heteroaryl or heterocycle has 1, 2 or 3 heteroatoms independently selected from O, S, and N; and $R^6$ is optionally substituted by one, two, three, or four moieties independently selected from the group consisting of: halogen, phenyl (optionally substituted by one, two, or three moieties independently selected from $R^c$), phenyloxy (optionally substituted by one, two, or three moieties independently selected from $R^c$), anilinyl (optionally substituted on a carbon by one, two or three moieties independently selected from $R^c$), hydroxyl, cyano, $C_{1-6}$alkyl (optionally substituted by cyano, hydroxyl, or one, two, or three halogens), $C_{1-6}$alkoxy (optionally substituted by cyano, hydroxyl, or one, two, or three halogens), $R^aR^bN$—, $R^aR^bN$—$SO_2$—, $R^aR^bN$—C(O)—, $C_{1-6}$alkyl-C(O)$NR^a$—, $R^a$—S(O)$_w$—, $R^a$—S(O)$_w$—$NR^b$— (wherein w is 0, 1, or 2), heteroaryl (optionally substituted by one, two, or three moieties independently selected from $R^c$), and heteroaryloxy;

$R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl; or $R^a$ and $R^b$, when they occur together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle may optionally be substituted by one or more substituents selected from the group consisting of halogen, cyano, oxo, $C_{1-6}$alkyl, $C_{1-6}$haloalkyl, —S(O)$_w$—$C_{1-6}$alkyl (where w is 0, 1, or 2), hydroxyl, —C(O)—$C_{1-6}$alkyl, —$NH_2$, and —NH—C(O)—$C_{1-6}$alkyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{2-6}$alkynyl (optionally substituted by one, two, or three halogens), $C_{3-6}$cycloalkyl, $C_{1-6}$alkoxy (optionally substituted by one, two, or three halogens), $R^aR^bN$—, $R^aR^bN$—$SO_2$—, $R^aR^bN$—C(O)—, $R^a$—C(O)—$NR^a$—, $R^a$—C(O)—, $R^a$—S(O)$_w$—$NR^b$— (wherein w is 0, 1, or 2), and $R^a$—S(O)$_w$— (wherein w is 0, 1, or 2);

$R^d$ is selected from the group consisting of: H, $C_{1-6}$alkyl (optionally substituted by one, two, or three halogens, or hydroxyl) and $R^aR^bN$—C(O)—;

$R^g$ is selected from the group consisting of: halogen, phenyl, phenyloxy, anilinyl, hydroxyl, cyano, $C_{1-6}$alkyl (optionally substituted by cyano, hydroxyl, or one, two, or three halogens), $C_{3-6}$cycloalkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$alkoxy (optionally substituted by cyano, hydroxyl, or one, two, or three halogens), $R^a$—C(O)$NR^a$—, $R^aR^bN$—, $R^aR^bN$—$SO_2$—, $R^a$—S(O)$_w$— (wherein w is 0, 1, or 2), $R^a$—$SO_2$—$NR^b$—, $R^aR^bN$—C(O)—, heterocycle (optionally substituted by one, two, or three moieties each independently selected from $R^c$, and connected to $R^3$ or $R^5$ through a carbon or heteroatom), and heteroaryl (optionally substituted by one, two, or three moieties each independently selected from $R^c$, and connected to $R^3$ or $R^5$ through a carbon or heteroatom), or two adjacent $R^g$ groups, along with the carbons to which they are attached, can be taken together to form a 5- or 6-member heterocyclic or heteroaryl ring optionally substituted with 0, 1 or 2 halogens selected from F or Cl and which may have one or two additional heteroatoms selected from O, S, and N;

$R^h$ is selected from the group consisting of: halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by cyano, hydroxyl, or one, two, or three halogens), $C_{2-6}$alkenyl (optionally substituted by cyano, hydroxyl, or one, two, or three halogens), $C_{2-6}$ alkynyl (optionally substituted by cyano, hydroxyl, or one, two, or three halogens), $C_{1-6}$alkoxy (optionally substituted by cyano, hydroxyl, or one, two, or three halogens), $R^aR^bN$—, $R^a$—C(O)$NR^a$—, $R^aR^bN$—$SO_2$—, $R^aR^bN$—C(O)—, $R^a$—S(O)$_w$— (wherein w is 0, 1, or 2), $R^a$—$SO_2$—$NR^b$—, heteroaryl (optionally substituted by one, two, or three moieties each independently selected from $R^c$, and connected to $R^7$ through a carbon or heteroatom), heterocycle (optionally substituted by one, two, or three moieties each independently selected from $R^c$, and connected to $R^7$ through a carbon or heteroatom), and heteroaryloxy (optionally substituted by one, two, or three moieties each independently selected from $R^c$), or two adjacent $R^h$ groups, along with the carbons to which they are attached, can be taken together to form a 5- or 6-member heterocyclic or heteroaryl ring optionally substituted with 0, 1 or 2 halogens selected from F or Cl and which may have one or two additional heteroatoms selected from O, S, and N;

or a pharmaceutically acceptable salt, solvate, hydrate, tautomer, or stereoisomer thereof.

In some embodiments is a radiolabeled MGLL occupancy probe of Formula (I), wherein $R_1$ and $R_2$ taken together with the nitrogen to which they are attached form a moiety selected from a 4-7 membered heterocyclic ring B having an additional nitrogen and a 4-7 membered heterocyclic ring A. In some embodiments is a radiolabeled MGLL occupancy probe of Formula (I), wherein $R_1$ and $R_2$ taken together with the nitrogen to which they are attached form a 4-7 membered heterocyclic ring B having an additional nitrogen. In some embodiments is a radiolabeled MGLL occupancy probe of Formula (I), wherein T is $CX_3$. In some embodiments is a radiolabeled MGLL occupancy probe of Formula (I), wherein T is $CF_3$. In some embodiments of the radiolabeled MGLL occupancy probe of Formula (I), wherein $L^3$ is a bond, $C_{1-6}$alkyl, —S(O)$_2$—, or —C(O)—. In some embodiments of the radiolabeled MGLL occupancy probe of Formula (I), wherein $L^3$ is $C_{1-6}$alkyl. In some embodiments of the radiolabeled MGLL occupancy probe of Formula (I), wherein $L^3$ is —CH$_2$—. In some embodiments is a radiolabeled MGLL occupancy probe of Formula (I), wherein $R^7$ is phenyl substituted by one, two, or three moieties independently selected from $R^h$. In some embodiments is a radiolabeled MGLL occupancy probe of Formula (I), wherein $R^h$ is selected from the group consisting of halogen, phenyl (optionally substituted by one, two, or three moieties each independently selected from $R^c$), hydroxyl, cyano, $C_{1-6}$alkyl (optionally substituted by one, two, or three halogens), $C_{1-6}$alkoxy (optionally substituted by one, two, or three halogens), and $R^aR^bN$—. In some embodiments is a radiolabeled MGLL occupancy probe of Formula (I), wherein $R^7$ is phenyl substituted by two moieties independently selected from $R^h$. In some embodiments is a radiolabeled MGLL occupancy probe of Formula (I), wherein $R^h$ is halogen, $C_{1-6}$alkyl (optionally substituted by one, two, or three halogens), or $R^aR^bN$—. In some embodiments is a radiolabeled MGLL occupancy probe of Formula (I), wherein $R^a$ and $R^b$, together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, $C_{1-6}$alkyl, $C_{1-6}$haloalkyl, —S(O)$_w$—$C_{1-6}$alkyl (where w is 0, 1, or 2), hydroxyl, —C(O)—$C_{1-6}$alkyl, —NH$_2$, and —NH—C(O)—$C_{1-6}$alkyl. In some embodiments is a radiolabeled MGLL occupancy probe of Formula (I), wherein $R^a$ and $R^b$, together with the nitrogen to which they are attached, form a 4-6 membered saturated heterocyclic ring, which may have an additional heteroatom selected from O, S, and N, wherein the 4-6 membered saturated heterocyclic ring is optionally substituted by one or more substituents selected from the group consisting of halogen, cyano, oxo, $C_{1-6}$alkyl, $C_{1-6}$haloalkyl, —S(O)$_w$— $C_{1-6}$alkyl (where w is 0, 1, or 2), hydroxyl, —C(O)—$C_{1-6}$alkyl, —NH$_2$, and —NH—C(O)—$C_{1-6}$alkyl. In some embodiments is a radiolabeled MGLL occupancy probe of Formula (I), wherein $R^a$ and $R^b$, together with the nitrogen to which they are attached, form a 4-6 membered saturated heterocyclic ring, which may have an additional heteroatom selected from O, S, and N, wherein the 4-6 membered saturated heterocyclic ring is substituted by $C_{1-6}$haloalkyl. In some embodiments is a radiolabeled MGLL occupancy probe of Formula (I), wherein the PET tracer radionuclide is $^{18}$F. In some embodiments is a radiolabeled MGLL occupancy probe of Formula (I), wherein the PET tracer radionuclide is $^{15}$O. In some embodiments is a radiolabeled MGLL occupancy probe of Formula (I), wherein the PET tracer radionuclide is $^{13}$N. In some embodiments is a radiolabeled MGLL occupancy probe of Formula (I), wherein the PET tracer radionuclide is $^{11}$C. In some embodiments is a radiolabeled MULL occupancy probe of Formula (I), wherein the radiolabeled MGLL occupancy probe forms a covalent adduct with the active-site serine in MGLL.

In some embodiments is a radiolabeled monoacylglycerol lipase (MGLL) occupancy probe, comprising an MGLL Inhibitor containing a positron emission tomography (PET) tracer radionuclide, wherein the MGLL inhibitor has the structure of Formula (Ia):

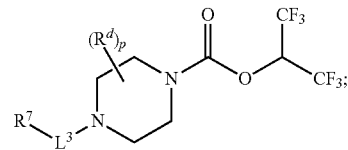

Formula (Ia)

wherein p is 0, 1, or 2;

$R^d$ is selected from the group consisting of: H and $C_{1-6}$alkyl;

$L^3$ is a bond, —CH$_2$—, —S(O)$_2$—, or —C(O)—;

$R^7$ is selected from the group consisting of: H, phenyl, naphthyl, mono or bicyclic heteroaryl, and mono or bicyclic heterocyclyl, wherein the heteroaryl or the heterocyclyl has 1, 2 or 3 heteroatoms independently selected from O, S, and N; wherein $R^7$ is optionally substituted by one, two, three, or four moieties independently selected from $R^h$;

$R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl; or $R^a$ and $R^b$, when they occur together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle may optionally be substituted by one or more substituents selected from the group consisting of halogen, cyano, oxo, $C_{1-6}$alkyl, $C_{1-6}$haloalkyl, —S(O)$_w$—$C_{1-6}$alkyl (where w is 0, 1, or 2), hydroxyl, —C(O)—$C_{1-6}$alkyl, —NH$_2$, and —NH—C(O)—$C_{1-6}$alkyl;

$R^c$ is selected from the group consisting of halogen, cyano, hydroxyl, nitro, $C_{1-6}$alkyl (optionally substituted by one, two, or three halogens, cyano, or hydroxyl), C$_{2-6}$alkenyl (optionally substituted by one, two, or three halogens), C$_{2-6}$alkynyl (optionally substituted by one, two, or three halogens), C$_{3-6}$cycloalkyl, C$_{1-6}$alkoxy (optionally substituted by one, two, or three halogens), R$^a$R$^b$N—, R$^a$R$^b$N—SO$_2$—, R$^a$R$^b$N—C(O)—, R$^a$—C(O)—NR$^a$—, R$^a$—C(O)—, R$^a$—S(O)$_w$—NR$^b$— (wherein w is 0, 1, or 2), and R$^a$—S(O)$_w$— (wherein w is 0, 1, or 2); and R$^h$ is selected from the group consisting of: halogen, phenyl (optionally substituted by one, two, or three moieties each independently selected from R$^c$), phenyloxy (optionally substituted by one, two, or three moieties each independently selected from R$^c$), hydroxyl, cyano, C$_{1-6}$alkyl (optionally substituted by cyano, hydroxyl, or one, two, or three halogens), C$_{2-6}$alkenyl (optionally substituted by cyano, hydroxyl, or one, two, or three halogens), C$_{2-6}$alkynyl (optionally substituted by cyano, hydroxyl, or one, two, or three halogens), C$_{1-6}$alkoxy (optionally substituted by cyano, hydroxyl, or one, two, or three halogens), R$^a$R$^b$N—, R$^a$—C(O)NR$^a$—, R$^a$R$^b$N—SO$_2$—, R$^a$R$^b$N—C(O)—, R$^a$—S(O)$_w$— (wherein w is 0, 1, or 2), R$^a$—SO$_2$—NR$^b$—, heteroaryl (optionally substituted by one, two, or three moieties each independently selected from R$^c$, and connected to R$^7$ through a carbon or heteroatom), heterocycle (optionally substituted by one, two, or three moieties each independently selected from R$^c$, and connected to R$^7$ through a carbon or heteroatom), and heteroaryloxy (optionally substituted by one, two, or three moieties each independently selected from R$^c$), or two adjacent R$^h$ groups, along with the carbons to which they are attached, can be taken together to form a 5- or 6-member heterocyclic or heteroaryl ring optionally substituted with 0, 1 or 2 halogens selected from F or Cl and which may have one or two additional heteroatoms selected from O, S, and N;

or a pharmaceutically acceptable salt, solvate, hydrate, tautomer, or stereoisomer thereof.

In some embodiments of the radiolabeled MGLL occupancy probe of Formula (Ia), wherein p is 0. In some embodiments of the radiolabeled MGLL occupancy probe of Formula (Ia), wherein L$^3$ is —CH$_2$—. In some embodiments is a radiolabeled MGLL occupancy probe of Formula (Ia), wherein R$^7$ is phenyl substituted by one, two, or three moieties independently selected from R$^h$. In some embodiments is a radiolabeled MGLL occupancy probe of Formula (Ia), wherein R$^h$ is selected from the group consisting of halogen, phenyl (optionally substituted by one, two, or three moieties each independently selected from R$^c$), hydroxyl, cyano, C$_{1-6}$alkyl (optionally substituted by one, two, or three halogens), C$_{1-6}$alkoxy (optionally substituted by one, two, or three halogens), and R$^a$R$^b$N—. In some embodiments is a radiolabeled MGLL occupancy probe of Formula (Ia), wherein R$^7$ is phenyl substituted by two moieties independently selected from R$^h$. In some embodiments is a radiolabeled MGLL occupancy probe of Formula (Ia), wherein R$^h$ is halogen, C$_{1-6}$alkyl (optionally substituted by one, two, or three halogens), or R$^a$R$^b$N—. In some embodiments is a radiolabeled MGLL occupancy probe of Formula (Ia), wherein R$^a$ and R$^b$, together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, C$_{1-6}$alkyl, C$_{1-6}$haloalkyl, —S(O)$_w$—C$_{1-6}$alkyl (where w is 0, 1, or 2), hydroxyl, —C(O)—C$_{1-6}$alkyl, —NH$_2$, and —NH—C(O)—C$_{1-6}$alkyl. In some embodiments is a radiolabeled MGLL occupancy probe of Formula (Ia), wherein R$^a$ and R$^b$, together with the nitrogen to which they are attached, form a 4-6 membered saturated heterocyclic ring, which may have an additional heteroatom selected from O, S, and N, wherein the 4-6 membered saturated heterocyclic ring is optionally substituted by one or more substituents selected from the group consisting of halogen, cyano, oxo, C$_{1-6}$alkyl, C$_{1-6}$haloalkyl, —S(O)$_w$—C$_{1-6}$alkyl (where w is 0, 1, or 2), hydroxyl, —C(O)—C$_{1-6}$alkyl, —NH$_2$, and —NH—C(O)—C$_{1-6}$alkyl. In some embodiments is a radiolabeled MGLL occupancy probe of Formula (Ia), wherein R$^a$ and R$^b$, together with the nitrogen to which they are attached, form a 4-6 membered saturated heterocyclic ring, which may have an additional heteroatom selected from O, S, and N, wherein the 4-6 membered saturated heterocyclic ring is substituted by C$_{1-6}$haloalkyl. In some embodiments is a radiolabeled MGLL occupancy probe of Formula (Ia), wherein the PET tracer radionuclide is $^{18}$F. In some embodiments is a radiolabeled MGLL occupancy probe of Formula (Ia), wherein the PET tracer radionuclide is $^{15}$O. In some embodiments is a radiolabeled MGLL occupancy probe of Formula (Ia), wherein the PET tracer radionuclide is $^{13}$N. In some embodiments is a radiolabeled MGLL occupancy probe of Formula (Ia), wherein the PET tracer radionuclide is $^{11}$C. In some embodiments is a radiolabeled MGLL occupancy probe of Formula (Ia), wherein the radiolabeled MGLL occupancy probe forms a covalent adduct with the active-site serine in MGLL.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (Ib):

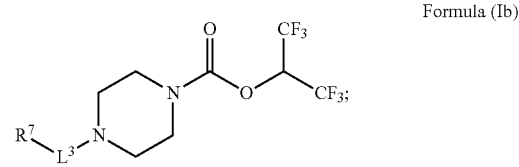

Formula (Ib)

wherein
L$^3$ is a bond, —CH$_2$—, —S(O)$_2$—, or —C(O)—;
R$^7$ is phenyl; wherein R$^7$ is optionally substituted by one, two, or three moieties independently selected from R$^h$;
R$^a$ and R$^b$ are independently selected, for each occurrence, from the group consisting of hydrogen and C$_{1-3}$alkyl; wherein C$_{1-3}$alkyl is optionally substituted by one or more substituents selected from halogen, cyano, oxo, hydroxyl, heterocycle, and phenyl;
or R$^a$ and R$^b$, when they occur together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, C$_{1-6}$alkyl, C$_{1-6}$haloalkyl, —S(O)$_w$—C$_{1-}$ $_6$alkyl (where w is 0, 1, or 2), hydroxyl, —C(O)—C$_{1-6}$alkyl, —NH$_2$, and —NH—C(O)—C$_{1-6}$alkyl;

R$^c$ is selected from the group consisting of halogen, hydroxyl, C$_{1-6}$alkyl (optionally substituted by one, two, or three halogens), and C$_{1-6}$alkoxy (optionally substituted by one, two, or three halogens); and R$^h$ is selected from the group consisting of: halogen, phenyl (optionally substituted by one, two, or three moieties each independently selected from R$^c$), hydroxyl, cyano, C$_{1-6}$alkyl (optionally substituted by one, two, or three halogens), C$_{1-6}$alkoxy (optionally substituted by one, two, or three halogens), R$^a$R$^b$N—, R$^a$—C(O)NR$^a$—, R$^a$R$^b$N—SO$_2$—, R$^a$R$^b$N—C(O)—, R$^a$—S(O)$_w$— (wherein w is 0, 1, or 2), R$^a$—SO$_2$—NR$^b$—, and heteroaryl (optionally substituted by one, two, or three moieties each independently selected from R$^c$);

or a pharmaceutically acceptable salt, solvate, hydrate, tautomer, or stereoisomer thereof.

In some embodiments of the radiolabeled MGLL occupancy probe of Formula (Ib), wherein L$^3$ is —CH$_2$—. In some embodiments is a radiolabeled MGLL occupancy probe of Formula (Ib), wherein R$^h$ is selected from the group consisting of halogen, phenyl (optionally substituted by one, two, or three moieties each independently selected from R$^c$), hydroxyl, cyano, C$_{1-6}$alkyl (optionally substituted by one, two, or three halogens), C$_{1-6}$alkoxy (optionally substituted by one, two, or three halogens), and R$^a$R$^b$N—. In some embodiments is a radiolabeled MGLL occupancy probe of Formula (Ib), wherein R$^7$ is phenyl substituted by two moieties independently selected from R$^h$. In some embodiments is a radiolabeled MGLL occupancy probe of Formula (Ib), wherein R$^h$ is halogen, C$_{1-6}$alkyl (optionally substituted by one, two, or three halogens), or R$^a$R$^b$N—. In some embodiments is a radiolabeled MGLL occupancy probe of Formula (Ib), wherein R$^a$ and R$^b$, together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, C$_{1-6}$alkyl, C$_{1-6}$haloalkyl, —S(O)$_w$—C$_{1-6}$alkyl (where w is 0, 1, or 2), hydroxyl, —C(O)—C$_{1-6}$alkyl, —NH$_2$, and —NH—C(O)—C$_{1-6}$alkyl. In some embodiments is a radiolabeled MGLL occupancy probe of Formula (Ib), wherein R$^a$ and R$^b$, together with the nitrogen to which they are attached, form a 4-6 membered saturated heterocyclic ring, which may have an additional heteroatom selected from O, S, and N, wherein the 4-6 membered saturated heterocyclic ring is optionally substituted by one or more substituents selected from the group consisting of halogen, cyano, oxo, C$_{1-6}$alkyl, C$_{1-6}$haloalkyl, —S(O)$_w$—C$_{1-6}$alkyl (where w is 0, 1, or 2), hydroxyl, —C(O)—C$_{1-6}$alkyl, —NH$_2$, and —NH—C(O)—C$_{1-6}$alkyl. In some embodiments is a radiolabeled MGLL occupancy probe of Formula (Ib), wherein R$^a$ and R$^b$, together with the nitrogen to which they are attached, form a 4-6 membered saturated heterocyclic ring, which may have an additional heteroatom selected from O, S, and N, wherein the 4-6 membered saturated heterocyclic ring is substituted by C$_{1-6}$haloalkyl. In some embodiments is a radiolabeled MGLL occupancy probe of Formula (Ib), wherein the PET tracer radionuclide is $^{18}$F. In some embodiments is a radiolabeled MGLL occupancy probe of Formula (Ib), wherein the PET tracer occupancy radionuclide is $^{15}$O. In some embodiments is a radiolabeled MGLL occupancy probe of Formula (Ib), wherein the PET tracer radionuclide is $^{13}$N. In some embodiments is a radiolabeled MGLL occupancy probe of Formula (Ib), wherein the PET tracer radionuclide is $^{11}$C. In some embodiments is a radiolabeled MGLL occupancy probe of Formula (Ib), wherein the radiolabeled MGLL occupancy probe forms a covalent adduct with the active-site serine in MGLL.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (II):

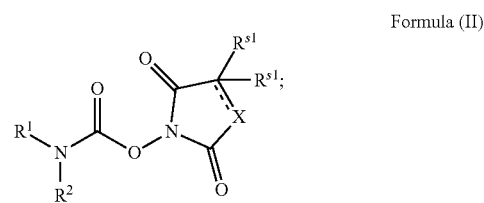

Formula (II)

wherein

X is CR$^{s1}$, CR$^{s1}$R$^{s1}$, or NR$^a$;

⚡ is a double or single bond;

R$^{s1}$ is independently selected for each occurrence from the group consisting of H, halogen, cyano, hydroxyl, nitro, phenyl (optionally substituted by one, two, or three substituents each independently selected from R$^c$), C$_{1-6}$alkyl (optionally substituted by one, two, or three halogens, cyano, phenyl, or hydroxyl), C$_{1-6}$alkoxy (optionally substituted by one, two, or three halogens, cyano, or hydroxyl), C$_{1-6}$alkenyl and C$_{1-6}$alkynyl; or two R$^{s1}$ moieties on separate carbons, taken together, form a fused ring selected from the group consisting of a phenyl and a 5-6 membered cycloalkyl or heterocycle, wherein the fused ring is optionally substituted by one or two substituents selected from R$^c$, wherein a) R$_1$ and R$_2$ taken together with the nitrogen to which they are attached form a moiety selected from:

a monocyclic 5-7 membered heterocyclic ring B having one additional heteroatom independently selected from N, or S; or a monocyclic 4-7 membered heterocyclic ring A;

wherein one carbon of ring A has an optional substituent selected from the group consisting of:

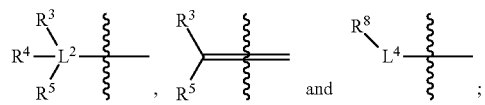

L$^2$ is C$_1$-C$_6$alkylene or C$_1$-C$_6$alkylene-NR$^a$—;

R$^3$ and R$^5$ are each independently selected from phenyl, naphthyl, or a mono or bicyclic heterocycle or heteroaryl having 1, 2 or 3 heteroatoms independently selected from O, S, and N; and wherein R$^3$ and R$^5$ may be independently and optionally substituted by one, two, or three moieties each independently selected from R$^g$;

R$^4$ is selected from the group consisting of H, halogen, hydroxyl, cyano, and C$_1$-C$_5$alkoxy;

L$^4$ is selected from the group consisting of: a bond, C$_1$-C$_6$alkylene, —C$_2$-C$_6$alkenylene-, —O—, —O—C$_1$-C$_6$alkylene-, —NR$^b$—, —C(O)—, C$_1$-C$_6$alkylene-C(O)—, —C$_0$-C$_6$alkylene-NR$^b$—C(O)—, —C$_0$-C$_6$alkylene-NR$^b$—S(O)$_w$—, —NR$^b$—C(O)—NR$^b$—C$_0$-C$_6$alkylene-, —C$_0$-C$_6$alkylene-O—C(O)—, —S(O)$_w$—, and C$_1$-C$_6$alkylene-S(O)$_w$—, wherein w is 0, 1, or 2, and wherein C$_1$-C$_6$alkylene is optionally substituted by one or two substituents selected from the group consisting of: halogen, hydroxyl, cyano, C$_{3-6}$cycloalkyl, and R$^8$, or L$^4$ is absent;

R$^8$ is selected from the group consisting of: H, hydroxyl, halogen, R$^a$R$^b$N—, C$_1$-C$_6$alkyl, phenyl, naphthyl, heterocycle, or mono or bicyclic heteroaryl having 1, 2 or 3 heteroatoms independently selected from O, S, and N; wherein R$^8$ is optionally substituted by one, two, or three moieties independently selected from the group consisting of halogen, phenyl (optionally substituted by one, two, or three moieties each independently selected from R$^c$), phenyloxy (optionally substituted by one, two, or three moieties each independently selected from R$^c$), hydroxyl, cyano, C$_{1-6}$alkyl (optionally substituted by cyano, hydroxyl, or one, two, or three halogens), C$_{2-6}$alkenyl (optionally substituted by cyano, hydroxyl, or one, two, or three halogens), C$_{1-6}$alkoxy (optionally substituted by cyano, hydroxyl, or one, two, or three halogens), R$^a$R$^b$N—, R$^a$—C(O)NR$^a$—, R$^a$R$^b$N—SO$_2$—, R$^a$R$^b$N-carbonyl-, R$^a$—S(O)$_w$— (wherein w is 0, 1, or 2), R$^a$—S(O)$_w$—NR$^b$— (wherein w is 0, 1, or 2), oxo, heterocycle (optionally substituted by one, two, or three moieties each independently selected from R$^c$), heteroaryl (optionally substituted by one, two, or three moieties each independently selected from R$^c$) or heteroaryloxy (optionally substituted by one, two, or three moieties each independently selected from R$^r$);

A is optionally substituted on another carbon by one, two, three, or four substituents each independently selected from R$^d$;

the additional heteroatom of ring B, when N, has an optional substituent represented by:

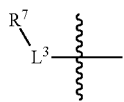

L$^3$ is selected from the group consisting of: a bond, C$_1$-C$_6$alkylene, C$_2$-C$_6$alkenylene, —C(O)—, —C(O)—O, C$_1$-C$_6$alkylene-C(O)—, C(O)—C$_1$-C$_6$alkylene-, C$_1$-C$_6$alkylene-O—C(O)—, —C$_0$-C$_6$alkylene-C(O)—NR$^a$, C$_0$-C$_6$alkylene-NR$^b$—S(O)$_w$—, —S(O)$_w$—, and C$_1$-C$_6$alkylene-S(O)$_w$—, wherein w is 0, 1, or 2, and wherein C$_1$-C$_6$alkylene is optionally substituted by one or two substituents selected from the group consisting of: halogen, hydroxyl, cyano, and an additional R$^7$, wherein when L$^3$ is —S(O)$_w$—, then R$^7$ is not H;

R$^7$ is selected from the group consisting of: H, hydroxyl, halogen, C$_1$-C$_{10}$alkyl, C$_2$-C$_{10}$alkynyl, C$_2$-C$_{10}$alkenyl, C$_3$-C$_{10}$cycloalkyl, phenyl, naphthyl, mono or bicyclic heterocyclyl, and mono or bicyclic heteroaryl, wherein the heteroaryl or the heterocyclyl has 1, 2 or 3 heteroatoms independently selected from O, S, and N; wherein R$^7$ is optionally substituted by one, two, three, or four moieties independently selected from R$^h$;

B is optionally substituted on one or more carbons by one, two, three, or four moieties each independently selected from R$^d$;

or b) R$_1$ is -L$^1$-R$^6$;

R$^2$ is H or C$_1$-C$_6$alkyl;

L$^1$ is C$_1$-C$_{10}$alkylene or a bond;

R$^6$ is selected from the group consisting of: C$_2$-C$_{10}$alkynyl, C$_2$-C$_{10}$alkenyl, phenyl, naphthyl, tetrahydronaphthalenyl, mono or bicyclic heterocycle or mono or bicyclic heteroaryl, wherein the heteroaryl or heterocycle has 1, 2 or 3 heteroatoms independently selected from O, S, and N; and wherein R$^6$ is optionally substituted by one, two, three, or four moieties independently selected from the group consisting of: halogen, phenyl (optionally substituted by one, two, or three moieties independently selected from R$^c$), phenyloxy (optionally substituted by one, two, or three moieties independently selected from R$^c$), anilinyl (optionally substituted on a carbon by one, two or three moieties independently selected from R$^c$), hydroxyl, cyano, C$_{1-6}$alkyl (optionally substituted by cyano, hydroxyl, or one, two, or three halogens), C$_{1-6}$alkoxy (optionally substituted by cyano, hydroxyl, or one, two, or three halogens), R$^a$R$^b$N—, R$^a$R$^b$N—SO$_2$—, R$^a$R$^b$N-carbonyl-, —COOH, C$_{0-6}$alkyl-C(O)NR$^a$—, R$^a$—S(O)$_w$—, R$^a$—S(O)$_w$—NR$^b$— (wherein w is 0, 1, or 2), heteroaryl (optionally substituted by one, two, or three moieties independently selected from R$^c$), heteroaryloxy (optionally substituted by one, two, or three moieties independently selected from R$^c$), or a 4-7 membered heterocyclic ring (optionally substituted by one, two, or three moieties independently selected from R$^c$);

R$^a$ and R$^b$ may be independently selected, for each occurrence, from the group consisting of hydrogen, C$_{1-3}$alkyl, and phenyl; wherein C$_{1-3}$alkyl may optionally be substituted by one or more substituents selected from halogen, cyano, oxo, phenyl, heterocycle and hydroxyl, and wherein phenyl or heterocycle is optionally substituted by one, two, or three moieties each independently selected from R$^c$;

or R$^a$ and R$^b$, when they occur together with the nitrogen to which they are attached, form a 4-6 membered heterocyclic ring, a 9-10 membered bicyclic heterocycle or spirocyclic ring, or a 7-9 membered bridged ring, which may have an additional heteroatom selected from O, S, and N; wherein the 4-6 membered heterocyclic ring, 9-10 membered bicyclic heterocycle or spirocycle, or the 7-9 membered bridged ring may optionally be substituted by one or more substituents selected from the group consisting of halogen, cyano, oxo, C$_{1-6}$alkyl, —S(O)$_w$—C$_{1-6}$alkyl (where w is 0, 1, or 2), hydroxyl, —C(O)—C$_{1-6}$alkyl, —NH$_2$, —NH—C$_{1-6}$alkyl, —NH—C(O)—C$_{1-6}$alkyl, —NH—S(O)$_w$—C$_{1-6}$alkyl (where w is 0, 1, or 2) and —C(O)-heterocycle;

R$^c$ is selected from the group consisting of halogen, cyano, hydroxyl, nitro, C$_{1-6}$alkyl (optionally substituted by one, two, or three halogens, cyano, or hydroxyl), C$_{2-6}$alkenyl (optionally substituted by one, two, or three halogens), C$_{3-6}$cycloalkyl, C$_{1-6}$alkoxy (optionally substituted by one, two, or three halogens), oxo, R$^a$R$^b$N—, R$^a$R$^b$N—SO$_w$— (wherein w is 0, 1, or 2), R$^a$R$^b$N-carbonyl-, C$_{1-6}$alkyl-C(O)—, C$_{1-6}$alkyl-O—C(O)—, R$^a$—S(O)$_w$—NR$^b$— (wherein w is 0, 1, or 2), and R$^a$—S(O)$_w$— (wherein w is 0, 1, or 2);

R$^d$ is selected from the group consisting of consisting of: H, C$_{1-6}$alkyl (optionally substituted by one, two, or three halogens, or hydroxyl) and R$^a$R$^b$N—C(O)—;

$R^g$ is selected from the group consisting of: halogen, phenyl, phenyloxy, anilinyl, hydroxyl, cyano, $C_{1-6}$alkyl (optionally substituted by cyano, hydroxyl, or one, two, or three halogens), $C_{3-6}$ cycloalkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$alkoxy (optionally substituted by cyano, hydroxyl, or one, two, or three halogens), $R^a$—C(O)NR$^a$—, oxo, $R^aR^bN$—, $R^aR^bN$—SO$_2$—, $R^a$—S(O)$_w$— (wherein w is 0, 1, or 2), $R^a$—SO$_2$—NR$^b$—, oxo, $R^aR^bN$—C(O)—, heterocycle (optionally substituted by one, two, or three moieties each independently selected from $R^c$, and connected to $R^3$ or $R^5$ through a carbon or heteroatom), and heteroaryl (optionally substituted by one, two, or three moieties each independently selected from $R^c$, and connected to $R^3$ or $R^5$ through a carbon or heteroatom), or two adjacent $R^9$ groups, along with the carbons to which they are attached, can be taken together to form a 5- or 6-member mono or bicyclic heterocyclic or mono or bicyclic heteroaryl ring optionally substituted with 0, 1 or 2 halogens selected from F or Cl and which may have one or two additional heteroatoms selected from O, S, and N;

$R^h$ is selected from the group consisting of: halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by cyano, hydroxyl, or one, two, or three halogens), $C_{3-6}$cycloalkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$alkoxy (optionally substituted by cyano, hydroxyl, or one, two, or three halogens), $R^aR^bN$—, $R^a$—C(O)NR$^a$—, $R^aR^bN$—S(O)$_w$— (wherein w is 0, 1, or 2), $R^aR^bN$—C(O)—, $R^a$—S(O)$_w$— (wherein w is 0, 1, or 2), $R^a$—SO$_w$—NR$^b$— (wherein w is 0, 1, or 2), $C_{1-6}$alkyl-O—C(O)—, $C_{1-6}$alkyl-C(O)—, $R^a$—S(O)$_w$— (wherein w is 0, 1, or 2), heteroaryl (optionally substituted by one, two, or three moieties each independently selected from $R^c$, and connected to $R^7$ through a carbon or heteroatom), heterocycle (optionally substituted by one, two, or three moieties each independently selected from $R^c$, and connected to $R^7$ through a carbon or heteroatom), and heteroaryloxy (optionally substituted by one, two, or three moieties each independently selected from $R^c$), or two adjacent $R^h$ groups, along with the carbons to which they are attached, can be taken together to form a 5- or 6-member mono or bicyclic heterocyclic or mono or bicyclic heteroaryl ring optionally substituted with 0, 1 or 2 halogens selected from F or Cl and which may have one or two additional heteroatoms selected from O, S, and N;

or a pharmaceutically acceptable salt or stereoisomer thereof.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (IIa):

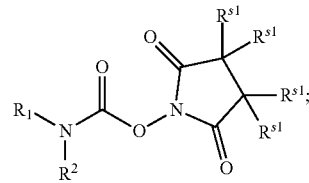

Formula (IIa)

wherein $R^{s1}$ is independently selected for each occurrence from the group consisting of H, halogen, cyano, hydroxyl, nitro, phenyl (optionally substituted by one, two, or three substituents each independently selected from $R^c$), $C_{1-6}$alkyl (optionally substituted by one, two, or three halogens, cyano, phenyl, or hydroxyl), $C_{1-6}$alkoxy (optionally substituted by one, two, or three halogens, cyano, or hydroxyl), $C_{1-6}$alkenyl and $C_{1-6}$alkynyl;

$R_1$ and $R_2$ taken together with the nitrogen to which they are attached form a monocyclic 5-7 membered heterocyclic ring B having one additional heteroatom independently selected from N, or S; and the additional heteroatom of ring B, when N, is substituted by:

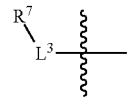

$L^3$ is selected from the group consisting of: a bond, $C_1$-$C_6$alkylene, $C_2$-$C_6$alkenylene, —C(O)—, —C(O)—O, —C$_1$-C$_6$alkylene-C(O)—, —C(O)—C$_1$-C$_6$alkylene-, C$_1$-C$_6$alkylene-O—C(O)—, —C$_0$-C$_6$alkylene-C(O)—NR$^a$, —C$_0$-C$_6$alkylene-NR$^b$—S(O)$_w$—, —S(O)$_w$—, and —C$_1$-C$_6$alkylene-S(O)$_w$—, wherein w is 0, 1, or 2, and wherein $C_1$-$C_6$alkylene is optionally substituted by one or two substituents selected from the group consisting of: halogen, hydroxyl, cyano, and an additional $R^7$, wherein when $L^3$ is —S(O)$_w$—, then $R^7$ is not H;

$R^7$ is selected from the group consisting of: H, hydroxyl, halogen, $C_1$-$C_{10}$alkyl, $C_2$-$C_{10}$alkynyl, $C_2$-$C_{10}$alkenyl, $C_3$-$C_{10}$cycloalkyl, phenyl, naphthyl, mono or bicyclic heterocyclyl, and mono or bicyclic heteroaryl, wherein the heteroaryl or the heterocyclyl has 1, 2 or 3 heteroatoms independently selected from O, S, and N; wherein $R^7$ is optionally substituted by one, two, three, or four moieties independently selected from $R^h$;

B is optionally substituted on one or more carbons by one, two, three, or four moieties each independently selected from $R^d$;

$R^a$ and $R^b$ are independently selected, for each occurrence, from the group consisting of hydrogen, $C_{1-3}$alkyl, and phenyl; wherein $C_{1-3}$alkyl may optionally be substituted by one or more substituents selected from halogen, cyano, oxo, phenyl, heterocycle and hydroxyl, and wherein phenyl or heterocycle is optionally substituted by one, two, or three moieties each independently selected from $R^c$;

or $R^a$ and $R^b$, when they occur together with the nitrogen to which they are attached, form a 4-6 membered heterocyclic ring, a 9-10 membered bicyclic heterocycle or spirocyclic ring, or a 7-9 membered bridged ring, which may have an additional heteroatom selected from O, S, and N; wherein the 4-6 membered heterocyclic ring, 9-10 membered bicyclic heterocycle or spirocycle, or the 7-9 membered bridged ring is optionally substituted by one or more substituents selected from the group consisting of halogen, cyano, oxo, $C_{1-6}$alkyl, —S(O)$_w$—$C_{1-6}$alkyl (where w is 0, 1, or 2), hydroxyl, —C(O)—$C_{1-6}$alkyl, —NH$_2$, —NH—$C_{1-6}$alkyl, —NH—C(O)—$C_{1-6}$alkyl, —NH—S(O)$_w$—$C_{1-6}$alkyl (where w is 0, 1, or 2) and —C(O)-heterocycle;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), oxo, $R^aR^bN$—, $R^aR^bN$—SO$_w$— (wherein w is 0, 1, or 2), $R^aR^bN$-carbonyl-, $C_{1-6}$alkyl-C(O)—, $C_{1-6}$alkyl-O—C(O)—, $R^a$—S(O)$_w$—NR$^b$— (wherein w is 0, 1, or 2), and $R^a$—S(O)$_w$— (wherein w is 0, 1, or 2);

$R^d$ is selected from the group consisting of consisting of: $C_{1-6}$alkyl (optionally substituted by one, two, or three halogens, or hydroxyl) and $R^aR^bN$—C(O)—; and $R^h$ is selected from the group consisting of: halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by cyano, hydroxyl, or one, two, or three halogens), $C_{3-6}$cycloalkyl (optionally substituted by cyano, hydroxyl, or one, two, or three halogens), $C_{2-6}$alkenyl (optionally substituted by cyano, hydroxyl, or one, two, or three halogens), $C_{2-6}$alkynyl (optionally substituted by cyano, hydroxyl, or one, two, or three halogens), $C_{1-6}$alkoxy (optionally substituted by cyano, hydroxyl, or one, two, or three halogens), $R^aR^bN$—, $R^a$—C(O)NR$^a$—, $R^aR^bN$—S(O)$_w$— (wherein w is 0, 1, or 2), $R^aR^bN$—C(O)—, $R^a$—S(O)$_w$— (wherein w is 0, 1, or 2), $R^a$—SO$_w$—NR$^b$— (wherein w is 0, 1, or 2), $C_{1-6}$alkyl-O—C(O)—, $C_{1-6}$alkyl-C(O)—, $R^a$—S(O)$_w$— (wherein w is 0, 1, or 2), heteroaryl (optionally substituted by one, two, or three moieties each independently selected from $R^c$, and connected to $R^7$ through a carbon or heteroatom), heterocycle (optionally substituted by one, two, or three moieties each independently selected from $R^c$, and connected to $R^7$ through a carbon or heteroatom) and heteroaryloxy (optionally substituted by one, two, or three moieties each independently selected from $R^e$), or two adjacent $R^h$ groups, along with the carbons to which they are attached, can be taken together to form a 5- or 6-member mono or bicyclic heterocyclic or mono or bicyclic heteroaryl ring optionally substituted with 0, 1 or 2 halogens selected from F or Cl and which may have one or two additional heteroatoms selected from O, S, and N;

or a pharmaceutically acceptable salt or stereoisomer thereof.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (III):

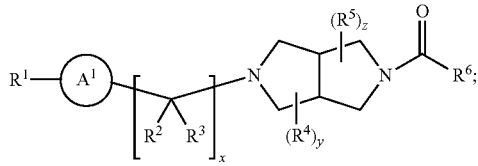

Formula (III)

wherein, $A^1$ is arylene or heteroarylene, each of which is optionally substituted with 1 or 2 substituents independently selected from the group consisting of halogen, alkyl, haloalkyl, cycloalkyl, hydroxyl, alkoxy, haloalkoxy, and -alkylene-cycloalkyl;

$R^1$ is one of the following:
  (a) heterocycloalkyl optionally substituted with 1, 2, or 3 substituents independently selected from the group consisting of alkyl, cycloalkyl, —N(R$^7$)C(O)R$^8$, —N(R$^7$)SO$_2$R$^8$, —C(O)R$^8$, —C(O)N(R$^9$)(R$^{10}$), —SO$_2$R$^8$, oxo, heteroaryl, halogen, haloalkyl, hydroxyl, alkoxyl, and -alkylene-cycloalkyl;
  (b) aryl, heteroaryl, a fused heterocyclyl-heteroaryl, or cycloalkyl, each of which is optionally substituted with 1, 2, or 3 substituents independently selected from the group consisting of halogen, —N(R$^7$)C(O)R$^8$, —N(R$^7$)SO$_2$R$^8$, —C(O)R$^8$, —C(O)N(R$^9$)(R$^1$), —SO$_2$R$^8$, heterocycloalkyl, alkyl, haloalkyl, cycloalkyl, hydroxyl, and alkoxy; or
  (c) alkyl, alkoxy, halogen, —C(O)N(R$^9$)(R$^{10}$), or -alkylene-heterocycloalkyl optionally substituted with 1 or more substituents independently selected from the group consisting of alkyl, cycloalkyl, —N(R$^7$)C(O)R$^8$, —N(R$^7$)SO$_2$R$^8$, —C(O)R$^8$, —C(O)N(R$^9$)(R$^{10}$), —SO$_2$R$^8$, oxo, heteroaryl, halogen, haloalkyl, hydroxyl, alkoxyl, and -alkylene-cycloalkyl;

$R^2$ is independently for each occurrence hydrogen or an alkyl optionally substituted with 1, 2, or 3 substituents independently selected from the group consisting of halogen, alkyl, haloalkyl, and cycloalkyl;

$R^3$ is independently for each occurrence hydrogen, or $R^3$ is independently for each occurrence alkyl or aryl, each of which is optionally substituted with 1, 2, or 3 substituents independently selected from the group consisting of halogen, alkyl, haloalkyl, and cycloalkyl;

$R^4$ and $R^5$ each represent independently for each occurrence alkyl, haloalkyl, or oxo;

$R^6$ is one of the following:
  (a) —O-haloalkyl or —O—C(R$^{11}$)(haloalkyl)C(O)N(R$^{12}$)(R$^{13}$);

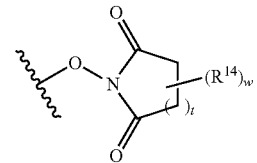

(b) wherein t is 1 or 2; w is 0, 1, 2, 3, or 4; and $R^{14}$ represents independently for each occurrence one of the following:
    (i) alkyl optionally substituted by 1, 2, or 3 substituents independently selected from the group consisting of halogen, cyano, phenyl, and hydroxyl;
    (ii) alkoxy optionally substituted by 1, 2, or 3 substituents independently selected from the group consisting of halogen, cyano, and hydroxyl;
    (iii) cycloalkyl optionally substituted by 1, 2, or 3 substituents independently selected from the group consisting of alkyl, halogen, cyano, phenyl, and hydroxyl; or
    (iv) phenyl optionally substituted by 1, 2, or 3 substituents independently selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), $(R^a)(R^b)N—$, $(R^a)(R^b)N—SO_2—$, $(R^a)(R^b)N—C(O)—$, $C_{1-6}$alkyl-C(O)—, $C_{1-6}$alkyl-O—C(O)—, $R^a—S(O)_2—N(R^b)—$, $R^a—S(O)—$, and $R^a—S(O)_2—$; wherein $R^a$ and $R^b$ each represent independently for each occurrence hydrogen, $C_{1-3}$alkyl, or phenyl; wherein $C_{1-3}$alkyl is optionally substituted by one or more substituents independently selected from the group consisting of halogen, cyano, oxo, phenyl, heterocyclyl and hydroxyl, and wherein phenyl or heterocyclyl is optionally substituted by one, two or three substituents each independently selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), oxo, amino, sulfonamide, amide, $C_{1-6}$alkyl-C(O)—, and $C_{1-6}$alkyl-O—C(O)—; or $R^a$ and $R^b$ are taken together with the nitrogen atom to which they are attached to form a 4-6 membered heterocyclic ring, a 9-10 membered bicyclic heterocycle or spirocyclic ring, or a 7-9 membered bridged ring, which in addition to the first heteroatom may have a second heteroatom selected from O, S, and N; wherein the 4-6 membered heterocyclic ring, 9-10 membered bicyclic heterocycle or spirocycle, or the 7-9 membered bridged ring is optionally substituted by one or more substituents independently selected from the group consisting of halogen, cyano, oxo, $C_{1-6}$alkyl, $—S(O)_2—C_{1-6}$alkyl, hydroxyl, $—C(O)—C_{1-6}$alkyl, $—NH_2$, $—N(H)—C_{1-6}$alkyl, $—N(H)—C(O)—C_{1-6}$alkyl, $—N(H)—S(O)_2—C_{1-6}$alkyl, and $—C(O)$-heterocycle; or

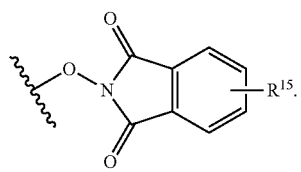

(c) where $R^{15}$ is hydrogen, alkyl, or halogen;
$R^7$ is hydrogen or alkyl;
$R^8$ is alkyl, cycloalkyl, or -alkylene-cycloalkyl,
$R^9$ is hydrogen or alkyl;
$R^{10}$ is hydrogen, alkyl, cycloalkyl, heterocycloalkyl, aryl, aralkyl, -alkylene-heterocycloalkyl, or -alkylene-cycloalkyl, wherein alkyl, cycloalkyl, heterocycloalkyl, aryl, aralkyl, -alkylene-heterocycloalkyl, and -alkylene-cycloalkyl are optionally substituted with 1 or more substituents selected from the group consisting of alkyl, alkenyl, alkynyl, alkoxyl, hydroxyl, halogen, and haloalkyl; or $R^9$ and $R^{10}$ are taken together with the nitrogen atom to which they are attached to form a 4-7 membered heterocyclic ring optionally substituted with 1 or more substituents selected from the group consisting of -alkyl, alkoxyl, hydroxyl, haloalkyl, halogen, $—N(R^7)C(O)R^8$, $—N(R^7)SO_2R^8$, $—C(O)R^8$, $—C(O)N(R^9)(R^{10})$, $—SO_2R^8$, and oxo;
$R^{11}$ is hydrogen or alkyl;
$R^{12}$ is hydrogen, alkyl, cycloalkyl, -alkylene-cycloalkyl, or aralkyl;
$R^{13}$ is alkyl, cycloalkyl, -alkylene-cycloalkyl, or aralkyl; or $R^{12}$ and $R^{13}$ are taken together with the nitrogen atom to which they are attached to form a 4-7 membered heterocyclic ring;
x is 1, 2, or 3; and
y and z are independently 0, 1, 2, 3, or 4;
or a pharmaceutically acceptable salt, solvate, hydrate, tautomer, or N-oxide thereof.

In some embodiments is a radiolabeled monoacylglycerol lipase (MGLL) occupancy probe, comprising an MGLL inhibitor containing a positron emission tomography (PET) tracer radionuclide, wherein the MGLL inhibitor has the structure of Formula (IV):

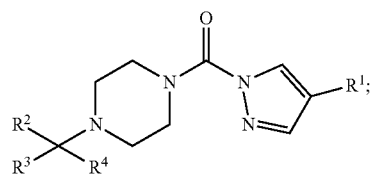

Formula (IV)

wherein:
$R^1$ is H, $—CF_3$, $C_{1-4}$ alkyl, cyano, halo, optionally substituted phenyl, $—CO_2R^5$, or $—C(O)NR^6R^7$;
$R^2$ is optionally substituted aryl, optionally substituted heteroaryl, or optionally substituted $C_{3-8}$ cycloalkyl;
$R^3$ is H;
$R^4$ is H or optionally substituted phenyl;
$R^5$ is H or $C_{1-4}$ alkyl; and
$R^6$ and $R^7$ are each independently H, $C_{1-4}$ alkyl, or $C_{3-8}$ cycloalkyl; or $R^6$ and $R^7$ together with the nitrogen to which they are attached form a 4-, 5-, 6-, 7-, or 8-member heterocyclyl ring, optionally containing another heteroatom selected from S or O;

or a solvate, hydrate, tautomer, N-oxide, or pharmaceutically acceptable salt thereof.

In some embodiments described herein is a radiolabeled monoacylglycerol lipase (MGLL) occupancy probe comprising a MGLL inhibitor containing a positron emission tomography (PET) tracer radionuclide; wherein the MGLL inhibitor is selected from a compound disclosed in WO 2012/054721, WO 2012/054716, US 2012/0077797, WO 2012/030907, WO 2010/124122, WO 2010/124121, WO 2010/124114, WO 2010/124082, WO 2010/124086, WO 2010/124119, WO 2010/124102, WO 2010/124108, WO 2010/124116, WO 2010/124112, or WO 2011/151808, each of which is incorporated herein by reference.

In some embodiments described herein is a radiolabeled monoacylglycerol lipase (MGLL) occupancy probe comprising a MGLL inhibitor containing a positron emission tomography (PET) tracer radionuclide; wherein the MGLL inhibitor is selected from a compound disclosed in US 2015/0148330, WO 2013142307, WO 2015003002, or WO 2015179559, each of which is incorporated herein by reference.

Compounds

The compounds of Formula (V) described herein are inhibitors of MGLL. The compounds of Formula (V) described herein, and compositions comprising these compounds, are useful for the treatment of pain, multiple sclerosis, Alzheimer's disease, and/or inflammatory bowel disease.

In one aspect is a compound of Formula (V):

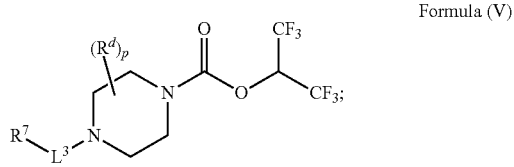

Formula (V)

wherein
p is 0, 1, or 2;
$R^d$ is H or $C_{1-6}$alkyl;
$L^3$ is a bond, —$CH_2$—, —$S(O)_2$—, or —$C(O)$—;
$R^7$ is phenyl substituted by $R^aR^bN$— and a moiety selected from the group consisting of: halogen and $C_{1-6}$alkyl (optionally substituted by one, two, or three halogens);
$R^a$ and $R^b$, together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle is substituted by $C_{1-6}$ haloalkyl;
or a solvate, hydrate, tautomer, stereoisomer, or pharmaceutically acceptable salt thereof.

In some embodiments is a compound of Formula (V), wherein p is 0. In some embodiments is a compound of Formula (V), wherein p is 1 and $R^d$ is $C_{1-6}$alkyl. In some embodiments is a compound of Formula (V), wherein p is 1 and $R^d$ is —$CH_3$. In some embodiments is a compound of Formula (V), wherein p is 2 and $R^d$ is $C_{1-6}$alkyl. In some embodiments is a compound of Formula (V), wherein p is 2 and $R^d$ is —$CH_3$. In some embodiments is a compound of Formula (V), wherein p is 2.

In some embodiments is a compound of Formula (V), wherein $L^3$ is a bond. In some embodiments is a compound of Formula (V), wherein $L^3$ is —$CH_2$—. In some embodiments is a compound of Formula (V), wherein $L^3$ is —$S(O)_2$—. In some embodiments is a compound of Formula (V), wherein $L^3$ is —$C(O)$—.

In some embodiments is a compound of Formula (V), wherein $R^7$ is phenyl substituted by $R^aR^bN$— and a halogen. In some embodiments is a compound of Formula (V), wherein $R^7$ is phenyl substituted by $R^aR^bN$— and a $C_{1-6}$alkyl (optionally substituted by one, two, or three halogens). In some embodiments is a compound of Formula (V), wherein $R^7$ is phenyl substituted by $R^aR^bN$— and —$CH_3$. In some embodiments is a compound of Formula (V), wherein $R^7$ is phenyl substituted by $R^aR^bN$— and —$CF_3$.

In some embodiments is a compound of Formula (V), wherein $R^a$ and $R^b$, together with the nitrogen to which they are attached, form a 4-6 membered heterocyclic ring, which may have an additional heteroatom selected from O, S, and N; wherein the 4-6 membered heterocyclic ring is substituted by $C_{1-6}$haloalkyl. In some embodiments is a compound of Formula (V), wherein $R^a$ and $R^h$, together with the nitrogen to which they are attached, form a 4-6 membered heterocyclic ring, which has an additional heteroatom selected from O, S, and N; wherein the 4-6 membered heterocyclic ring is substituted by $C_{1-6}$haloalkyl. In some embodiments is a compound of Formula (V), wherein $R^a$ and $R^b$, together with the nitrogen to which they are attached, form a piperazine ring substituted by $C_{1-6}$haloalkyl.

In some embodiments is a compound of Formula (V), wherein p is 0, $L^3$ is —$CH_2$—, $R^7$ is phenyl substituted by $R^aR^bN$— and a halogen, and $R^a$ and $R^b$, together with the nitrogen to which they are attached, form a piperazine ring substituted by $C_{1-6}$haloalkyl. In some embodiments is a compound of Formula (V) having the structure

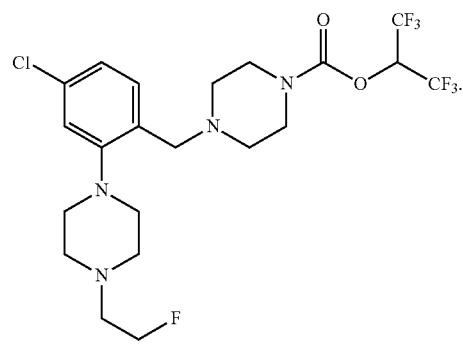 [SMILES: O=C(OC(C(F)(F)F)C(F)(F)F)N1CCN(Cc2ccc(Cl)cc2N2CCN(CCF)CC2)CC1]

Methods

In some embodiments is a method for assessing MGLL enzyme occupancy of a MGLL inhibitor in a mammal, comprising administering the MGLL inhibitor to the mammal, administering a radiolabeled MGLL occupancy probe of Formula (I) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (I) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (I) in the brain of the mammal is measured.

In some embodiments is a method for assessing tissue distribution of a MGLL inhibitor in a mammal, comprising administering a radiolabeled MGLL occupancy probe of Formula (I) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (I).

In some embodiments is a method for detecting a radiolabeled MGLL enzyme comprising contacting tissues expressing the MGLL enzyme with a radiolabeled MGLL occupancy probe of Formula (I) and detecting MGLL occupancy by PET imaging.

In some embodiments is an inhibited, radiolabeled monoacylglycerol lipase comprising a radiolabeled MGLL occupancy probe of Formula (I) irreversibly and covalently bound to the active-site serine in MGLL. In some embodiments, the inhibited, radiolabeled monoacylglycerol lipase comprising a radiolabeled MGLL occupancy probe of Formula (I) covalently attached to MGLL has the structure:

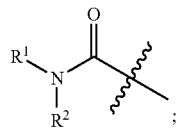

wherein ∤ represents the attachment of the radiolabeled MGLL occupancy probe of Formula (I) to the MGLL enzyme.

In some embodiments is a method for assessing MGLL enzyme occupancy of a MGLL inhibitor in a mammal, comprising administering the MGLL inhibitor to the mammal, administering a radiolabeled MGLL occupancy probe of Formula (Ia) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (Ia) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (Ia) in the brain of the mammal is measured.

In some embodiments is a method for assessing tissue distribution of a MGLL inhibitor in a mammal, comprising administering a radiolabeled MGLL occupancy probe of Formula (Ia) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (Ia).

In some embodiments is a method for detecting a radiolabeled MGLL enzyme comprising contacting tissues expressing the MGLL enzyme with a radiolabeled MGLL occupancy probe of Formula (Ia) and detecting MGLL occupancy by PET imaging.

In some embodiments is an inhibited, radiolabeled monoacylglycerol lipase comprising a radiolabeled MGLL occupancy probe of Formula (Ia) irreversibly and covalently bound to the active-site serine in MGLL. In some embodiments, the inhibited, radiolabeled monoacylglycerol lipase comprising a radiolabeled MGLL occupancy probe of Formula (Ia) covalently attached to MGLL has the structure:

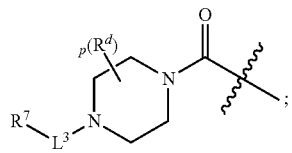

wherein ∤ represents the attachment of the radiolabeled MGLL occupancy probe of Formula (Ia) to the MGLL enzyme.

In some embodiments is a method for assessing MGLL enzyme occupancy of a MGLL inhibitor in a mammal, comprising administering the MGLL inhibitor to the mammal, administering a radiolabeled MGLL occupancy probe of Formula (Ib) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (Ib) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (Ib) in the brain of the mammal is measured.

In some embodiments is a method for assessing tissue distribution of a MGLL inhibitor in a mammal, comprising administering a radiolabeled MGLL occupancy probe of Formula (Ib) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (Ib).

In some embodiments is a method for detecting a radiolabeled MGLL enzyme comprising contacting tissues expressing the MGLL enzyme with a radiolabeled MGLL occupancy probe of Formula (Ib) and detecting MGLL occupancy by PET imaging.

In some embodiments is an inhibited, radiolabeled monoacylglycerol lipase comprising a radiolabeled MGLL occupancy probe of Formula (Ib) irreversibly and covalently bound to the active-site serine in MGLL. In some embodiments, the inhibited, radiolabeled monoacylglycerol lipase comprising a radiolabeled MGLL occupancy probe of Formula (Ib) covalently attached to MGLL has the structure:

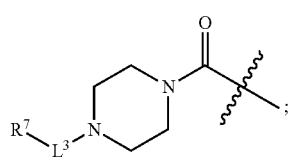

wherein ⁄ represents the attachment of the radiolabeled MGLL occupancy probe of Formula (Ib) to the MGLL enzyme.

In some embodiments is a method for assessing MGLL enzyme occupancy of a MGLL inhibitor in a mammal, comprising administering the MGLL inhibitor to the mammal, administering a radiolabeled MGLL occupancy probe of Formula (II) to the mammal; measuring the MGLL enzyme occupancy of the radiolabeled MGLL occupancy probe in the mammal, and comparing the MGLL enzyme occupancy of the radiolabeled MULL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (II) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (II) in the brain of the mammal is measured.

In some embodiments is a method for assessing tissue distribution of a MGLL inhibitor in a mammal, comprising administering a radiolabeled MGLL occupancy probe of Formula (II) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (II).

In some embodiments is a method for detecting a radiolabeled MGLL enzyme comprising contacting tissues expressing the MGLL enzyme with a radiolabeled MGLL occupancy probe of Formula (II) and detecting MGLL occupancy by PET imaging.

In some embodiments is an inhibited, radiolabeled monoacylglycerol lipase comprising a radiolabeled MGLL occupancy probe of Formula (II) irreversibly and covalently bound to the active-site serine in MGLL. In some embodiments, the inhibited, radiolabeled monoacylglycerol lipase comprising a radiolabeled MGLL occupancy probe of Formula (II) covalently attached to MGLL has the structure:

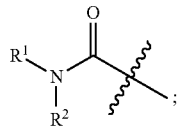

wherein ⁄ represents the attachment of the radiolabeled MGLL occupancy probe of Formula (II) to the MGLL enzyme.

In some embodiments is a method for assessing MGLL enzyme occupancy of a MGLL inhibitor in a mammal, comprising administering the MGLL inhibitor to the mammal, administering a radiolabeled MGLL occupancy probe of Formula (IIa) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (IIa) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (IIa) in the brain of the mammal is measured.

In some embodiments is a method for assessing tissue distribution of a MGLL inhibitor in a mammal, comprising administering a radiolabeled MGLL occupancy probe of Formula (IIa) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (IIa).

In some embodiments is a method for detecting a radiolabeled MGLL enzyme comprising contacting tissues expressing the MGLL enzyme with a radiolabeled MGLL occupancy probe of Formula (IIa) and detecting MGLL occupancy by PET imaging.

In some embodiments is an inhibited, radiolabeled monoacylglycerol lipase comprising a radiolabeled MGLL occupancy probe of Formula (IIa) irreversibly and covalently bound to the active-site serine in MGLL. In some embodiments, the inhibited, radiolabeled monoacylglycerol lipase comprising a radiolabeled MGLL occupancy probe of Formula (IIa) covalently attached to MGLL has the structure:

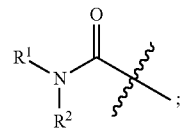

wherein ⁄ represents the attachment of the radiolabeled MGLL occupancy probe of Formula (IIa) to the MGLL enzyme.

In some embodiments is a method for assessing MGLL enzyme occupancy of a MGLL inhibitor in a mammal, comprising administering the MGLL inhibitor to the mammal, administering a radiolabeled MGLL occupancy probe of Formula (III) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (II) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (III) in the brain of the mammal is measured.

In some embodiments is a method for assessing tissue distribution of a MGLL inhibitor in a mammal, comprising administering a radiolabeled MGLL occupancy probe of Formula (III) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (III).

In some embodiments is a method for detecting a radiolabeled MGLL enzyme comprising contacting tissues expressing the MGLL enzyme with a radiolabeled MGLL occupancy probe of Formula (III) and detecting MGLL occupancy by PET imaging.

In some embodiments is an inhibited, radiolabeled monoacylglycerol lipase comprising a radiolabeled MGLL occupancy probe of Formula (III) irreversibly and covalently bound to the active-site serine in MGLL. In some embodiments, the inhibited, radiolabeled monoacylglycerol lipase comprising a radiolabeled MGLL occupancy probe of Formula (III) covalently attached to MGLL has the structure:

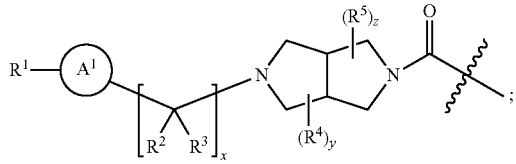

wherein ∕ represents the attachment of the radiolabeled MGLL occupancy probe of Formula (III) to the MGLL enzyme.

In some embodiments is a method for assessing MGLL enzyme occupancy of a MGLL inhibitor in a mammal, comprising administering the MGLL inhibitor to the mammal, administering a radiolabeled MGLL occupancy probe of Formula (IV) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard. In some embodiments is a method for assessing MGLL enzyme occupancy of a MGLL inhibitor in a mammal, comprising administering the MGLL inhibitor to the mammal, administering a radiolabeled MGLL occupancy probe of Formula (IV) to the mammal; measuring the MGLL enzyme occupancy of the radiolabeled MGLL occupancy probe in the mammal, and comparing the MGLL enzyme occupancy of the radiolabeled MGLL occupancy probe in the mammal to a standard; wherein the standard is the MGLL enzyme occupancy of the radiolabeled MGLL occupancy probe in the mammal after administration of the radiolabeled MGLL occupancy probe without administration of the MGLL inhibitor. In some embodiments for assessing MGLL enzyme occupancy of a MGLL inhibitor in a mammal, the MGLL enzyme occupancy of the radiolabeled MGLL occupancy probe of Formula (IV) in the brain of the mammal is measured.

In some embodiments is a method for assessing tissue distribution of a MGLL inhibitor in a mammal, comprising administering a radiolabeled MGLL occupancy probe of Formula (IV) to the mammal, and measuring the whole body biodistribution of the MGLL inhibitor by whole body PET imaging.

In some embodiments is a method for labeling a MGLL enzyme comprising contacting tissues expressing the MGLL enzyme with a radiolabeled MGLL occupancy probe of Formula (IV).

In some embodiments is a method for detecting a radiolabeled MGLL enzyme comprising contacting tissues expressing the MGLL enzyme with a radiolabeled MGLL occupancy probe of Formula (IV) and detecting MGLL occupancy by PET imaging.

In some embodiments is an inhibited, radiolabeled monoacylglycerol lipase comprising a radiolabeled MGLL occupancy probe of Formula (IV) irreversibly and covalently bound to the active-site serine in MGLL. In some embodiments, the inhibited, radiolabeled monoacylglycerol lipase comprising a radiolabeled MGLL occupancy probe of Formula (IV) covalently attached to MGLL has the structure:

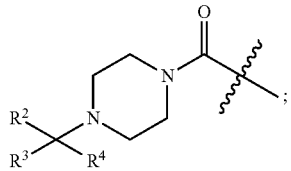

wherein ∕ represents the attachment of the radiolabeled MGLL occupancy probe of Formula (IV) to the MGLL enzyme.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

In some embodiments provided herein a kit includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use or preparation. A set of instructions will also typically be included.

In some embodiments provided herein is a kit for identifying a subject having pain, multiple sclerosis, Alzheimer's disease, and/or inflammatory bowel disease, who is likely to be responsive to treatment with an MGLL inhibitor of Formula (I), comprising a means for detecting the level of MGLL receptor occupancy in a sample that has been treated with a compound, wherein the treatment compound is a compound of Formula (I). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (I). In some embodiments provided herein is a kit for identifying a subject having pain, multiple sclerosis, Alzheimer's disease, and/or inflammatory bowel disease, who is likely to be responsive to treatment with an MGLL inhibitor of Formula (Ia), comprising a means for detecting the level of MGLL receptor occupancy in a sample that has been treated with a compound, wherein the treatment compound is a compound of Formula (Ia). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (Ia). In some embodiments provided herein is a kit for identifying a subject having pain, multiple sclerosis, Alzheimer's disease, and/or inflammatory bowel disease, who is likely to be responsive to treatment with an MGLL inhibitor of Formula (Ib), comprising a means for detecting the level of MGLL receptor occupancy in a sample that has been treated with a compound, wherein the treatment compound is a compound of Formula (Ib). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (Ib). In some embodiments provided herein is a kit for identifying a subject having pain, multiple sclerosis, Alzheimer's disease, and/or inflammatory bowel disease, who is likely to be responsive to treatment with an MGLL inhibitor of Formula (Ic), comprising a means for detecting the level of MGLL receptor occupancy in a sample that has been treated with a compound, wherein the treatment compound is a compound of Formula (Ic). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (Ic). In some embodiments provided herein is a kit for identifying a subject having pain, multiple sclerosis, Alzheimer's disease, and/or inflammatory bowel disease, who is likely to be responsive to treatment with an MGLL inhibitor of Formula (II), comprising a means for detecting the level of MGLL receptor occupancy in a sample that has been treated with a compound, wherein the treatment compound is a compound of Formula (II). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (II). In some embodiments provided herein is a kit for identifying a subject having pain, multiple sclerosis, Alzheimer's disease, and/or inflammatory bowel disease, who is likely to be responsive to treatment with an MGLL inhibitor of Formula (IIa), comprising a means for detecting the level of MGLL receptor occupancy in a sample that has been treated with a compound, wherein the treatment compound is a compound of Formula (IIa). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (IIa). In some embodiments provided herein is a kit for identifying a subject having pain, multiple sclerosis, Alzheimer's disease, and/or inflammatory bowel disease, who is likely to be responsive to treatment with an MGLL inhibitor of Formula (III), comprising a means for detecting the level of MGLL receptor occupancy in a sample that has been treated with a compound, wherein the treatment compound is a compound of Formula (III). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (III). In some embodiments provided herein is a kit for identifying a subject having pain, multiple sclerosis, Alzheimer's disease, and/or inflammatory bowel disease, who is likely to be responsive to treatment with an MGLL inhibitor of Formula (IV), comprising a means for detecting the level of MGLL receptor occupancy in a sample that has been treated with a compound, wherein the treatment compound is a compound of Formula (IV). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (IV). In some embodiments provided herein is a kit for identifying a subject having pain, multiple sclerosis, Alzheimer's disease, and/or inflammatory bowel disease, who is likely to be responsive to treatment with an MGLL inhibitor of Formula (V), comprising a means for detecting the level of MGLL receptor occupancy in a sample that has been treated with a compound, wherein the treatment compound is a compound of Formula (V). In some embodiments provided herein is a kit for treating pain, multiple sclerosis, Alzheimer's disease, and/or inflammatory bowel disease, comprising a means for detecting the level of MGLL occupancy in a sample that has been treated with a treatment compound, wherein the treatment compound is a compound of Formula (V).

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane
DCM dichloromethane DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
equiv or eq equivalent(s)
Et ethyl
Et$_2$O diethyl ether
EtOH ethanol
EtOAc ethyl acetate
HPLC high performance liquid chromatography
LAH lithium aluminum anhydride
Me methyl
MeOH methanol
MS mass spectroscopy
NMM N-methyl-morpholine
NMP N-methyl-pyrrolidin-2-one
NMR nuclear magnetic resonance
RP-HPLC reverse phase-high pressure liquid chromatography
TFA trifluoroacetic acid
THF tetrahydrofuran
TLC thin layer chromatography Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. In some instances, compounds were purified using preparative HPLC on a Waters 2767-5 Chromatograph. Spectra are given in ppm (δ) and coupling constants, J are reported in Hertz. For proton spectra the solvent peak was used as the reference peak.

Example 1

Synthesis of 1,1,1,3,3,3-hexafluoropropan-2-yl 4-(4-chloro-2-(4-(2-fluoroethyl)piperazin-1-yl)benzyl) piperazine-1-carboxylate (8)

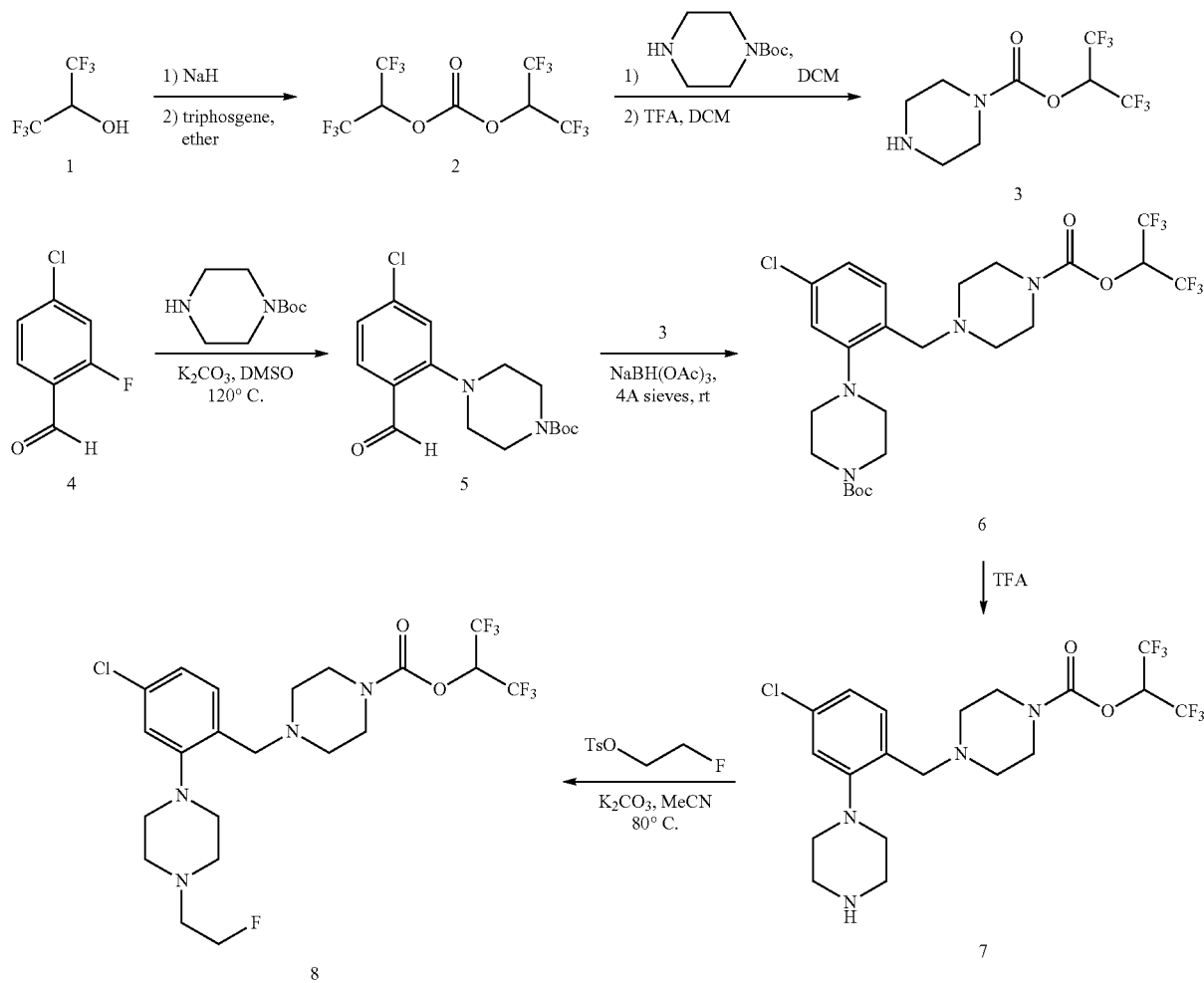

A 500 mL flask was charged with sodium hydride (60% dispersion, 8.16 g, 204 mmol). Ether (100 mL) was added and the reaction was cooled to 0° C. A solution of 1,1,1,3,3,3-hexafluoro-2-propanol (1) (21 mL, 204 mmol) in ether (40 mL) was added via addition funnel over 10 min. The reaction became clear by the end of the addition. The reaction was stirred at 0° C. for 20 min and then allowed to warm to room temperature and stirred for 20 min. The solution was transferred via cannula (~10 mL/min) to a 0° C.

solution of triphosgene (10 g, 33.7 mmol) in ether (40 mL) resulting in an exothermic reaction and formation of a precipitate. The solution was stirred at room temperature for 2 h. The reaction was filtered and the solids were washed with ether (50 mL). The filtrate was carefully concentrated (water bath maintained at 36° C., and vacuum at 500 Torr) via rotary evaporation to yield a cloudy solution, which partitions into a top (organic) and bottom (fluorous) layer. The bottom layer was retained to give bis[2,2,2-trifluoro-1-(trifluoromethyl)ethyl] carbonate (2) (8.00 g, 78% by weight solution in ether, 51% yield) as a solution. This was used in the next reaction without further purification. $^1$H NMR (400 MHz, Chloroform-d) δ 5.50 (hept, J=5.7 Hz, 1H). $^{13}$C NMR (101 MHz, CDCl$_3$) δ 151.56, 123.85, 121.02, 118.24, 115.41, 72.51, 72.16, 71.80, 71.45, 71.09.

A flask was charged with tert-butyl-1-piperazinecarboxylate (6.0 g, 32.2 mmol) and dissolved in DCM (50 mL). The solution was cooled to 0° C. and bis[2,2,2-trifluoro-1-(trifluoromethyl)ethyl] carbonate (2) (12.2 g, 33.8 mmol) was added dropwise and the reaction was stirred at 0° C. for 1 h. The ice bath was removed and the reaction allowed to warm to room temperature prior to concentration under reduced pressure. MeOH (100 mL) was added and the reaction was concentrated in vacuo resulting in a white powder. The crude 1-(tert-butyl) 4-(1,1,1,3,3,3-hexafluoropropan-2-yl) piperazine-1,4-dicarboxylate was dissolved in DCM (40 mL) and triflouoroacetic acid (10 mL) was added and the reaction was stirred at room temp for 5 h. The reaction was concentrated and resuspended in cold DCM (200 mL) and 1N NaOH (50 mL). The aqueous layer was extracted with DCM (3×100 mL). The organics were dried over anhydrous sodium sulfate, filtered, and carefully concentrated to yield 1,1,1,3,3,3-hexafluoropropan-2-yl piperazine-1-carboxylate (3) (6.4 g, 70% yield) as a light orange oil. $^1$H NMR (400 MHz, Chloroform-d) δ 5.84-5.71 (m, 1H), 3.60-3.51 (m, 4H), 2.96-2.80 (m, 4H). LCMS (ESI, m/z): 281.2 [M+H]$^+$.

A thick walled flask was charged with 4-chloro-2-fluorobenzaldehyde (4) (1.00 g, 6.31 mmol) and tert-butyl-1-piperazinecarboxylate (1.17 g, 6.31 mmol). DMSO was added (10 mL) followed by potassium carbonate (870 mg, 6.31 mmol), the reaction was sealed, and was heated to 120° C. for 8 h. The reaction was cooled to rt, then diluted with EtOAc (200 mL). The organic layer was washed with brine (3×100 mL) and sat NH$_4$Cl (1×100 mL). The organic layers were dried over sodium sulfate, filtered and concentrated under reduced pressure to yield a solid. The solid was purified on silica gel by flash column chromatography (0 to 20% EtOAc in hexane) to afford tert-butyl 4-(5-chloro-2-formylphenyl)piperazine-1-carboxylate (5) (1.50 g, 73% yield). $^1$H NMR (400 MHz, Chloroform-d) δ 10.25 (s, 1H), 7.77 (d, J=8.3 Hz, 1H), 7.18-7.05 (m, 2H), 3.69-3.61 (m, 4H), 3.09-3.02 (m, 4H), 1.51 (s, 9H). LCMS (ESI, m/z): 325.1 [M+H]$^+$.

A 100 mL flask equipped with a magnetic stir bar was charged with tert-butyl 4-(5-chloro-2-formylphenyl)piperazine-1-carboxylate (5) (5.9 g, 18.2 mmol). The solid was dissolved in DCM (50 mL) and stirred at room temperature. 1,1,1,3,3,3-hexafluoropropan-2-yl piperazine-1-carboxylate (3) (5.5 g, 19.2 mmol) and 4 Å molecular sieves (1 g) were added and the reaction was stirred at room temperature for 3 h. NaBH(OAc)$_3$ (4.2 g, 19.9 mmol) was added and the reaction was allowed to stir at room temperature overnight. The reaction was filtered over Celite and washed with DCM (100 mL). The organic layer was washed with 1N NaOH (2×50 mL) and dried over anhydrous sodium sulfate, filtered, and concentrated. The resulting oil was chromatographed on a silica column with a gradient 0% to 10%. MeOH in DCM and followed by a second chromatography with 0 to 20% acetone in DCM and yielded tert-butyl 4-(5-chloro-2-((4-(((1,1,1,3,3,3-hexafluoropropan-2-yl)oxy)carbonyl)piperazin-1-yl)methyl)phenyl)piperazine-1-carboxylate (6) (6.7 g, 56% yield) as a clear oil. $^1$H NMR (400 MHz, Chloroform-d) δ 7.17 (d, J=8.2 Hz, 1H), 6.91-6.83 (m, 2H), 5.57 (hept, J=6.1 Hz, 1H), 3.36 (s, 10H), 2.78-2.64 (m, 4H), 2.30 (dt, J=9.6, 4.9 Hz, 4H), 1.31 (s, 9H). LCMS (ESI, m/z): 590.2 [M+H]$^+$.

A flask was charged with tert-butyl 4-(5-chloro-2-((4-(((1,1,1,3,3,3-hexafluoropropan-2-yl)oxy)carbonyl)piperazin-1-yl)methyl)phenyl)piperazine-1-carboxylate (6) (8.0 g, 13.6 mmol) and DCM (40 mL) was added. Trifluoroacetic acid (10 mL) was added and the reaction was stirred at room temperature for 4 h. The reaction was concentrated and DCM (100 mL) was added. The solution was poured into a cold 1N NaOH solution (70 mL). The aqueous phase was extracted with DCM (3×100 mL). The resulting clear oil 1,1,1,3,3,3-hexafluoropropan-2-yl 4-(4-chloro-2-(piperazin-1-yl)benzyl)piperazine-1-carboxylate (7) (6.7 g, 99% yield) was used without further purification. $^1$H NMR (400 MHz, Chloroform-d) δ 7.38 (d, J=8.7 Hz, 1H), 7.10-7.02 (m, 2H), 5.77 (hept, J=6.3 Hz, 1H), 3.55 (d, J=4.7 Hz, 6H), 3.02 (t, J=4.7 Hz, 4H), 2.94-2.86 (m, 4H), 2.49 (dt, J=9.9, 5.0 Hz, 4H). LCMS (ESI, m/z): 489.2 [M+H]$^+$.

A thick walled tube was charged with 1,1,1,3,3,3-hexafluoropropan-2-yl 4-(4-chloro-2-(piperazin-1-yl)benzyl)piperazine-1-carboxylate (7) (200 mg, 0.409 mmol), potassium carbonate (113 mg, 0.818 mmol), and a solution of 2-fluoroethyl-4-methylbenzenesulfonate (89 mg, 0.409 mmol) in MeCN (11 mL). The reaction was heated to 80° C. for 8 h. The reaction mixture was cooled, poured into brine (30 mL), and extracted with DCM (3×50 mL). The organics were dried over anhydrous sodium sulfate, filtered, and concentrated. The resulting oil was chromatographed on a silica column with a gradient (0 to 30% EtOAc in hexane) and yielded 1,1,1,3,3,3-hexafluoropropan-2-yl 4-(4-chloro-2-(4-(2-fluoroethyl)piperazin-1-yl)benzyl)piperazine-1-carboxylate (8) (100 mg, 43%). $^1$H NMR (400 MHz, Chloroform-d) δ 7.37 (d, J=8.7 Hz, 1H), 7.13-7.02 (m, 2H), 5.77 (hept, J=6.3 Hz, 1H), 4.71 (t, J=4.8 Hz, 1H), 4.59 (t, J=4.8 Hz, 1H), 3.62-3.47 (m, 6H), 3.01 (t, J=4.3 Hz, 4H), 2.84 (t, J=4.7 Hz, 1H), 2.81-2.64 (m, 5H), 2.50 (dt, J=9.3, 5.0 Hz, 4H). LCMS (ESI, m/z): 535.2 [M+H]$^+$.

Example 1A

Alternate Synthesis of 1,1,1,3,3,3-hexafluoropropan-2-yl 4-(4-chloro-2-(4-(2-fluoroethyl)piperazin-1-yl)benzyl)piperazine-1-carboxylate (8)

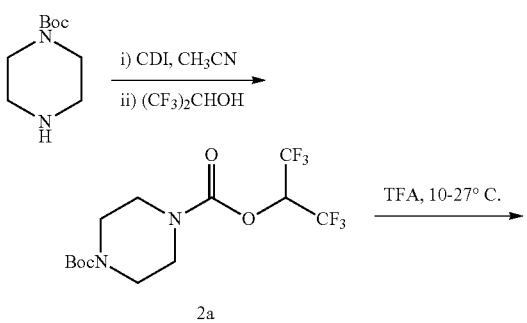

-continued

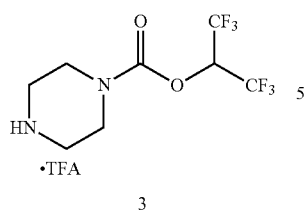

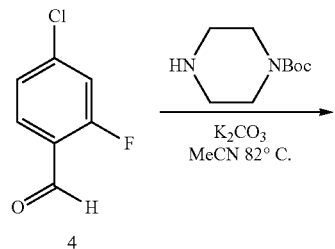

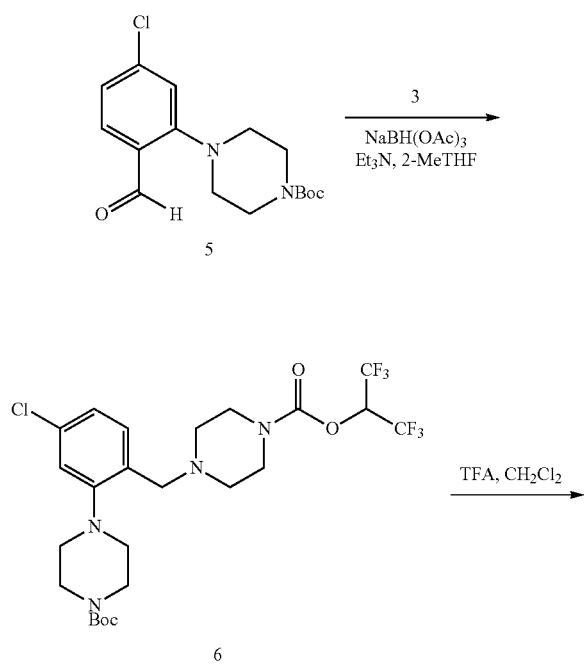

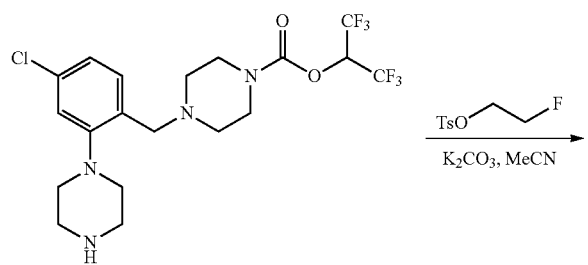

-continued

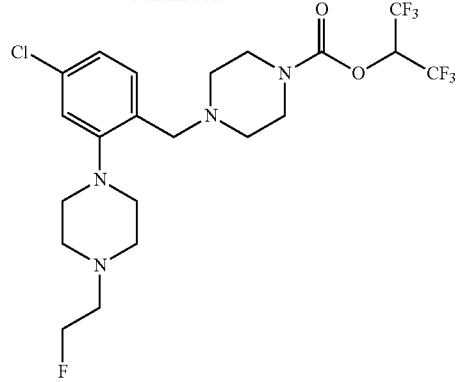

A flask was charged with 1,1-carbonyldiimidazole (33.4 g, 206 mmol) and acetonitrile (75.8 g). To the flask was charged a solution of tert-butyl-1-piperazinecarboxylate (1) (32.0 g, 172 mmol) in acetonitrile (25.3 g). The yellow solution was stirred at 19-25° C. for 3 hours. 1,1,1,3,3,3-hexafluoropropan-2-ol (88.2 g, 525 mmol) was added at a rate that the maximum temperature did not exceed 25° C. The solution was heated to 77-83° C. and stirred for 18 hours. The solution was then allowed to cool to 47-53° C. and sampled for reaction completion. The solution was cooled to 19-25° C. and demineralized water (320 g) was added slowly while keeping the internal temperature below 30° C. The mixture was concentrated under reduced pressure to a total volume of 320 mL. The suspension was filtered and washed with demineralized water (64 g). After the initial isolation, the wet cake was taken up in demineralized water (320 g) and stirred for 30 minutes. The product was filtered and washed with demineralized water (64 g) and then dried under vacuum for 18 hours to provide 1-(tert-butyl) 4-(1,1,1,3,3,3-hexafluoropropan-2-yl) piperazine-1,4-dicarboxylate (2a) as a white solid in 96% yield. $^1$H NMR (400 MHz, DMSO-d) δ 6.58-6.65 (m, 1H), 3.43 (m, 4 H), 3.37-3.32 (m, 4H), 1.24 (s, 9H). LCMS (ESI, m/z): 381.3 [M+H]$^+$.

To a flask was added 1-(tert-butyl) 4-(1,1,1,3,3,3-hexafluoropropan-2-yl) piperazine-1,4-dicarboxylate (2a) (60.9 g, 0.16 mol) and dichloromethane (91.4 mL). Trifluoroacetic acid (90.7 g, 0.795 mol) was charged slowly maintaing the internal temperature below 30° C. The reaction mixture was stirred at 25° C. for 3.5 hours. To another flask was charged water (609 g). The TFA solution of 2 was then added to the water over 12 minutes. The suspension was cooled to 0-6° C. and stirred for 30 minutes before filtering the suspension. The wet filter cake was washed with demineralized water (122 g) and dried in a vacuum oven at 40° C. to provide 1,1,1,3,3,3-hexafluoropropan-2-yl piperazine-1-carboxylate trifluoroacetic acid salt (3) as a white solid in 94% yield. $^1$H NMR (400 MHz, Chloroform-d) δ 5.84-5.71 (m, 1H), 3.60-3.51 (m, 4H), 2.96-2.80 (m, 4H). LCMS (ESI, m/z): 281.2 [M+H]$^+$.

A flask was charged with 4-chloro-2-fluorobenzaldehyde (4) (100 g, 0.63 mol), tert-butyl-1-piperazinecarboxylate (140.9 g, 0.76 mol), and potassium carbonate (261.4 g, 1.89 mmol). Acetonitrile was added (1000 mL) and the reaction mixture was stirred at reflux for 18 h. The reaction mixture was cooled to room temperature and ethyl acetate (1000 mL) was added. Water (500 mL) was added and the mixture was stirred at room temperature for 10 min. The layers were separated and the aqueous layer was extracted with ethyl acetate (2×500 mL). The organic layers were combined, washed with saturated brine (500 mL), dried over MgSO₄, and the solvent was removed in vacuo. The residue was re-suspended in 1:4 (MTBE/n-heptane; 500 mL) and filtered to provide tert-butyl 4-(5-chloro-2-formylphenyl)piperazine-1-carboxylate (5) as a yellow solid in 71% yield. $^1$H NMR (400 MHz, Chloroform-d) δ 10.25 (s, 1H), 7.77 (d, J=8.3 Hz, 1H), 7.18-7.05 (m, 2H), 3.69-3.61 (m, 4H), 3.09-3.02 (m, 4H), 1.51 (s, 9H). LCMS (ESI, m/z): 325.1 [M+H]⁺.

A flask was charged with tert-butyl 4-(5-chloro-2-formylphenyl)piperazine-1-carboxylate (5) (105 g, 0.32 mol), triethylamine (49.5 g, 0.49 mol) and tetrahydro-2-methylfuran (1050 mL). The reaction mixture was stirred at room temperature for 15 minutes and 1,1,1,3,3,3-hexafluoropropan-2-yl piperazine-1-carboxylate trifluoroacetic acid salt (3) (140.2 g, 0.36 mol) was added. The reaction was stirred at room temperature for 3 h and then NaBH(OAc)₃ (119.9 g, 0.57 mol) was added portion-wise. The reaction was allowed to stir at ambient temperature overnight. To the reaction was slowly added water (1050 mL) and the reaction mixture was stirred at room temperature for 30 minutes. The layers were separated and the aqueous layer was extracted with tetrahydro-2-methylfuran (2×300 mL). The organics were combined and dried over MgSO₄, and filtered. The solvent was removed in vacuo to provide a residue that was dissolved in dichloromethane (500 mL) and the solution was filtered through celite. The celite was washed with additional dichloromethane (200 mL) and the solvent was removed in vacuo. The residue was dissolved in 2-propanol (200 mL) and the solvent was slowly distilled (removed ca. half of the volume) to provide a suspension. Additional 2-propanol (500 mL) was added and the resulting suspension was stirred at room temperature for 1 hr. The suspension was filtered to provide tert-butyl 4-(5-chloro-2-((4-(((1,1,1,3,3,3-hexafluoropropan-2-yl)oxy)carbonyl)piperazin-1-yl)methyl)phenyl)piperazine-1-carboxylate (6) as a white solid in 86% yield. $^1$H NMR (400 MHz, Chloroform-d) δ 7.17 (d, J=8.2 Hz, 1H), 6.91-6.83 (m, 2H), 5.57 (hept, J=6.1 Hz, 1H), 3.36 (s, 10OH), 2.78-2.64 (m, 4H), 2.30 (dt, J=9.6, 4.9 Hz, 4H), 1.31 (s, 9H). LCMS (ESI, m/z): 589.2 [M+H]⁺.

A flask was charged with tert-butyl 4-(5-chloro-2-((4-(((1,1,1,3,3,3-hexafluoropropan-2-yl)oxy)carbonyl)piperazin-1-yl)methyl)phenyl)piperazine-1-carboxylate (6) (152.1 g, 0.26 mol) and dichloromethane (761 mL) was added. Trifluoroacetic acid (127.6 g) was added and the reaction was stirred at room temperature for 4 h. The solvent was removed in vacuo and dichloromethane was added (1330 mL) followed by IM NaOH (1330 mL). The pH was determined to be 8-9 and if necessary additional IM NaOH was added to bring the mixture to pH 8-9. The layers were separated and the organic layer was washed once with brine (500 mL). The solvent was removed in vacuo to provide 1,1,1,3,3,3-hexafluoropropan-2-yl 4-(4-chloro-2-(piperazin-1-yl)benzyl)piperazine-1-carboxylate (7) as a light yellow oil in 97% yield that was used without further purification. $^1$H NMR (400 MHz, Chloroform-d) δ 7.38 (d, J=8.7 Hz, 1H), 7.10-7.02 (m, 2H), 5.77 (hept, J=6.3 Hz, 1H), 3.55 (d, J=4.7 Hz, 6H), 3.02 (t, J=4.7 Hz, 4H), 2.94-2.86 (m, 411), 2.49 (dt, J=9.9, 5.0 Hz, 4H). LCMS (ESI, m/z). 489.2 [M+H]⁺.

A flask was charged with 1,1,1,3,3,3-hexafluoropropan-2-yl 4-(4-chloro-2-(piperazin-1-yl)benzyl)piperazine-1-carboxylate (7) (30.0 g, 61.4 mmol), potassium carbonate (16.9 g, 122.3 mmol), 2-fluoroethyl-4-methylbenzenesulfonate (14.7 g, 67.4 mmol) in MeCN (1500 mL). The reaction was heated to 80° C. and stirred for 17 h. The reaction mixture was allowed to cool to 22° C., poured into brine (1500 mL), and extracted with DCM (3×1000 mL). The combined organics were dried over anhydrous sodium sulfate, filtered, and concentrated in vacuo. The crude product was purified by silica gel chromatography (5 to 30% EtOAc in heptane) to afford 1,1,1,3,3,3-hexafluoropropan-2-yl 4-(4-chloro-2-(4-(2-fluoroethyl)piperazin-1-yl)benzyl)piperazine-1-carboxylate (8) in 49% yield. $^1$H NMR (400 MHz, Chloroform-d) δ 7.37 (d, J=8.7 Hz, 1H), 7.13-7.02 (m, 2H), 5.77 (hept, J=6.3 Hz, 1H), 4.71 (t, J=4.8 Hz, 1H), 4.59 (t, J=4.8 Hz, 1H), 3.62-3.47 (m, 6H), 3.01 (t, J=4.3 Hz, 4H), 2.84 (t, J=4.7 Hz, 1H), 2.81-2.64 (m, 5H), 2.50 (dt, J=9.3, 5.0 Hz, 4H). LCMS (ESI, m/z): 535.2 [M+H]⁺.

Example 2

Synthesis of [$^{18}$F]1,1,1,3,3,3-hexafluoropropan-2-yl 4-(4-chloro-2-(4-(2-fluoroethyl)piperazin-1-yl)benzyl)piperazine-1-carboxylate (8F)

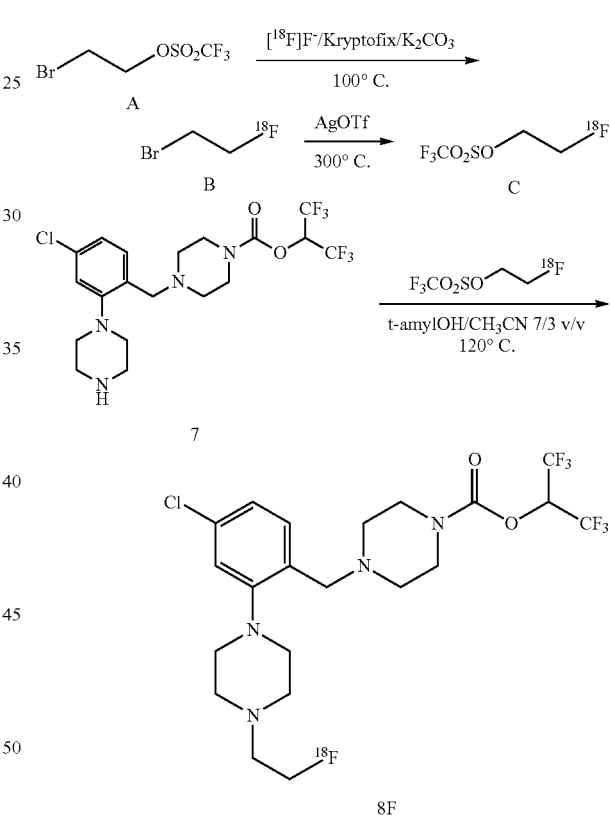

[$^{18}$F]F⁻ was obtained via the nuclear reaction $^{18}$O(p,n)$^{18}$F. This was achieved by bombarding 2-3 mL of oxygen-18 enriched water (90-99% enrichment) contained in a closed niobium target with 18-MeV protons accelerated in an IBA Cyclone 18/9 cyclotron for 30 min to 1 hour.

The irradiated target water was transferred to a remote controlled synthesis module where the [$^{18}$F]fluoride was displaced from the column with a solution of potassium carbonate (K₂CO₃) and Kryptofix 222 which was collected in a conical reactor vessel.

The [$^{18}$F]F⁻/K₂CO₃/kryptofix mixture was evaporated under a stream of helium by applying thermal heating to evaporate water and acetonitrile (CH₃CN) and the residue was further dried by azeotropic distillation using anhydrous CH$_3$CN. About 0.33 mL of CH$_3$CN was added, the mixture was heated under helium flow to dryness, and the operation repeated 3 times.

A solution of 2-bromoethyl triflate (A) in anhydrous 1,2-dichlorobenzene (1,2-DCB, o-DCB) was added to the [$^{18}$F]F$^-$/K$_2$CO$_3$/kryptofix residue and the reaction mixture was heated to provide 2-[$^{18}$F]fluoroethylbromide ([$^{18}$F]FEtBr) (B) which was distilled from the reactor with a gentle flow of helium to a second reactor located in another remote controlled synthesis module. It passes a column filled with ascarite followed by a column filled with silver triflate (AgOTf) heated at 300° C. to form 2-[$^{18}$F]fluoroethyl triflate ([$^{18}$F]FEtOTf) (C). The second reactor contains a solution of 0.5 mg of Compound 7 (radiolabeling precursor) in 200 μL of a mixture of tertiary amylalcohol (t-amylOH) and anhydrous CH$_3$CN (7/3 V/V). After distillation of a sufficient amount of radioactivity into the precursor solution, the reaction vial was closed and heated to afford the nucleophilic substitution reaction between [$^{18}$F]FEtOTf (C) and Compound 7.

After dilution, the crude reaction mixture was injected onto an HPLC system consisting of a reversed phase column which was eluted with a mixture of sodium phosphate 0.05 M pH 5.5 and ethanol (EtOH) (45/55 v/v) to purify the title compound (8F) from unreacted [$^{18}$F]fluoride, Compound 7, and other chemical and radiochemical impurities. The resulting Compound 8F solution in EtOH/sodium phosphate 0.05 M pH 5.5 buffer was used immediately to manufacture the drug product.

Example 3

Compound 8F Formulation

The HPLC-purified Compound 8F solution from Example 2 was transferred to the laminar air flow (LAF) hood. The solution was taken up in a sterile syringe, the volume was corrected to 2 mL and the solution was filtered through a single use apyrogenic syringe filter (Millex-GV filter 0.22 μm Ø 13 mm or equivalent) into a sterile vial. Next, (in the LAF hood), a Vit C ampule was opened, 0.8 mL was taken up in a sterile syringe and immediately added to a 100-mL bottle of NaCl 0.9% for injection via the septum. After hand mixing, 1 mL of the solution of Vit C in NaCl 0.9% (concentration 0.67 mg/mL) was taken up in a sterile syringe and filtered via the same sterile filter into the sterile vial to achieve a final composition of 8.5% v/v EtOH, 3.5 mM sodium acetate buffer pH 5.5, 0.07% w/v ascorbic acid and 0.8% w/v NaCl in WFI.

Example 4

Compound 8 In Vitro and In Vivo Characterization

Compound 8 belongs to the O-hexafluoroisopropyl carbamate compound class, which inhibit MGLL through a covalent and irreversible mechanism. Thus, Compound 8 is expected to form a covalent adduct with the active-site serine in MGLL, simultaneously labeling the enzyme for imaging purposes and inhibiting its catalytic activity. Compound 8 is a potent inhibitor of human and mouse MGLL with an IC$_{50}$ of <20 nM.

To characterize the in vitro activity and selectivity of Compound 8, MGLL activity was measured using activity-based protein profiling (ABPP), which is a functional proteomic technology that uses chemical probes to covalently modify enzyme active sites in an activity-dependent manner (e.g., only catalytically active enzymes will react and become labeled with the ABPP probe). Visualization of the proteins that are labeled by fluorescent probes can be accomplished using polyacrylamide gel electrophoresis and in-gel fluorescent scanning. Loss of target-associated fluorescent signals following in vitro treatment of tissue or cell homogenates with Compound 8 can be used to identify the targets of Compound 8 and quantitate the extent of inhibition.

Treatment of mouse and human brain homogenates and human PC3 prostate cancer cell lysates with Compound 8 (0-10 μM, 37° C., 30 min, n=3 independent experiments per source material) potently and selectively inhibited MGLL activity. The potency of Compound 8 was calculated as the IC$_{50}$ following a 30-minute pre-incubation. The IC$_{50}$ values are summarized in Table 1.

TABLE 1

| Species | Source | MGLL IC$_{50}$ (nM ± SEM) |
|---|---|---|
| Human | PC3 Cells | 4 ± 0.2 |
| Human | Brain tissue | 5 ± 1 |
| Mouse | Brain tissue | 17 ± 6 |

The in vivo activity of Compound 8 in mice was assessed by ABPP. As Compound 8 is expected to inhibit MGLL through a covalent mechanism, ABPP analysis of brain tissue from mice treated with Compound 8 allows visualization and quantitation of MGLL target engagement in vivo. In this experimental protocol, male ICR mice (n=3) received a single, oral gavage (i.e., per os; by the oral route [PO]) dose of Compound 8 (5 mg/kg). Four hours after dosing, the mice were sacrificed, brains were collected and membrane homogenates were prepared for ABPP analysis. Two complementary ABPP probes were used in this study: fluorophosphonate-rhodamine (FP-Rh), which reacts broadly with enzymes in the serine hydrolase enzyme class, including MGLL, and HT-01, which reacts with a smaller subset of serine hydrolases, not including MGLL. As depicted in FIG. 1 selective and near-complete inhibition of MGLL in the mouse brain was observed 4 h following PO administration of 5 mg/kg Compound 8.

Example 5

Non-Clinical Evaluation of Compound 8F MGLL Enzyme Occupancy Using PET Brain Imaging Screening and Dose Occupance PET Studies in Rhesus Monkeys Based on the in vitro and in vivo characterization of Compound 8, Compound 8F forms a covalent adduct between the carbamoyl moiety of the inhibitor and the nucleophilic serine in the MGLL active site. Upon reacting with MGLL, the [$^{18}$F]-radiolabeled portion of Compound 8F remains bound to the enzyme, enabling imaging by positron emission tomography (PET), while the hexafluoroisopropyl group is liberated. To validate Compound 8F as an imaging tool for MGLL, a series of PET studies were carried out in two rhesus monkeys, one female and one male.

The initial screening study was performed in one rhesus macaque and confirmed brain uptake of Compound 8F with sustained binding over the 240 min scan, a profile consistent with a covalent mechanism-of-action. The highest uptake values were observed in striatum followed by cortical regions and cerebellum and low uptake in the brainstem and subcortical white matter. This distribution of Compound 8F is consistent with the expected regional expression of MGLL in $CB_1$-containing neurons.

Figure 2:
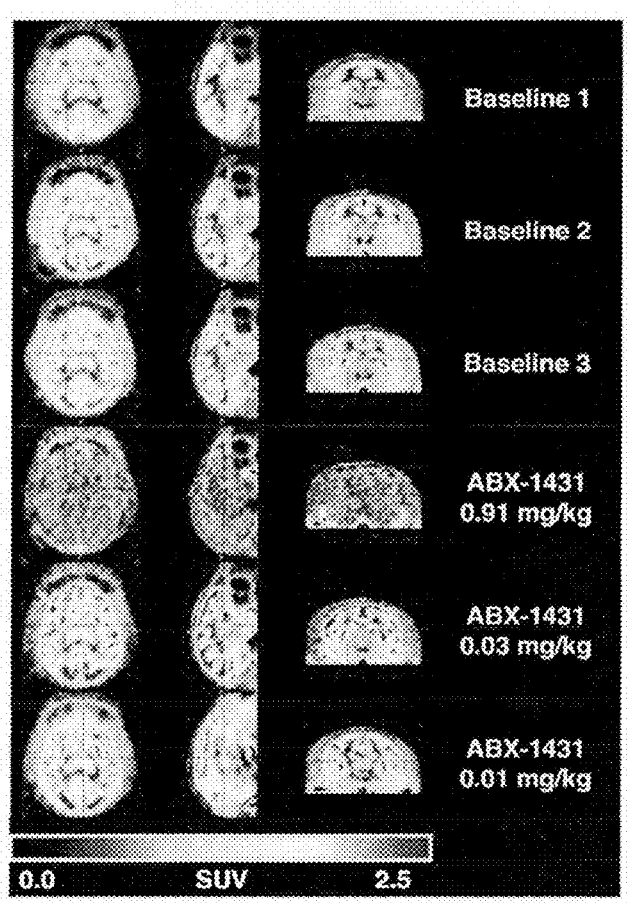
FIG. 2 depicts orthogonal positron emission tomography (PET) images from a rhesus monkey brain study showing Compound 8F binding at baseline (3 baseline studies) and again after administration of Compound 9 (Compound 9 doses of 0.91, 0.03, and 0.01 mg/kg).
Figure 3:
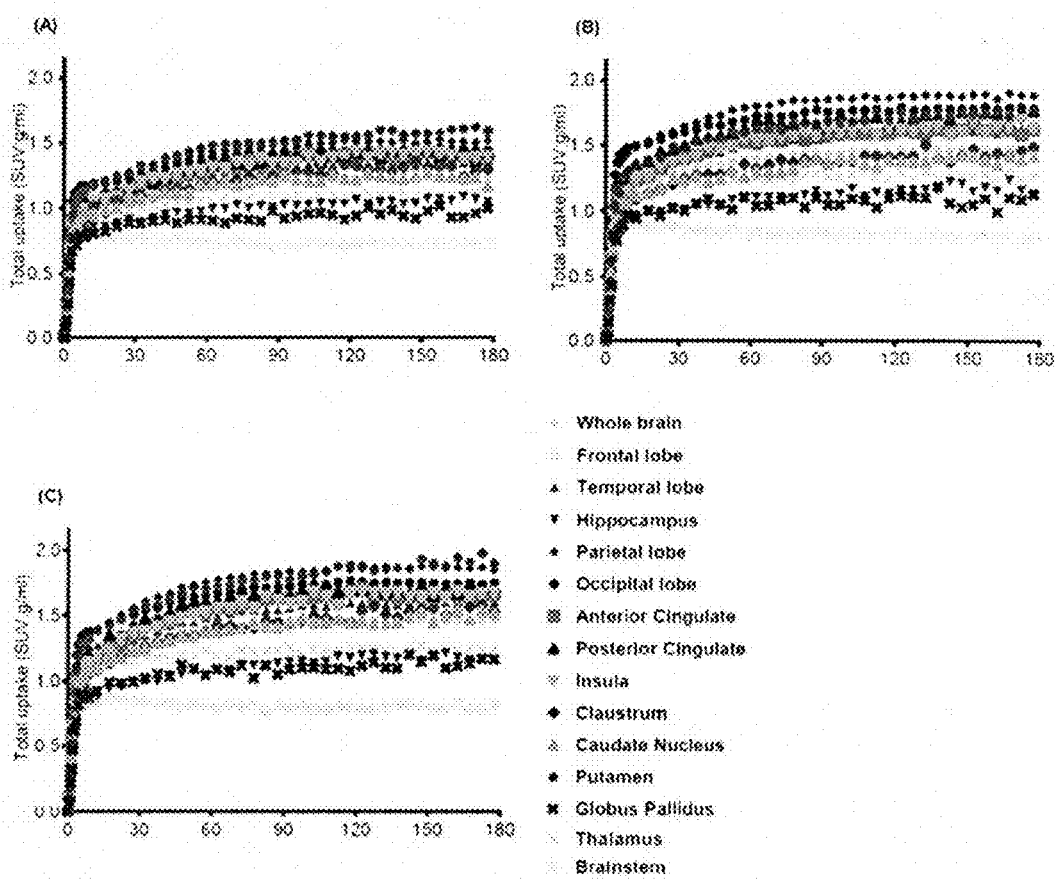
FIG. 3A-C depicts time activity curves for a rhesus monkey brain PET study showing Compound 8F binding at baseline (3 baseline studies).
Figure 4:
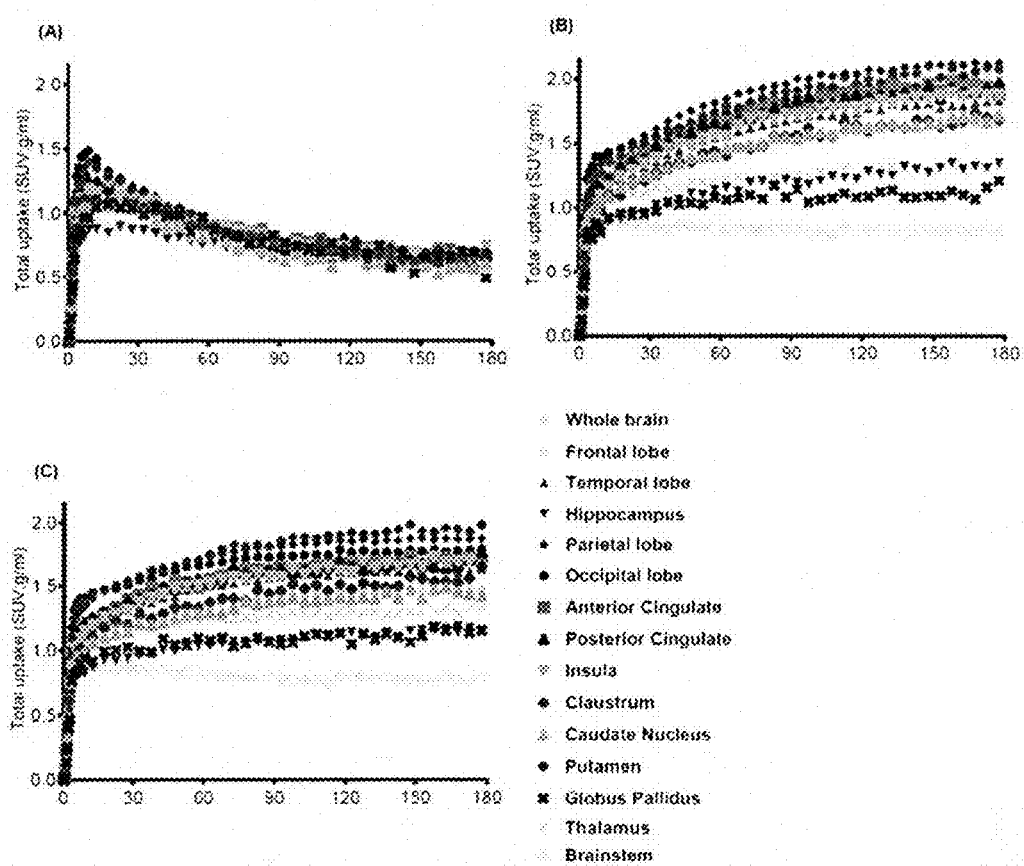
FIG. 4A-C depicts time activity curves for a rhesus monkey brain PET study showing Compound 8F binding following administration of Compound 9 (Compound 9 doses of 0.91, 0.03, and 0.01 mg/kg).
Figure 5:
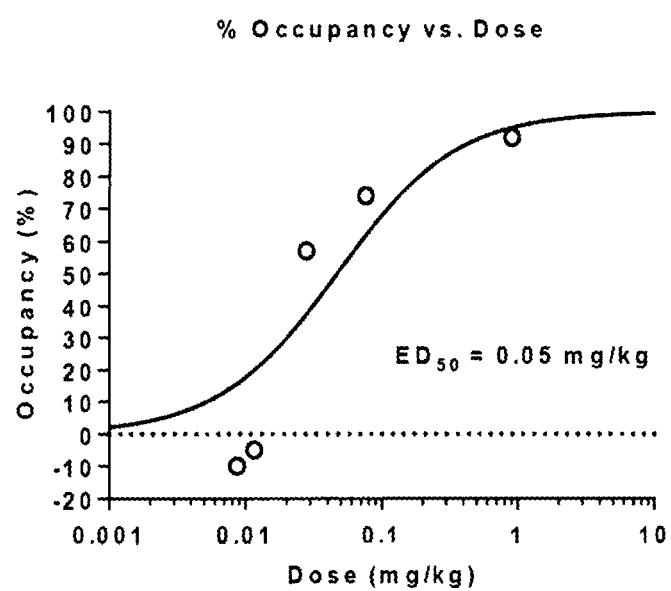
FIG. 5 shows the MGLL enzyme occupancy in the rhesus monkey brain as a function of Compound 9 administered dose.

Subsequently, Compound 8F was used to determine brain occupancy of a potent and selective MGLL inhibitor, Compound 9, using a blockade protocol comparing Compound 8F binding at baseline and again following administration of Compound 9. As outlined in Table 2, three baseline (FIG. 2 and FIG. 3) and three blockade studies with Compound 9 (FIG. 2 and FIG. 4) were carried out in one female monkey, and two baseline and two blockade studies were performed in one male monkey. Single Compound 9 doses of 0.91, 0.08, 0.03 and 0.01 mg/kg were administered by intravenous (i.v.) injection over 5 min starting 90 min before radiotracer injection. Compound 8F PET signal was blocked in a dose-dependent fashion with an average 50% of the maximum efficacious dose ($ED_{50}$) of 0.05 mg/kg Compound 9 (FIG. 5). At the highest dose of Compound 9 tested (0.91 mg/kg), MGLL enzyme occupancy close to 100% was achieved (FIG. 2 and FIG. 4A), with a similar occupancy in all brain regions.

TABLE 2

| Experiment type | Compound 9 dose | Animal gender | Animal weight (kg) | Compound 8F Injected dose (mCi) |
| --- | --- | --- | --- | --- |
| Screening | | Male | 18 | 2.8 |
| Baseline | | Female | 6.6 | 4.99 |
| Baseline | | | 6.4 | 4.47 |
| Baseline | | | 6.3 | 4.62 |
| Blocking | 0.91 mg/kg | | 6.4 | 2.58 |
| Blocking | 0.03 mg/kg | | 6.5 | 4.7 |
| Blocking | 0.01 mg/kg | | 5.9 | 4.66 |
| Baseline | | Male | 17.6 | 2.25 |
| Baseline | | | 17.8 | 4.45 |
| Blocking | 0.08 mg/kg | | 17.7 | 4.61 |
| Blocking | 0.01 mg/kg | | 17.4 | 4.48 |

Example 6

Compound 8F Pharmacokinetics in Rhesus Monkeys

Radioactivity concentrations in arterial plasma were measured up to 180 min following single i.v. doses of 2.25-4.99 mCi (83.25-184.63 MBq) Compound 8F in rhesus monkeys. Peak Compound 8F plasma concentrations of ~0.04% of the injected dose were achieved ~5 min post-dose. By ~10 min post-dose, plasma Compound 8F levels diminished to ~0.01% or less of the injected dose.

Example 7

Compound 8F Plama Protein Binding and Tissue Distribution in Rhesus Monkeys

The in vitro binding of Compound 8F to rhesus monkey plasma samples was determined using ultrafiltration in two separate studies. Compound 8F was found to be highly bound to plasma proteins with a plasma free fraction (not protein bound) of 4.7±0.6% in the first study and 0.8±0.04% in the second study.

Whole-body biodistribution and radiation dosimetry of Compound 8F was characterized in 2 rhesus monkeys by PET imaging following intravenous bolus injection of Compound 8F as outlined in Table 3.

TABLE 3

| Experiment type | Animal gender | Animal weight (kg) | Compound 8F Injected dose (mCi) |
| --- | --- | --- | --- |
| Whole-body dosimetry | Female | 5.6 | 9.93 |
| Whole-body dosimetry | Male | 18.1 | 9.53 |

Figure 6:
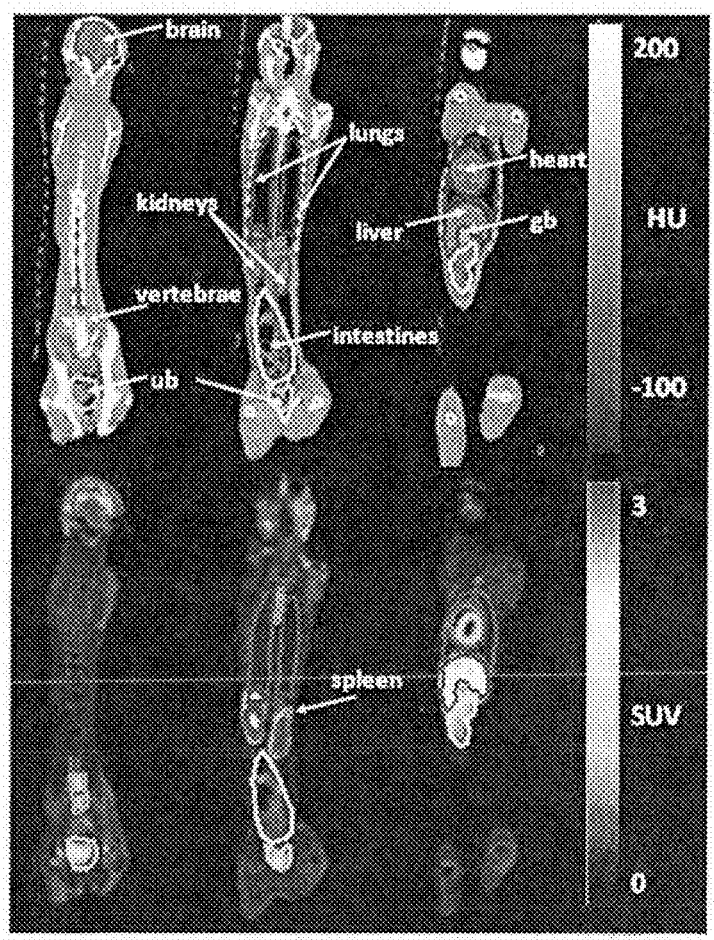
FIG. 6 depicts the tissue distribution in a rhesus monkey following intravenous bolus injection of Compound 8F showing computerized tomography (CT) (top panel) and positron emission tomography (PET) (bottom panel) images at three different levels through the body.
Figure 7:
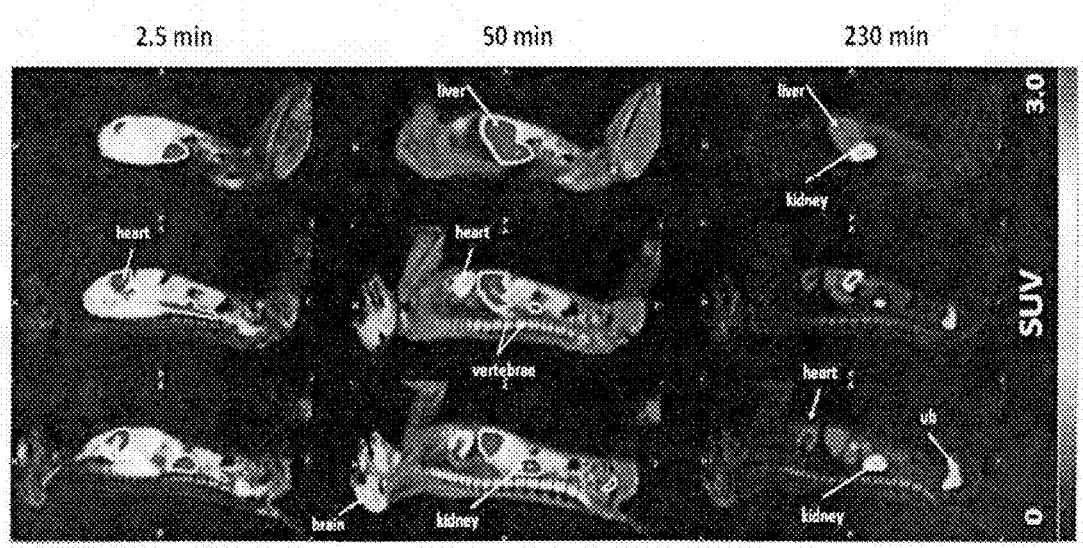
FIG. 7 depicts the tissue distribution in a rhesus monkey following intravenous bolus injection of Compound 8F showing PET images at three different time points.
Figure 8:
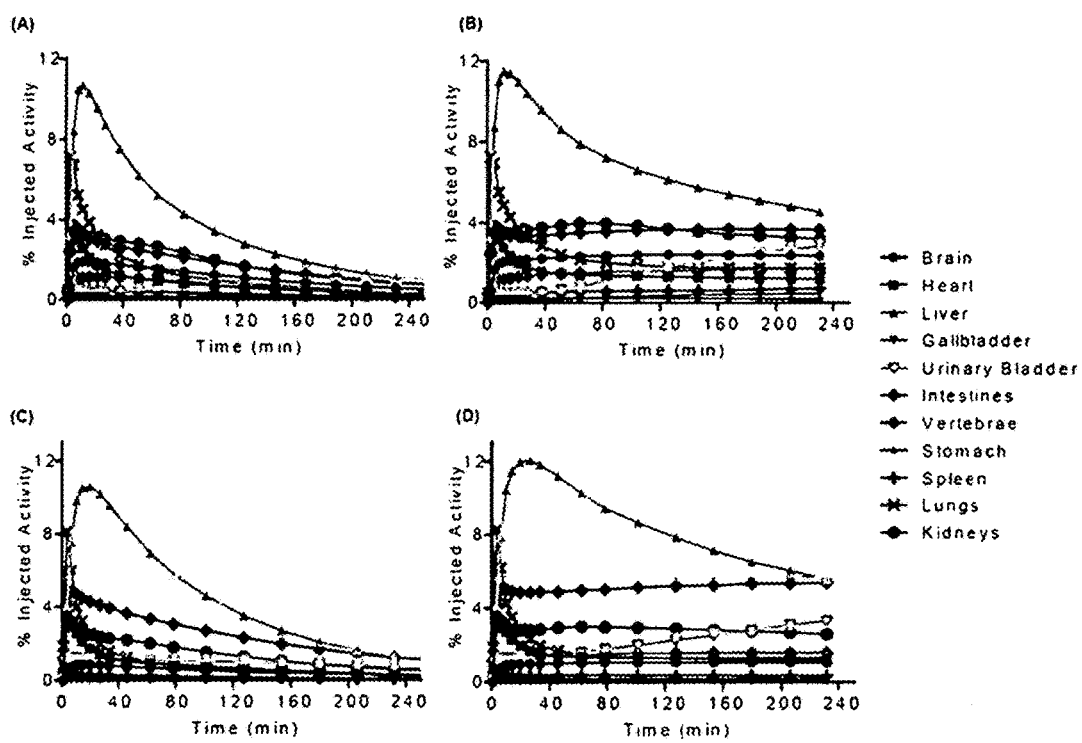
FIG. 8A-D depicts non-decay corrected and decay corrected time activity curves of 11 source organs following intravenous bolus injection of Compound 8F in both a female and male rhesus monkey.

Organs with the highest Compound 8F uptake included liver, heart wall, lungs, kidney and brain. The average PET image over the total acquisition duration (~240 min) of a female rhesus is shown in FIG. 6 (abbreviations: CT=computerized tomography; gb=gallbladder; HU=Hounsfield units; PET=positron emission tomography; SUV=standardized uptake value; ub=urinary bladder; VOI=volume of interest) at three different levels through the body. CT images in HU are displayed in the top panel. The average PET images in SUV units taken from 0-4 h are displayed in the bottom panel. The volumes of interest (VOIs) drawn over the organs identified as sources for the radiation dosimetry calculation can be seen on both average PET and its associated computed tomography (CT) image. A selection of images from the dynamic sequence of the same animal consisting of 3 different time points is shown in FIG. 7 to demonstrate the evolution of the activity concentration over time. Selected organs are labeled in the figure. The non-decay corrected (used for the dosimetry calculation) and decay corrected time activity curves of the 11 source organs are shown in FIG. 8 for both the female and male rhesus monkey. The curve values are expressed as percent of injected activity. The total absorbed doses in various target organs generated by OLINDA|EXM 1.1 software are presented in Table 4 for both adult male and adult female models in units of millisievert per megabecquerel (mSv/MBq) and roentgen equivalent man per millicurie (rem/mCi). Kidneys received the highest radiation dose in both the male and female rhesus. The effective dose equivalent (with ICRP-26 tissue weighting factors) and effective dose (with ICRP-60 tissue weighting factors) calculated for the whole body are also listed in Table 4.

TABLE 4

| | Dose (mSv/MBq) | | Dose (rem/mCi) | |
| --- | --- | --- | --- | --- |
| Target Organ | Female | Male | Female | Male |
| Adrenals | 1.81E-02 | 1.43E-02 | 6.69E-02 | 5.30E-02 |
| Brain | 1.84E-02 | 8.30E-03 | 6.82E-02 | 3.07E-02 |
| Breasts | 1.06E-02 | 8.31E-03 | 3.91E-02 | 3.07E-02 |
| Gallbladder Wall | 3.14E-02 | 1.89E-02 | 1.16E-01 | 7.01E-02 |
| LLI Wall [a] | 1.68E-02 | 1.61E-02 | 6.23E-02 | 5.97E-02 |
| Small Intestine | 2.53E-02 | 2.72E-02 | 9.37E-02 | 1.01E-01 |
| Stomach Wall | 1.65E-02 | 1.21E-02 | 6.12E-02 | 4.49E-02 |
| ULI Wall [b] | 2.72E-02 | 2.92E-02 | 1.01E-01 | 1.08E-01 |
| Heart Wall | 3.96E-02 | 3.32E-02 | 1.46E-01 | 1.23E-01 |
| Kidneys | 7.48E-02 | 5.62E-02 | 2.77E-01 | 2.08E-01 |
| Liver | 3.77E-02 | 3.31E-02 | 1.39E-01 | 1.22E-01 |
| Lungs | 3.47E-02 | 2.25E-02 | 1.28E-01 | 8.31E-02 |
| Muscle | 1.17E-02 | 9.50E-03 | 4.31E-02 | 3.51E-02 |
| Ovaries | 1.51E-02 | 1.35E-02 | 5.59E-02 | 4.98E-02 |
| Pancreas | 1.75E-02 | 1.44E-02 | 6.48E-02 | 5.33E-02 |
| Red Marrow | 1.64E-02 | 1.49E-02 | 6.08E-02 | 5.50E-02 |
| Osteogenic Cells | 2.17E-02 | 1.64E-02 | 8.02E-02 | 6.08E-02 |
| Skin | 8.70E-03 | 7.02E-03 | 3.22E-02 | 2.60E-02 |
| Spleen | 2.78E-02 | 3.43E-02 | 1.03E-01 | 1.27E-01 |
| Testes | | 8.57E-03 | | 3.17E-02 |
| Thymus | 1.41E-02 | 1.13E-02 | 5.23E-02 | 4.17E-02 |
| Thyroid | 1.04E-02 | 8.79E-03 | 3.86E-02 | 3.25E-02 |

TABLE 4-continued

| Target Organ | Dose (mSv/MBq) | | Dose (rem/mCi) | |
|---|---|---|---|---|
| | Female | Male | Female | Male |
| Urinary Bladder Wall | 3.73E-02 | 3.72E-02 | 1.38E-01 | 1.38E-01 |
| Uterus | 1.52E-02 | 1.37E-02 | 5.61E-02 | 5.07E-02 |
| Total Body | 1.38E-02 | 1.11E-02 | 5.12E-02 | 4.12E-02 |
| Effective dose equivalent | 2.57E-02 | 2.15E-02 | 9.51E-02 | 7.95E-02 |
| Effective dose | 2.06E-02 | 1.70E-02 | 7.61E-02 | 6.28E-02 |

[a] Lower large instestine
[b] Upper large intestine

Example 8

Compound 8F Pharmacokinetics, Metabolism, and Distribution in Humans

Compound 8F was evaluated in a single clinical Phase 0 study to evaluate its brain uptake, whole-body biodistribution and safety in healthy volunteers age 18-55 years. Five healthy male volunteers were recruited into a dynamic PET brain imaging cohort and each subject underwent two Compound 8F PET scans: a baseline session and a follow-up imaging session between 3 days and 3 weeks following the baseline scan. An additional cohort of four healthy volunteers (two male, two female) was recruited for a whole body biodistribution cohort in which they underwent a single Compound 8F PET scan. Administered single Compound 8F doses ranged from 6.39-9.01 mCi, (236.43-333.37 MBq), and single tracer mass doses ranged from 0.66-2.49 μg.

Blood samples were analyzed by HPLC to determine the fraction of intact parent compound at each time point. Compound 8F was stable in blood ex vivo. Approximately 30% of parent compound could be found in the plasma at 90 min post injection after which Compound 8F was slowly metabolized. Free fraction of parent compound in plasma (not protein bound) was also measured by ultrafiltration and estimated to be 0.36±0.04% (n=10).

In the whole-body biodistribution cohort, the elimination of the radiotracer was primarily hepatobiliary, with a maximum of 26-28% injected dose (ID) in the liver and 6-7% ID in the intestine. The liver was found to be the organ with highest radiation absorbed dose (critical organ). Elimination via the urinary route was very low.

There was good brain uptake in all gray matter regions, with tracer distribution in the brain in accordance with the expected MGLL distribution. Compound 8F was moderately metabolized with about 30% remaining at 90 min post injection after which the parent fraction varied slowly up to 120 min.

Whole body biodistribution, radiation absorbed dose and effective dose for several organs and total body of Compound 8F were evaluated in 2 female and 2 male subjects. The following organs were identified as source organs: brain, heart, liver, gallbladder, intestines, kidneys, and urinary bladder. Analysis of the time-activity curves showed that the tracer was eliminated primarily via hepatobiliary route. The average whole body effective dose (ED) was determined to be 2.19E-02±2.83E-04 mSv/MBq (8.10E-02±1.05E-03 rem/mCi) for adult female and 1.85E-02±7.07E-04 mSv/MBq (6.85E-02±2.62E-03 rem/mCi) for adult male, where the critical organ was determined to be the liver. Stated differently, average whole body ED for females=21.9 μSv/MBq, and for males=18.5 μSv/MBq (average for male and female=20.2 μSv/MBq).

Example 9

A Phase 1 Study to Evaluate MGLL Enzyme Occupancy Using Compound 8F PET Brain Imaging Before and after Oral Administration of Compound 9 to Healthy Volunteers General Design and Methodology: The primary goal of this study was to evaluate dose- and concentration-dependent brain MGLL enzyme occupancy kinetics of single oral doses of Compound 9 HCl, an orally-available, covalent inhibitor of MGLL, by using MGLL-specific radiotracer, Compound 8F. In preclinical species, the extent of brain MGLL occupancy was positively associated with the efficacy of therapeutic candidate compounds, and it was expected that human brain occupancy data will form a critical component of human dose selection of Compound 9 HCl, and potentially other clinical candidate MGLL inhibitors. The PET scanning procedures to achieve this goal are well-established at the clinical site where this study was conducted, and are described in detail in this protocol. As shown in Example 5, the ability of Compound 9 to occupy brain MGLL enzyme in a dose-related fashion has been established preclinically in a non-human primate PET study. Furthermore, as shown in Example 8, Compound 8F has undergone initial clinical evaluation and the dosing and scanning parameters evaluated were incorporated into the current study design.

For this initial clinical evaluation of brain MGLL enzyme occupancy (EO), PET scans were conducted after the administration of single oral doses of Compound 9 HCl. For this initial evaluation of brain MGLL EO, PET scans were planned to coincide with the approximate $T_{max}$ of orally-administered Compound 9 HCl, and at the anticipated $C_{trough}$ (assuming a QD dosing regimen). Data emerging from this study may indicate the need for subsequent brain MGLL EO evaluation at different timepoints in relation to Compound 9 HCl dosing.

Peripheral (i.e., non-CNS) dose-dependent MGLL enzyme inhibition in PBMC can be measured both preclinically and in healthy human subjects who have been administered oral doses of Compound 9 HCl. These techniques were applied in the current study in order to compare, in an exploratory fashion, MGLL EO in the brain (as measured by PET scanning) with PBMC MGLL inhibition (as measured by a PBMC substrate hydrolysis assay).

The safety and tolerability of both Compound 9 HCl and Compound 8F were evaluated by standard adverse event monitoring, along with evaluation of vital signs, laboratory safety tests, ECG measurement, and physical examination (including neurological examination).

Primary Objectives.
1) To evaluate the brain MGLL enzyme occupancy kinetics of single oral doses of Compound 9 HCl using the PET-tracer, Compound 8F.
   Outcome measure: The oral dose of Compound 9 HCl required for 50% brain MGLL enzyme occupancy at the $C_{max}$ of Compound 9 using Compound 8F PET tracer will be estimated.
2) To evaluate the relationship between Compound 9 plasma concentrations and brain MGLL enzyme occupancy using the PET tracer Compound 8F in healthy volunteers.

Outcome measure: The plasma concentration of Compound 9 associated with 50% occupancy of brain MGLL enzyme as measured by the PET tracer Compound 8F will be estimated.

Secondary Objectives:
1) To evaluate the safety and tolerability of Compound 9 after administration of single oral doses of Compound 9 HCl to healthy adult subjects.
2) To evaluate the safety and tolerability of Compound 8F after administration of single intravenous doses of Compound 8F to healthy adult subjects.

Exploratory Objective: To explore the relationship between MGLL target engagement in the periphery (as measured in a PBMC MGLL substrate assay) versus that in the CNS (as measured by PET brain MGLL enzyme occupancy) after administration of single oral doses of Compound 9 HCl to healthy adult subjects.

Study Design

This was an open-label Phase 1 study in which subjects received a single oral dose of Compound 9 HCl, and three i.v. doses of Compound 8F. Subjects underwent PET brain scanning in association with each dose of Compound 8F.

All subjects underwent a single T1-weighted volumetric anatomic MRI brain scan in order to confirm study eligibility, and for anatomic reference and volume of interest (VOI) placement. Each subject underwent 3×PET-CT scans following i.v. administration of Compound 8F, with a low-dose CT scan for attenuation correction purposes (approximately 18 mAs, 0.05 mSv radiation burden). The first PET scan (baseline enzyme occupancy (EO)) was conducted 3 to 21 days prior to Compound 9 HCl dose. The second PET scan was timed to capture the EO at the $T_{max}$ of orally-administered Compound 9 HCl (i.e. starting at approximately 2 hours post-dose), and the third PET scan was timed to capture EO approximately 24 hours after Compound 9 HCl administration. For the first (baseline) PET scan, an arterial cannula was placed and removed after completion of the scanning procedures. For the second and third PET scans, an arterial cannula was placed prior to the conduct of the second scan, and maintained in place until the completion of the third scan.

Subjects were domiciled in the clinical research unit overnight prior to the administration of Compound 9 HCl oral dose, and again overnight after the administration of Compound 9 HCl (i.e. between the second and third PET scans). Subjects were not domiciled overnight prior to or following the first (baseline) scan. Table 5 depicts the overall study design.

TABLE 5

| Visit 1 | Screening Procedures <4 weeks before Visit 2; includes baseline MRI if necessary |
| Visit 2 | Baseline PET scan (outpatient) ≤4 weeks after Visit 1 |
| Visit 3 | Admitted to CRU; Compound 9 HCl administration and PET occupancy scans performed 3-21 days after baseline PET scan |
| Visit 4 | Post-study visit at least 14 days after last dose of Compound 9 |

The doses of Compound 9 HCl evaluated in this study ranged from 10 mg-60 mg (inclusive). All subjects received a single oral dose of Compound 9 HCl in an unblinded fashion. In addition, all subjects received three intravenous doses of Compound 8F, with each dose administered in the context of a PET brain scan. The first two subjects enrolled in this study were administered, in the fasted state, Compound 9 HCl doses of 10 mg and 40 mg respectively. After the PET scans for these two subjects were completed, preliminary occupancy data was evaluated to determine the sequence of subsequent Compound 9 doses within the anticipated 10 mg-60 mg dose range. It was intended to evaluate approximately three subjects at each Compound 9 HCl dose level—14 subjects in total were evaluated for these doses.

Since this was a Phase 1 assessment of Compound 9 HCl and Compound 8F in humans, and given that pharmacokinetic, pharmacodynamic and safety profiles of the compounds are still being evaluated, this protocol was written with some flexibility to accommodate the inherent dynamic nature of Phase 1 clinical trials.

Criteria for Inclusion:

A) Subject understands the study procedures and agrees to participate in the study by giving written informed consent.

B) is a male, or female (not of reproductive potential) 18 to 60 years of age at the pre-study/screening visit; further:
(1) If subject is a postmenopausal female: subject is without menses for at least 1 year and has a documented follicle stimulating hormone (FSH) level in the postmenopausal range at pretrial (screening).
(2) If subject is a surgically sterile female: subject is status post hysterectomy, bilateral oophorectomy, or bilateral tubal ligation. (Hysterectomy may be confirmed by ultrasound or other imaging technique if documentation is not available. Oophorectomy and tubal ligation must be confirmed by documentation).

C) Subject has a Body Mass Index (BMI)>18 to ≤32 kg/m² at the pre-study/screening visit. BMI=weight (kg)/height (m)² (BMI calculation should be rounded to the nearest whole number).

D) Subject is judged to be in good health based on medical history, physical examination, and vital sign measurements, and laboratory safety tests obtained at pre-study/screening, and within 24 hours prior to first administration of study drug.

E) Subject has no clinically significant abnormality of electrocardiography (ECG) performed at pre-study/screening, and prior to first administration of study drug.

F) Subject is a nonsmoker and/or has not used nicotine or nicotine-containing products (e.g., nicotine patch) for at least approximately 3 months.

G) Subject is willing to comply with the study restrictions.

Criteria for Exclusion:

A) Subject is under the age of legal consent.

B) Subject has a personal history of a clinically significant psychiatric disorder (including severe affective disorder, psychotic tendencies and drug-induced psychoses). Subjects who have had situational depression or anxiety in the past may be enrolled at the discretion of the investigator.

C) Subject has a first-degree family history of schizophrenia, major affective disorder, major anxiety disorder, or other psychosis.

D) Subject is mentally or legally incapacitated, has significant emotional problems at the time of pre-study/screening visit or is expected to have potential for mental incapacitation during the conduct of the study.

E) Subject has a history of any illness that, in the opinion of the study investigator, might confound the results of the study or pose an additional risk to the subject by virtue of their participation in the study.

F) Subject has an estimated creatinine clearance (CrCl) of ≤80 mL/min based on the Cockcroft-Gault equation. An actual creatinine clearance, as measured using a 24-hour urine collection, may be used in place of, or in conjunction with the Cockcroft-Gault calculation. Subjects with an actual or calculated creatinine clearance that is in the range of 72-79 mL/min (i.e., within 10% of 80 mL/min) may be enrolled in the study at the discretion of the investigator. Cockcraft-Gault Equation:

$$CrCl=(140\text{-age [yr]})*(\text{body weight [kg]})/(72) \text{ serum creatinine [mg/dL]})$$

For female subjects, multiply by 0.85 to obtain creatinine clearance.

G) Subject has an active or prior history of neurological disorder, including but not limited to seizure disorder, epilepsy, stroke, neurological disease, cognitive impairment, head trauma with prolonged loss of consciousness (>10 minutes), or migraine headaches.

H) Subject has a history of clinically significant endocrine, gastrointestinal, cardiovascular, peripheral vascular, hematological, hepatic, immunological, renal, respiratory, or genitourinary abnormalities or diseases. Subjects with a history of uncomplicated kidney stones (defined as spontaneous passage and no recurrence in the last 5 years), or childhood asthma may be enrolled in the trial at the discretion of the investigator.

I) Subject has a history of clinically significant neoplastic disease, with the exception of adequately treated localized or in situ non-melanoma carcinoma of the skin (i.e., basal cell carcinoma) or the cervix.

J) Subject has a history of significant multiple and/or severe allergies (e.g., food, drug, latex allergy), or has a history of significant allergy to lidocaine (or other local anesthetics that may be used during arterial cannula placement), or has had an anaphylactic reaction or significant intolerability to prescription or non-prescription drugs (including marijuana or other *cannabis*-containing drugs) or food.

K) Subject has had major surgery, donated or lost 1 unit (approximately 500 mL) of blood, or has participated in another investigational trial within 4 weeks prior to the pre-study/screening visit. The 4 week window is derived from the date of the last trial medication and/or blood collection in a previous trial and/or adverse event (AE) related to trial drug to the pretrial/screening visit of the current trial. For subjects who have participated in an investigational trial where no trial drug was administered or invasive procedure performed the interval may be revised to include no interval requirement.

L) Subject has had (within 8 weeks of pre-study/screening visit) or plans to have a preventive vaccination during the course of the study (i.e., up to the post-study visit).

M) Subject is unable to refrain from or anticipates the use of any medication, including prescription and non-prescription drugs or herbal remedies (such as St. John's Wort [*Hypericum perforatum*]) beginning approximately 2 weeks (or 5 half-lives) prior to administration of the initial dose of study drug, throughout the study (including washout intervals between treatment periods), until the post-study visit. There may be certain medications that are permitted.

N) Subject was treated in the preceding 6 months with antidepressants, neuroleptics, sedative hypnotics, psychostimulants, glucocorticoids, appetite suppressants, opiate, cannabinoid, or dopamine medications. Subjects on female hormone replacement therapy in the preceding 6 months may be enrolled provided the hormone therapy is discontinued approximately 2 weeks prior to the dose of Compound 9 HCl.

O) Subject consumes excessive amounts of alcohol, defined as >3 servings of alcoholic beverages per day (1 serving is approximately equivalent to: 300 mL [10 ounces] of beer, 125 mL [4 ounces] of wine, 25 mL [1 ounce] of distilled spirits). Subjects that consume no more than 4 servings of alcoholic beverages per day may be enrolled at the discretion of the investigator.

P) Subject consumes excessive amounts of caffeine, defined as >6 servings of coffee, tea, cola, or other caffeinated beverages per day (1 serving is approximately equivalent to 120 mg of caffeine).

Q) Subject is currently (defined as within approximately 3 months of the pre-study/screening visit) a regular user (including "recreational use") of any illicit drugs (including marijuana) or has a history of drug (including alcohol) abuse within approximately 6 months of the pre-study/screening visit. Subjects must have a negative urine drug screen prior to treatment allocation.

R) Subject has had exposure to ionizing radiation of more than 1 mSv in other research studies within the last 12 months.

S) Subject suffers from claustrophobia during PET and MRI scanning procedures.

T) For male subjects: Subject is unwilling or unable to use a condom with female sexual partners from the time of first administration of study drug through three months after the final dose of study drug.

U) For male subjects: Subject is unwilling to refrain from sperm donation from the time of first administration of study drug through three months after the final dose of study drug.

V) Subject has a family history of long QT syndrome.

W) Subject has a QTc interval of >450 msec (male subjects) or >470 msec (female subjects). Measurement is based on mean of triplicate ECGs obtained at baseline.

X) The investigator has concerns regarding the safe participation of the subject in the study or for any other reason the Investigator considers the subject inappropriate for participation in the study. For example: subject has any disease or condition, subject has a clinically significant abnormality/abnormalities observed on the MRI scan performed prior to PET scanning, or subject takes any medication, which, as judged by the investigator, could (a) interfere with the assessments of safety, tolerability, or biokinetics of the tracer, or (b) pose unnecessary risk to the subject, or (c) cause undue discomfort (e.g., subject with chronic low back pain who would not be comfortable lying still on an imaging table).

Y) Subject has an abnormal Allen test at the screening physical examination (i.e., adequate ulnar arterial patency cannot be demonstrated in one of the wrists).

Z) Subject has implanted or embedded metal objects, or fragments in the head or body that would present a risk during the magnetic resonance imaging (MRI) scanning procedure, or has worked with ferrous metals either as a vocation or hobby (for example, as a sheet metal worker, welder, or machinist) in such a way that might have led to unknown, indwelling metal fragments that could cause injury if they moved in response to placement in the magnetic field.

Investigational Product, Dosage and Mode of Administration: Investigational drug product, hydrochloride salt of Compound 9, is a formulated powder blend of 2-, 10-, or 50-mg strength, filled into a Size #2 Swedish Orange gelatin capsule with no markings. Each strength of study drug was packaged in appropriately labeled 30-count high-density polyethylene (HDPE) plastic bottles with child-resistant, induction-sealed closures.

Study drugs were administered by qualified study personnel who ensured that the study drugs were administered only according to the assigned schedule. Selection of each Compound 9 HCl dose after the administration of the first two doses was based on review of available PET and safety data by the study investigators and the Sponsor. Dose selection was confirmed by a Sponsor-authored memo that was submitted to study investigators and the study pharmacist prior to each administration of Compound 9 HCl dose.

For all Compound 9 HCl doses, study drug was administered after an overnight fast (for approximately 8 hours). Since the scanning procedures were not conducted early in the day, subjects received their dose of Compound 9 HCl at approximately 10 am to 12 noon prior to afternoon scanning procedures. Given the duration of the scanning procedures, a strict overnight fast prior to administration of Compound 9 HCl was not feasible. Accordingly, subjects received a light, low-fat meal in the morning prior to Compound 9 HCl administration, provided this meal was completed at least 4 hours prior to the Compound 9 HCl dose. The contents of this meal were agreed upon by the Sponsor and the Investigator, and were the same for all subjects. All doses were taken orally with approximately 240 mL of water, with water otherwise restricted 1 hour prior to and 1 hour after study drug administration.

Investigational Radiopharmaceutical, Dosage and Mode of Administration: Given the short half-life of $^{18}F$ (109.8 min), Compound 8F was radiolabelled, purified and formulated when required for administration to human subjects according to pre-specified radiopharmaceutical manufacturing and quality assurance procedures that conform to accepted standards in the field.

The dose of radiotracer (Compound 8F) was drawn-up in a sterile disposable syringe and measured in a dose calibrator in a laminar airflow cabinet by qualified personnel of the radiopharmacy department prior (<30 min) to injection into the subject. The syringe was placed in a tungsten syringe shield and transported in a lead shielded trolley labeled with a color coded label stating the name of the product (Compound 8F), the dose (in MBq) and the time of measurement. The dose was immediately transported by qualified personnel of the radiopharmacy department to the PET camera room where it is transferred directly to the person charged with the intravenous injection. After injection, the residual activity in the syringe and administration tubing was measured and the syringe and tubes were discarded. The dose, residual dose and time measurement and specific activity were recorded on a dose form.

Compound 8F was administered by a single intravenous injection of not more than 160 MBq (not more than 10 µg mass dose/3.2 mSv radiation burden). Human test-retest studies indicated that this dose gives sufficient Compound 8F brain EO with acceptable signal-to-noise ratio, allowing direct measurements of its dynamic regional cerebral concentration.

Procedures for Screening (Visit 1): A signed and dated informed consent form was obtained before screening procedures are performed. Evaluations obtained as part of routine medical care and performed during the screening period were used in place of the study specific evaluations. Subjects acknowledged and agreed to the possible use of this information for the study by giving informed consent.

A screening visit took place not more than 4 weeks before the visit for the baseline PET scan. The following procedures were performed:
  informed consent
  inclusion/exclusion criteria
  medical/psychiatric history
  medication history
  weight, height, respiration rate and body temperature (oral or tympanic)
  physical examination (with full neurological examination, and Allen test for ulnar artery patency)
  vital signs (semi-recumbent for at least 5 minutes blood pressure and heart rate), and resting 12-lead ECG
  urine drug screen (UDS), mandatory
  safety laboratory tests: hematology (including PT/INR and PTT), chemistry, urinalysis
  FSH (as needed, female subjects only)
  the following screening evaluations may be performed at the discretion of the Investigator: hepatitis C antibodies, hepatitis B surface antigen (HBsAg), and HIV testing
  Baseline MRI scan. All subjects underwent a volumetric T1-weighted anatomic MRI brain scan along with either T2-weighted or (3D) FLAIR imaging in order to confirm study eligibility, and for anatomic reference and volume of interest (VOI) placement. No gadolinium was injected prior to obtaining the MRI. This scan was scheduled to occur after visit 1 but prior to visit 2. Subjects who have undergone an appropriate MRI brain scan within one year of the screening visit were required to undergo baseline MRI scanning.
  Procedures for Baseline PET Scan (Visit 2):
  Baseline/initial PET scan was to be conducted no more than 4 weeks after the screening visit screening visit. Subjects who meet the inclusion/exclusion criteria at the screening visit were admitted to the clinical research unit on the morning of the planned scan, and underwent the following evaluations prior to transfer to the PET imaging unit:
    inclusion/exclusion review
    medication history review
    ECG (Visit 2 baseline, in triplicate), vital signs (including respiratory rate and temperature).
    physical examination (with targeted neurological exam)
    urine drug screen
    safety laboratory tests
    adverse event inquiry For the Compound 8F imaging session an intravenous catheter was placed for administration of Compound 8F and an arterial cannula was placed for arterial blood sampling. Compound 8F was formulated in sterile, non-pyrogenic solution for intravenous administration containing ethanol, ascorbic acid, sodium acetate, and sodium chloride in water for injection. Subjects received a single i.v. bolus administration of up to 160 MBq of Compound 8F with a volume not exceeding 10 mL, and mass dose not exceeding 10 µg followed by a normal saline flush, prior to each imaging session. The radiopharmaceutical Compound 8F was prepared by the UZ Leuven radiochemistry synthesis laboratory under GMP conditions. Once the radiopharmaceutical passed quality control procedures it was dispensed to the PET imaging suite, using standard operating procedures for production, transfer, and administration of radiopharmaceutical. The radiopharmaceutical dose was administered shortly after delivery to the PET imaging suite.

Immediately following the injection, continuous dynamic brain scan occurred for a period of 3.5 hours with intermittent breaks. The duration and timing of breaks were adjusted based on individual subject acceptability and tolerability. Arterial sampling (1.5 to 5 mL/sample) occurred throughout the duration of the imaging to facilitate pharmacokinetic modeling. The image data that was collected up to that point was analyzed.

Adverse events were continuously monitored during the Compound 8F imaging session.

Subjects were evaluated for adverse events prior to discharge from the imaging center. Subjects who experienced an adverse event were discharged from the imaging center until the event was resolved or stabilized.

Procedures Before Compound 9 Administration and PET Occupancy Scans (Visit 3):

The administration of Compound 9 HCl and associated PET occupancy scans occurred 3-21 days after the baseline PET scan. Study procedures were completed as close to the prescribed/scheduled time as possible. The blood sample for Compound 9 plasma concentration (PK) was the critical procedure of this study and was collected as close to the exact time point as possible.

Subjects who met the inclusion/exclusion criteria at the screening visit and who successfully completed the baseline PET scan were admitted to the clinical research unit on Day −1, and underwent the following evaluations:
 inclusion/exclusion review
 medication history review
 physical examination (with targeted neurological exam)
 urine drug screen
 safety laboratory tests
 adverse event inquiry Since the scanning procedures were not conducted early in the day, subjects received their dose of Compound 9 HCl at approximately 10 am to 12 noon prior to afternoon scanning procedures. Given the duration of the scanning procedures, a strict overnight fast prior to administration of Compound 9 HCl was not feasible. Accordingly, subjects received a light, low-fat meal in the morning prior to Compound 9 HCl administration, provided this meal was completed at least 4 hours prior to the Compound 9 HCl dose. The contents of this light meal were agreed upon by the Sponsor and the Investigator, and were the same for all subjects. All doses were taken orally with approximately 240 mL of water, with water otherwise restricted 1 hour prior to and 1 hour after study drug administration.

Procedures for Compound 9 Administration and PET Occupancy Scans (Visit 3 Continued):

Prior to administration of Compound 9 HCl: Adverse event inquiry occurred at 0 hour (pre-dose) and at each visit throughout the study, up to and including the post-study visit (at least 14 days after the last dose of study drug):
 0-hr (pre-dose) blood for plasma Compound 9, plasma 2-AG (archive), and PBMC MGLL TE assays was drawn (after placement of an intravenous catheter)
 temperature/respiration rate
 vital signs and 12-lead ECG (Visit 3 baseline, in triplicate).

Administration of Compound 9 HCl: Compound 9 HCl administration occurred approximately 2 hours prior to the intended start of the PET imaging procedures (defined as 0-hour). The actual time of dosing was determined by the clinical site, and maintained (within an approximately one hour window) throughout the study. All Compound 9 HCl doses were administered orally, together with approximately 240 mL of water. Water was otherwise be restricted from 1 hour prior to, and for 1 hour after administration of study drug:
 Approximately 1 hour after Compound 9 HCl dose:
  i. 1-hr (post-dose) blood for plasma Compound 9 and plasma 2-AG (archive) assays were drawn
  ii. temperature/respiration rate
  iii. vital signs and 12-lead ECG
 Approximately 2 hours after Compound 9 dose (immediately prior to injection of Compound 8F):
  i. 2-hr (post-dose) blood for plasma Compound 9, plasma 2-AG (archive) assays, and PBMC MGLL TE assays were drawn Prior to administration of Compound 8F: An intravenous catheter was placed for i.v. administration of Compound 8F and an arterial catheter placed in a radial artery for blood sampling for evaluation of radiolabeled metabolites.

Administration of Compound 8F and first PET occupancy scan occurred approximately 2 hours following Compound 9 dose:
 Subjects received an i.v. injection of up to 160 MBq (not more than 10 µg mass dose and 3.2 mSv radiation burden) of Compound 8F tracer. Immediately following the injection, continuous dynamic brain scanning occurred for a period of 3.5 hours with intermittent breaks. Arterial sampling (1.5 to 5 mL/sample) occurred throughout the duration of the imaging to facilitate pharmacokinetic modeling. If at any point during the imaging session it was determined that the subject was not able to continue, or that it was not in the best interest of the subject to continue, imaging was discontinued. The image data that has been collected up to that point was analyzed. Adverse events were continuously monitored during the Compound 8F imaging session.
 During one of the imaging breaks (approximately 3.5-4-hr after Compound 9 HCl dose) blood for plasma Compound 9, plasma 2-AG (archive), and PBMC MGLL TE assays was drawn
 At the completion of the imaging session (approximately 5.5 hr after Compound 9 HCl dose):
  i. blood for plasma Compound 9, plasma 2-AG (archive), and PBMC MGLL TE assays was drawn
  ii. temperature/respiration rate
  iii. vital signs and 12-lead ECG
  iv. arterial cannula remained in place and subject may return to the clinical unit for overnight domicile
 Approximately 24 hours after Compound 9 HCl dose (immediately prior to second injection of Compound 8F):
  i. 24-hr (post-dose) blood for Compound 9, plasma 2-AG (archive) assays, and PBMC MGLL TE assays was drawn
  ii. temperature/respiration rate
  iii. vital signs and 12-lead ECG Administration of Compound 8F and second PET occupancy scan occurred approximately 24 hours following Compound 9 HCl dose:
 Subjects received an i.v. injection of up to 160 MBq (not more than 10 µg mass dose and 3.2 mSv radiation burden) of Compound 8F tracer. Immediately following the injection, continuous dynamic brain scanning occurred for a period of 3.5 hours with intermittent breaks. Arterial sampling (1.5 to 5 mL/sample) will occur throughout the duration of the imaging to facilitate pharmacokinetic modeling. If at any point during the imaging session it was determined that the subject was not able to continue, or that it was not in the best interest of the subject to continue, imaging was discontinued. The image data that has been collected up to that point was analyzed. Adverse events were continuously monitored during the Compound 8F imaging session.
 At the completion of the imaging session (approximately 27.5 hr after Compound 9 HCl dose):
  i. blood for plasma Compound 9, plasma 2-AG (archive), and PBMC MGLL TE assays was drawn ii. safety laboratory tests
iii. temperature/respiration rate
iv. vital signs and 12-lead ECG
v. physical examination with targeted neurological examination to determine fitness to return home
vi. arterial cannula was removed and subject discharged to home Post-Study (Visit 4):

The following procedures were performed at Post-Study visit (scheduled at least 14 days after last dose of study drug):

physical examination (with full neurological examination)
urine drug screen
weight
vital signs and 12-lead ECG
temperature and respiration rate
safety laboratory tests
adverse event inquiry
concomitant medications inquiry Procedures for PET Scanning Subjects underwent three Compound 8F brain PET-CT imaging sessions over two study visits. The first PET scan session was to capture baseline brain MGLL EO. The second and third PET scan sessions occurred after administration of a single oral dose of Compound 9 HCl (one to start approximately 2 hours, and one approximately 24 hours after the Compound 9 HCl dose).

A low-dose head CT transmission scan (0.05 mSv radiation burden) was acquired before injection of the radiopharmaceutical for subsequent attenuation correction. Emission scans were corrected for attenuation, scatter, random events, and dead-time.

Upon transfer to the scanning room, subjects were familiarized with the environment. All subsequent procedures were explained to minimize anticipatory anxiety and/or fear that may affect cerebral blood flow. For each scan, subjects were positioned on the scanner bed with the head within the center of axial and transaxial field of views. The subject's head was placed in a head holder and fixed using a vacuum cushion to avoid excessive head movements during the scan. Baseline sensory conditions (dimmed room lighting, reduced noise) were imposed and maintained through the PET scans. For each Compound 8F imaging session an intravenous catheter was placed for administration of Compound 8F and an arterial cannula for arterial blood sampling. Subjects received a single i.v. injection of up to 160 MBq (not more than 10 μg mass dose/3.2 mSv radiation burden) Compound 8F. Immediately following the injection, serial dynamic imaging (6×30 sec, 4×1 min, 4×2 min, 15×5 min over first hour and a half, then 10 min PET frames in segment 2 and 3) was obtained over a total duration of up to 3.5 hours. Arterial sampling (up to 21 samples) was obtained during the course of the imaging including: up to 6 samples of 5 mL of blood (metabolite analysis) and up to 15 of 1.5 mL of blood (activity concentration) was sampled for radioactive metabolite analysis to determine the concentration and percent parent fraction of Compound 8F in plasma over time.

Dynamic brain PET images created on the PET camera were transferred to a dedicated PMOD workstation for image analysis together with the volumetric T1 images. The primary imaging outcome for Compound 8F was the total distribution volume Vt. Vt was calculated in regions with an expected high MGLL enzyme activity including the putamen, and also obtained in regions with expected high to moderate (hippocampus, frontal, occipital, parietal, and temporal lobes, cingulate) as well as low MGLL enzyme activity (brainstem in particular).

Arterial sampling (up to 21 samples, 1.5 to 5 mL/sample, see above) occurred throughout the duration of the imaging to facilitate pharmacokinetic modeling. If at any point during the imaging session it was determined that the subject is not able to continue, or that it was not in the best interest of the subject to continue, imaging was discontinued. The image data that has been collected up to that point was analyzed. The arterial catheter was removed at the completion of imaging.

The individual's MRI and PET images were co-aligned for anatomy-based definition of VOIs for analysis of regional Compound 8F EO. An automatic VOI template (Hammers Atlas) was used for reproducible volume-of-interest definition. Imaging data were analyzed using irreversible kinetic models as used for previously collected clinical data with Compound 8F.

Adverse events were continuously monitored during the Compound 8F imaging sessions.

Individual subjects were scanned a total of 4 times (3×PET (with low-dose CT head), 1×T1 anatomic MRI) within a period of several weeks (maximum approximately 9 weeks). A maximum of 7 visits (including screening and post-study) were required.

Pharmacokinetic and Pharmacodynamic Assessments:

A single blood sample was taken at each timepoint for quantitation of plasma Compound 9 concentrations and for potential quantitation of plasma 2-AG concentrations. Dose-related changes in plasma 2-AG concentrations, if assayed, were evaluated as an exploratory endpoint. At each sampling time point, one 4-mL blood sample was collected from each subject by venipuncture or indwelling catheter; the exact sampling time was recorded on the eCRF. Whole blood samples were drawn into tubes with anticoagulant additive and were inverted slowly 6 to 8 times to mix the contents and placed in an ice bath and delivered to the laboratory. The whole blood specimens were immediately grouped and placed into a refrigerated centrifuge. If the technician was unable to spin the specimens immediately, they were placed in an ice bath or the laboratory refrigerator until such time as centrifugation was initiated. Blood samples were centrifuged (at 3000 revolutions per minutes (rpms), for 15 minutes at 4° C.). For each sample collected, separated plasma were transferred into three labeled polypropylene tubes: 0.65 mL plasma into each of the first and second tubes, and the remaining plasma into the third tube. Samples were then frozen in an upright position and stored at a maximum of −20° C. until shipped for analysis.

Blood samples for determination of plasma Compound 9 concentrations were obtained at pre-dose and at various timepoints post-dose, as indicated below and on the study flow chart. Plasma samples for the quantitation of 2-AG concentrations were collected at the same time, and in the same blood collection tube as each PK sample. Following quantification of Compound 9 plasma concentrations, some of the remaining plasma was pooled and archived for metabolite scouting (i.e. qualitative evaluation of the presence of Compound 9 metabolites).

Compound 9 plasma concentrations were measured prior to treatment (0 hour) and at the following time points after administration of study drug at times: 1, 2 (prior to tracer injection), 3.5-4 (midway through first PET occupancy scan), ~5.5 (at the conclusion of the first PET occupancy scan), 24 (prior to tracer injection), and ~27.5 hours (at the conclusion of the second PET occupancy scan).

An aliquot of plasma from the blood samples collected for Compound 9 PK was stored and archived for potential plasma 2-AG assay (or assay of other endogenous lipids (e.g., AEA and additional monoacylglycerol species)).

Arterial sampling (up to 21 samples) was obtained during the course of each PET imaging scan procedure including: up to 6 samples of 5 mL of blood (+1 mL discard/sample) and up to 15 samples of 1.5 mL of blood (+1 mL discard/sample). The timepoints for collection of these samples are (the 5 mL samples are bolded and underlined): approximately 0.75, 1.5, 2.25, 3, 3.75, 4.5, 5.25, 6, 8, 10, 15, 20, 25, 30, 45, 60, 90, 120, 150, 180 and 210 min post-injection of Compound 8F. These samples were assayed for radioactive activity and metabolite analysis to determine the concentration and percent parent fraction of Compound 8F in plasma. While not all timepoints were collected in all subjects, the total number of blood samples collected per subject did not exceed the number and volumes indicated above. (Maximum blood draw, including discards=78.5 mL per PET scan×3 scans=235.5 mL).

Up to two samples (approximately 7 mL per sample) were drawn prior to each Compound 8F injection for estimation of the free fraction (not bound to protein) of parent Compound 8F in plasma.

Peripheral blood was collected at the following timepoints for evaluation of PBMC MGLL target engagement: prior to treatment (0 hour) and at the following time points after administration of study drug at times: 2 (prior to tracer injection), ~3.5-4 (midway through first PET occupancy scan), ~5.5 (at the conclusion of the first PET occupancy scan), 24 (prior to tracer injection), and ~27.5 hours (at the conclusion of the second PET occupancy scan). While there was a 1 hour postdose collection for PK, there was not a PBMC MGLL TE sample collected until 2 hours postdose.

A fit-for-purpose mass spectroscopy-based substrate assay was used in this clinical trial for the determination in PBMC of MGLL target engagement by Compound 9. Residual PBMC fractions from this study (i.e., after completion and unblinding of the study) were also assayed in an exploratory fashion for MGLL target engagement using ABPP techniques.

Safety was assessed by clinical assessment of adverse events and by repeated measurements of vital signs, physical examination, weight, neurological examinations, 12-lead electrocardiograms (ECGs), and by the standard clinical laboratory safety tests (hematology, chemistry, and urinalysis).

Adverse event inquiry occured at 0 hour (pre-dose) and at each visit throughout the study, up to and including the post study visit (at least 14 days after the last dose of study drug).

Statistical Methods:

The following populations were defined for the analysis and reporting of data. All subjects were reported, and their data analyzed, according to the treatment(s) they actually received:

All Subjects as Treated (AST)—All subjects received at least one dose of the investigational drug. This population was used for assessments of safety and tolerability.

Per-Protocol (PP)—The set of data generated by the subset of subjects who complied with the protocol sufficiently to ensure that these data exhibit the effects of treatment, according to the underlying scientific model. Compliance covered such considerations as exposure to treatment, availability of measurements and absence of major protocol violations. At the end of the study, all subjects who are compliant with the study procedure as aforementioned and have available data from at least one treatment were included in the primary analysis dataset. This population was used for the PK and PD analyses.

Compound 9 pharmacokinetic parameters (e.g., $C_{max}$, AUC0-t, $AUC_{0-tau}$, $AUC_{inf}$, $T_{max}$, $t_{1/2}$ and $AUC_{0-24}$) were calculated as appropriate using plasma concentration versus time profile data using the Non-Compartment Analysis Object of Phoenix WinNonlin® Software (Version 6.3 or higher, Pharsight Inc., Mountain View, Calif., USA).

Where assayed, single-dose 2-AG concentrations and PBMC MGLL TE percentages were listed and summarized by time point and treatment using descriptive statistics. For each subject and each post-baseline time point, percent of baseline was calculated. Baseline is defined as the level in the last sample before administration of oral study drug. Percent of baseline was computed via back-transformation from log-scale summary statistics. Other PD readouts were summarized similarly.

Safety and Adverse Events: Sample size for initial human safety studies are limited and chosen based on customary values. Power calculations for comparison of adverse event rates are too imprecise to be clinically meaningful because the actual rates are not even approximately known. However, if an adverse event occurs at a rate of 1% or 10% then the probability of observing such an adverse event among 6 subjects receiving that dose will be 6% or 47%, respectively. If no AE of a given type is observed in any of 6 subjects at a given dose then, with 80% (90%) confidence, the true incidence of the adverse event at that dose is at most 24% (32%).

PET Imaging to determine MGLL EO: The size of the population under study was chosen so that a balance is sought between feasibility and guarantee of meaningful imaging results. Based on the combination of quantification accuracy for PET and previous studies in these populations, groups of 10-12 subjects would give meaningful group results, giving a sufficient safety margin to the study.

Results:

1. Compound 8F was evaluated in a clinical Phase 1 study to evaluate brain MGLL enzyme occupancy before and after oral administration of Compound 9 to healthy volunteers age 18-55 years. Nine healthy male and five healthy female subjects were enrolled in this study. Subjects underwent a baseline Compound 8F PET scan, and then returned 3 to 21 days later for single-dose oral administration of Compound 9 and two further Compound 8F PET scans. Orally administered single Compound 9 doses ranged from 10-60 mg, and intravenously administered single Compound 8F doses were ≤10 μg by mass, and ≤160 MBq by radiation. The two Compound 8F occupancy PET scans started 2- and 24-hours after oral administration of Compound 9. Total PET scan duration was 3.5 hours per scan.
2. Arterial blood samples were analyzed by HPLC to determine the fraction of intact parent compound at each time point post-injection.
3. PET data was processed to extract Time Activity Curves (TACs) for predefined brain regions.
4. PET TACs, parent fraction and blood and plasma curves were used for modeling tracer kinetics. A two-tissue compartment model (2TCM) was fitted to the PET TACs. The plasma curve was multiplied by the parent fraction to generate a metabolite corrected plasma input function. The PET signal from blood volume was accounted for by including the blood curve in the model. A Patlak graphical analysis was performed by fitting a regression line to the data segment starting at 30 minutes post-injection. The slope of the Patlak fit corresponds to $K_i$.

Figure 9:
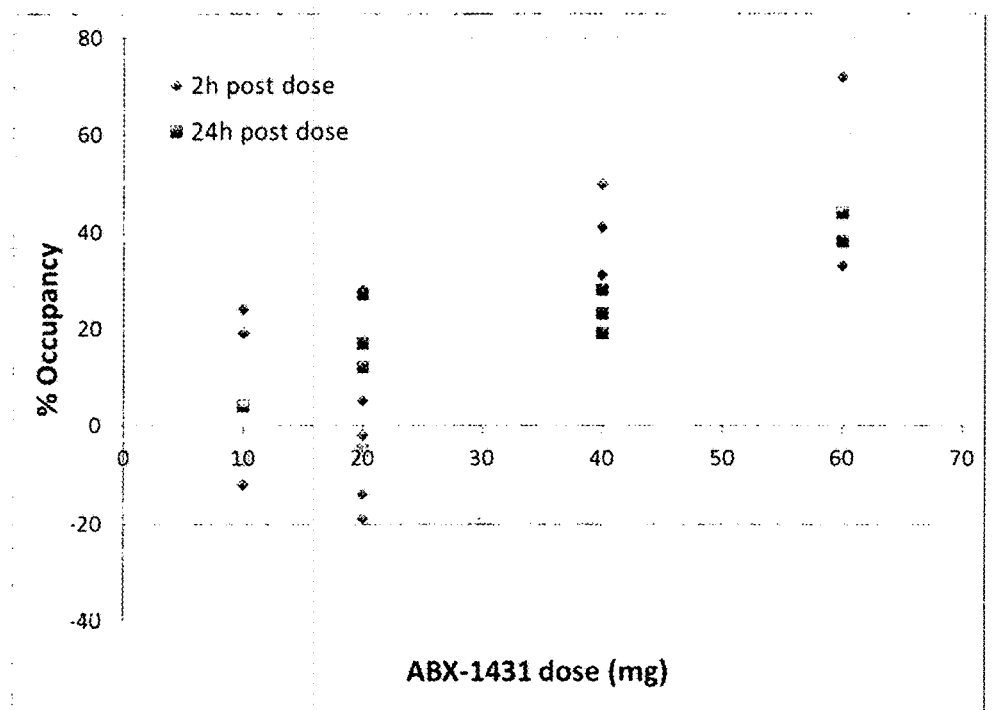
FIG. 9 depicts occupancy values versus Compound 9 dose.

5. To determine dose occupancy values, kinetic analysis was performed for baseline and postdose PET scans. A regression line was fitted between baseline and post-dose quantitative endpoints and occupancy was determined as: occ (%)=(1−slope)×100. Occupancy values determined for a quantitative endpoint combining Patlak $K_i$ and 2TCM $K_j$, that is $K_iK_j/(K_j−K_i)$ (FIG. 9).

6. Based on the observed dose occupancy data, a dose-related increase in brain MGLL occupancy with increasing doses of orally administered Compound 9 was observed.

What is claimed is:

1. A radiolabeled monoacylglycerol lipase (MGLL) occupancy probe comprising an MGLL inhibitor containing a positron emission tomography (PET) tracer radionuclide, wherein the MGLL inhibitor has the structure of Formula (Ib):

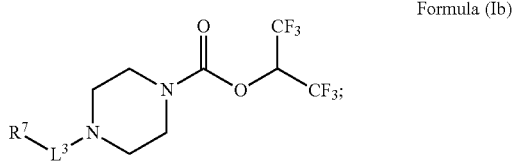

Formula (Ib)

wherein
$L^3$ is —$CH_2$—;
$R^7$ is phenyl; wherein $R^7$ is substituted by one, two, or three moieties independently selected from $R^h$;
$R^a$ and $R^b$, together with the nitrogen to which they are attached, form a 4-6 membered saturated heterocyclic ring, which may have an additional heteroatom selected from O, S, and N, wherein the 4-6 membered saturated heterocyclic ring is substituted by $C_{1-6}$haloalkyl; and
$R^h$ is selected from the group consisting of: halogen, $C_{1-6}$alkyl (optionally substituted by one, two, or three halogens), and $R^aR^bN$—, wherein at least one $R^h$ is $R^aR^bN$—;
or a pharmaceutically acceptable salt, solvate, hydrate, tautomer, or stereoisomer thereof.

2. The radiolabeled MGLL occupancy probe of claim 1, wherein the PET tracer radionuclide is $^{18}F$.

3. The radiolabeled MGLL occupancy probe of claim 2, wherein the radiolabeled MGLL occupancy probe forms a covalent adduct with the active-site serine in MGLL.

4. The radiolabeled MGLL occupancy probe of claim 1 having the structure:

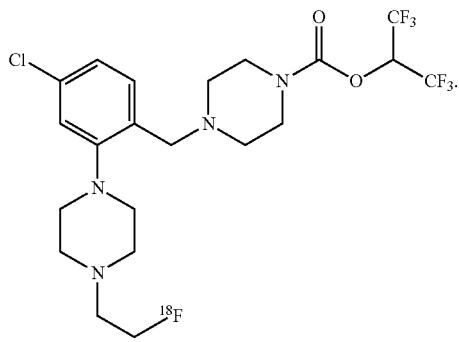

5. A compound having the structure of Formula (V):

Formula (V)

wherein p is 0, 1, or 2;

$R^d$ is H or $C_{1-6}$alkyl;

$L^3$ is a bond, —$CH_2$—, —$S(O)_2$—, or —$C(O)$—;

$R^7$ is phenyl substituted by $R^aR^bN$— and a moiety selected from the group consisting of: halogen and $C_{1-6}$alkyl (optionally substituted by one, two, or three halogens);

$R^a$ and $R^b$, together with the nitrogen to which they are attached, form a 4-6 membered heterocyclic ring or a 9-10 membered bicyclic heterocycle or spirocyclic ring, which may have an additional heteroatom selected from O, S, and N; wherein the 4-6 membered heterocyclic ring or 9-10 membered bicyclic heterocycle or spirocycle is substituted by $C_{1-6}$haloalkyl;

or a solvate, hydrate, tautomer, stereoisomer, or pharmaceutically acceptable salt thereof.

6. The compound of claim 5, wherein p is 0.

7. The compound of claim 6, wherein $L^3$ is —$CH_2$—.

8. The compound of claim 7, wherein $R^a$ and $R^b$, together with the nitrogen to which they are attached, form a 4-6 membered heterocyclic ring, which may have an additional heteroatom selected from O, S, and N; wherein the 4-6 membered heterocyclic ring is substituted by $C_{1-6}$haloalkyl.

9. The compound of claim 8, wherein the 4-6 membered heterocyclic ring is piperazine.

10. The compound of claim 9 having the structure

* * * * *